US010337067B2

(12) United States Patent
Kirkpatrick et al.

(10) Patent No.: US 10,337,067 B2
(45) Date of Patent: Jul. 2, 2019

(54) COMPOSITIONS AND METHODS FOR DETERMINING LIKELIHOOD OF TWINNING

(71) Applicant: Wisconsin Alumni Research Foundation, Madison, WI (US)

(72) Inventors: Brian Wayne Kirkpatrick, Fitchburg, WI (US); Eui-Soo Kim, Laurel, MD (US); Chad D. Bierman, Holmen, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 14/668,512

(22) Filed: Mar. 25, 2015

(65) Prior Publication Data
US 2017/0037470 A1 Feb. 9, 2017

Related U.S. Application Data

(62) Division of application No. 12/568,334, filed on Sep. 28, 2009, now abandoned.

(60) Provisional application No. 61/100,697, filed on Sep. 26, 2008.

(51) Int. Cl.
*C12Q 1/68* (2018.01)
*C12P 19/34* (2006.01)
*C12Q 1/6883* (2018.01)
*G16B 20/00* (2019.01)

(52) U.S. Cl.
CPC .......... *C12Q 1/6883* (2013.01); *G16B 20/00* (2019.02); *C12Q 2600/124* (2013.01); *C12Q 2600/156* (2013.01); *C12Q 2600/172* (2013.01)

(58) Field of Classification Search
CPC ............ C12Q 1/6883; C12Q 2600/124; C12Q 2600/156; G06F 19/18
See application file for complete search history.

(56) References Cited

U.S. PATENT DOCUMENTS

2001/0053519 A1 12/2001 Fodor et al.

OTHER PUBLICATIONS

Reference SNP (refSNP) Cluster Report: rs109679113, from www.ncbi.nlm.nih.gov. printed on Feb. 24, 2017, pp. 1-2.*
Kirkpatrick, B.W. "Diallelic single-strand conformation polymorphism in the bovine insulin-like growth factor-1 third intron" , Animal Genetics (1993) 24, 144.*
Allele coding tutorial, printed from http://gengen.openbioinformatics.org/en/latest/tutorial on Oct. 11, 2017.*
Nicolazzi, E.L. et al. Microarrays 2016, 5, 17.*
Charlier C. et al. "Highly effective SNP-based association mapping and management of recessive defects in livestock" Nature Genetics (Apr. 2008) vol. 40, No. 4, pp. 449-454 (Year: 2008).*
Abel, K., et al., "Genome-wide SNP association: Identification of susceptibility Alleles for osteoarthritis", Autoimmunity Reviews, vol. 5, pp. 258-263 (2006).
Ahern, H., "Biochemical, reagent kits offer scientists good return on investment", The Scientist, pp. 20, 22 (1995).
Allan, M.F., et al., "Confirmation of QTL using a low density SNP map for twinning and ovulation rate on bovine chromosome", J. Animal Science, vol. 5, pp. 46-56 (2008).
Allan, M.F., et al., "Fine mapping of QTL for twinning and ovulation rate using low density SNP map . . . ", Plant and Animal Genome XV, San Diego (2007), Abstract only.
Andersson, L., et al., "Domestic-Animal Genomics: Deciphering the genetics of complex traits", Nature Review Genetics, vol. 5, pp. 202-212 (2004).
Arias, J.A., et al., "Mapping of bovine ovulation rate QTL using three generation pedigrees", Animal Genetics, vol. 35, pp. 7-13 (2004).
Barrett, J.C., et al., "Haploview: analysis and visualization of LD and haplotype maps", Bioinformatics, vol. 21, pp. 263-265 (2005).
Barrett, J.C., et al., "Evaluating coverage of genome-wide association studies", Nature Genetics, vol. 38, pp. 659-662 (2006).
Beerepoot, G.M., et al., "The economics of naturally occurring twinning in dairy cattle", Journal of Dairy Science, vol. 75, pp. 1044-51 (1992).
Blattman, AN., et al., "A search for quantitative trait loci for ovulation rate in cattle", Animal Genetics, vol. 27, pp. 157-162 (1996).
Boehringer Mannheim 1997 Biochemicals Catalog, cover and Non-radioactive Labeling and Detection of Nucleic Acids, p. 95.
Calus, M.P.L., et al., "Accuracy of genomic selection using different methods to define haplotypes", Genetics, vol. 178, pp. 553-561 (2008).
Chiu, Y.E., "A comparison in association and linkage genome-wide scans for alcohol susceptibility genes . . . ", BMC Genetics, vol. 6 (Supplement 1), p. S89 (2005).
Cobanoglu, O., et al., "Genome screen for twinning rate QTL in four North American Holstein families", Animal Genetics, vol. 36, pp. 303-308 (2005).
Cruickshank, J., et al., "Evidence for quantitative trait loci affecting twinning rate in North American Holstein cattle", Animal Genetics, vol. 35, pp. 206-212 (2004).
Database SNP NCBI, Bethesda, MD 20894, USA, "Reference Snp Cluster Report: rs29012841" XP002564253, Feb. 5, 2005.
Echternkamp, S.E., et al., "Concentrations of insulin-like growth factor-I in blood and ovarian follicular fluid of cattle . . . ", Biol. Reproduction, vol. 43, pp. 8-14 (1990).
Eddy, R.G., et al., "An economic assessment of twin births in British dairy herds", Veterinary Record, vol. 129, pp. 526-529 (1991).

(Continued)

*Primary Examiner* — Stephen T Kapushoc
(74) *Attorney, Agent, or Firm* — Potter Anderson and Corroon LLP

(57) ABSTRACT

Collections of polynucleotides useful for estimating breeding value or detecting likelihood of twinning are disclosed. The polynucleotides are used to detect genomic sequences quantitatively associated with the twinning trait. Also disclosed are methods and kits for using the collections to estimate breeding value or predict likelihood of twinning.

8 Claims, 10 Drawing Sheets

Specification includes a Sequence Listing.

(56) References Cited

OTHER PUBLICATIONS

Ehrenreich, I.M., et al., "The genetic architecture of shoot branching in *Arabidopsis thaliana*: a comparative assessment . . . ", Genetics, vol. 176, pp. 1223-1236 (2007).
Fricke, P.M., et al., "Effect of milk production on the incidence of double ovulation in dairy cows", Theriogenology, vol. 52, pp. 1133-1143 (1999).
Gilmour, A.R., et al., "ASReml User Guide Release 1.0.", Published by: Hemel Hempstead: VSN International (2002).
Goddard, M.E., et al., "Can the same genetic . . . multiple breeds?", Proc. 8th World. Congr.Genet. Appl. Livest. Prod., Belo Horizonte, Brazil (2006). (on CD-ROM not included).
Gonda, M.G., et al., "Identification of an ovulation rate QTL in cattle on BTA14 using selective DNA pooling and interval mapping", Animal Genet., vol. 35, pp. 298-304 (2004).
Grapes, L, et al., "Comparing linkage disequilibrium-based methods for fine mapping quantitative trait loci." Genetics, vol. 166, pp. 1561-1570 (2004).
Green, P., Falls, K., and Crook, S., "Documentation for CRIMAP", version 2.4. (1990).
Gregory, K.E., et al., "Genetic and environmental parameters for ovulation rate, twinning rate, and environmental parameters . . . ", J. Animal Sci., vol. 75, pp. 1213-1222 (1997).
Grisart, B., et al., "Positional candidate cloning of a QTL in dairy cattle: Identification of a missense mutation . . . ", Genome Res., vol. 12, pp. 222-231 (2002).
Hampe, J., et al., "A genome-wide association scan of nonsynonymous SNPs identifies a susceptibility variant for Crohn's . . . ", Nature Genetics, vol. 39, pp. 207-211 (2007).
Hardenbol, P., et al., "Highly multiplexed molecular inversion probe genotyping: Over 10,000 targeted SNPs genotyped . . . ", Genome Research, vol. 15, pp. 269-275 (2005).
Hayes, B.J., et al., "Novel Multilocus Measure of linkage disequilibrium to estimate past effective population size", Genome Research, vol. 13, pp. 635-643 (2003).
Hayes, B.J., et al "The distribution of the effects of genes affecting quantitative traits in livestock", Genetics Selection Evolution, vol. 33, pp. 209-229 (2001).
Hirschhorn, J. N., & Daly, M. J., "Genome-wide association studies for common diseases and complex traits", Nature Review Genetics, vol. 6, pp. 95-108 (2005).
Johanson, J.M., et al., "Twinning rates for North American Holstein", Journal Dairy Science, vol. 84, pp. 2081-2088 (2001).
Kappes, S.M., et al., "Initial results of genomic scans for ovulation rate in a cattle population selected for increased . . . ", J. Animal Science, vol. 78, pp. 3053-3059 (2000).
Karlsen, A., et al., "Twinning rate in Norwegian cattle: frequency, (co)variance components, and genetic trends", Journal of Animal Science, vol. 78, pp. 15-20 (2000).
Kirkpatrick, B.W., et al., "Mapping quantitative trait loci for bovine ovulation rate", Mammalian Genome, vol. 11, pp. 136-139 (2000.
Lander, E.S., & Kruglyak, L., "Genetic dissection of complex traits: guidelines for interpreting and reporting linkage results", Nature Genetics. vol. 11, pp. 241-247 (1995).
Lien, S., et al., "A primary screen of the bovine genome for quantitative trait loci affecting twinning rate", Mammalian Genome, vol. 11, pp. 877-882 (2000).
Markusfeld, O., "Periparturient traits in seven high dairy herds. Incidence rates, association with parity, and . . . ", J. Dairy Science, vol. 70, pp. 158-166 (1987).
Maestrini, E., et al., "High-density SNP association study and copy number variation analysis of the AUTS1 and AUTS5 loci . . . ", Molecular Psychiatry, pp. 1-15 (2009).
McKay, S.D., et al., "Construction of bovine whole-genome radiation hybrid and linkage using high-throughput genotyping", Animal Genetics, vol. 38, pp. 120-125 (2007).

Meuwissen, TH.E., & Goddard, M.E., "Prediction of identity by descent probabilities from marker-haplotypes", Genetics Selection Evolution, vol. 33, pp. 605-634 (2001).
Meuwissen, T,H.E., et al., "Fine mapping of a quantitative trait locus twinning rate using combined linkage and linkage . . . ", Genetics, vol. 161, pp. 373-379 (2002).
Meuwissen, T.H.E., et al., "Prediction of total genetic value using genome-wide dense marker maps", Genetics, vol. 157, pp. 1819-1829 (2001).
Monget, P., et al., "Regulation of ovarian folliculogenesis by IGF and BMP system in domestic animals", Domestic Animal Endocrinology, vol. 23, pp. 139-154 (2002).
Nezer, C., et al., "Haplotype sharing refines the location of an imprinted quantitative trait locus with major effect on muscle . . . ", Genetics, vol. 165, pp. 277-285 (2003).
Nielen, M., et al., "Twinning in dairy cattle: A study of risk factors and effects", Theriogenology, vol. 32, pp. 845-862 (1989).
Pfaffl, M.W., et al., "Real-time RT-PCR quantification of insulin-like growth factor (IGF)-1, IGF-1 receptor, IGF-2, IGF-2 receptor,insulin receptor, growth hormone receptor . . . ", Domestic Animal Endocrinology vol. 22, pp. 91-102 (2002).
Rioux, J.D., et al., "Genome-wide association study identifies new susceptibility loci for Crohn disease and implicates . . . ", Nature Genetics, vol. 39, pp. 596-604 (2007).
Risch, N., & Merikangas, K., "The future of genetic studies of complex human diseases", Science, vol. 273, pp. 1516-1517 (1996).
Ron, M., et al., "Genetic analysis of twinning rate in Israeli Holstein cattle", Genetics Selection Evolution, vol. 22, pp. 349-359 (1990).
Sobel, E., & Lange, K., "Descent graphs in pedigree analysis: applications to haplotyping, location scores, and . . . ", Am. J. Human Genetics, vol. 58, pp. 1323-1337 (1996).
Song, C.-X., et al. "Mapping new nucleotide variants in the genome and transcriptome", Nat. Biotechnol., vol. 30(11), pp. 1107-1116 (2012).
Sved, J.A., "Linkage disequilibrium and homozygosity of chromosome segment in finite populations", Theoretical Population Biology, vol. 2, pp. 125-141 (1971).
Van Raden, P.M., et al., "Invited Review: Reliability of genomic predictions for North American Holstein bulls", Journal of Dairy Science, vol. 92, pp. 16-24 (2009).
Wang, N., et al., "Distribution of recombination . . . haplotype blocks: the interplay of population history, recombination, and mutation", vol. 71, pp. 1227-1234 (2002).
Weller, J.I., et al., "A new approach to the problem of multiple comparisons in the genetic dissection of complex trait", Genetics, vol. 150, pp. 1699-1706 (1998).
Weller, J.I., et al., "Detection of quantitative trait loci affecting twinning rate of Israeli Holsteins by the daughter design", J. Dairy Sci., vol. 91, pp. 2469-2474 (2008).
Windig, J.J., & Meuwissen, T.H.E., "Rapid haplotype reconstruction in pedigrees with dense marker maps", Journal of Animal Breeding and Genetics, vol. 121, pp. 26-39. (2004).
Zimin, A. V., et al., "A whole-genome assembly of the domestic cow, Bos taurus", Genome Biology, vol. 10, pp. R42,1-10 (2009).
International Search Report and Written Opinion in application No. PCT/US2009/058604, dated Apr. 15, 2010.
Restriction Requirement in U.S. Appl. No. 12/568,334, dated Apr. 4, 2011.
Non-Final Office Action in U.S. Appl. No. 12/568,334, dated Jul. 20, 2011.
Final Office Action in U.S. Appl. No. 12/568,334, dated Dec. 5, 2011.
Non-Final Office Action in U.S. Appl. No. 12/568,334, dated Jul. 8, 2013.
Final Office Action in U.S. Appl. No. 12/568,334, dated Dec. 31, 2013.
Non-Final Office Action in U.S. Appl. No. 12/568,334, dated Sep. 29, 2014.

\* cited by examiner

COMPOSITIONS AND METHODS FOR DETERMINING LIKELIHOOD OF TWINNING

CROSS-REFERENCE TO RELATED APPLICATIONS

Divisional of U.S. application Ser. No. 12/568,334, filed Sep. 28, 2009, which claims benefit under 35 U.S.C. § 119(e) of U.S. Provisional Application No. 61/100,697, filed Sep. 26, 2008, the entire contents of each of which are incorporated by reference herein.

GOVERNMENT RIGHTS

This invention was made with government support under 2005-35205-15556 and 08-CRHR-6055 awarded by the USDA/NIFA. The government has certain rights in the invention.

FIELD OF THE INVENTION

The invention described herein relates generally to animal genetics and improvements in cattle breeding. More particularly, it relates to compositions and methods for predicting the likelihood of twinning in cattle.

BACKGROUND OF THE INVENTION

The trait of twinning rate has been shown to possess economic value to the dairy industry. The negative effects of increased twinning rate include increased dystocia, retained placenta, longer return-to-estrus intervals, an increased frequency of freemartins, reduced milk production and more frequent involuntary culling (Beerepoot et al. 1992; Niellen et al. 1989). It has been estimated that economic loss to the dairy industry is around $110/cow due to lost revenue and increased costs from producing twin calves instead of singles (Beerepoot et al. 1992; Eddy et al. 1991); after accounting for effects of inflation, the cost in current dollars is likely considerably higher. Reducing the incidence rate of twinning will therefore reduce this loss and increase profitability for the dairy industry.

Genetic progress for selection on twinning rate has been made (Gregory et al. 1997). Non-zero estimates of heritability for the trait have been observed, suggesting an additive genetic component. Estimates have ranged from 0.06%-21.6% depending on parity inclusion and type of model used in its estimation (Johanson et al. 2001; Ron et al. 1990; Karlsen et al. 2000). Nevertheless, the majority of evidence suggests twinning rate to be a lowly heritable trait, and therefore an excellent candidate for the use of marker assisted selection to aid in its genetic progress.

Various studies have identified QTL affecting twinning rate or ovulation rate in cattle (Blattman et al. 1996, Kappes et al. 2000, Kirkpatrick et al. 2000, Lien et al. 2000, Arias and Kirkpatrick, 2004, Gonda et al. 2004, Cruickshank et al. 2004, Cobanoglu et al. 2005). Linkage mapping has shown positive results for the existence of QTL segregating in the Holstein population. A drawback of linkage mapping is that confidence intervals remain broad (Andersson & Georges 2004). In many reports throughout the literature, analyses have attempted to refine the locations of QTL using additional markers or larger datasets; however, this has been accomplished with minimal success. Alternative tools or approaches are necessary to refine these locations.

Recent advances in technology have facilitated screening of the genome with markers at higher density than previously possible (Hardenbol et al. 2005; Thompson et al. 2007). An example of a proposed analysis method has been reported by Meuwissen & Goddard (2001). Their method predicts identity by descent (IBD) probabilities at a given location using the information from the marker genotypes, or haplotype, surrounding the given location. Haplotypes provide more information compared to single-markers when linkage disequilibrium (LD) is weak, consequently improving the power of QTL detection.

Twinning or ovulation rate QTL on bovine chromosome 5 (BTA5) have been identified in previous studies. Twinning rate QTL were detected between 55~65 Mb (bovine genome assembly 3.1) on BTA5 in the Norwegian dairy cattle population (Lien et al. 2000) and the North American Holstein population (Cruickshank et al. 2004). An ovulation rate QTL was detected in the 40 cM (~30 Mb) region of BTA5 (Kappes et al. 2000) in the USDA twinning population.

Though progress has been made, there remains a need for improved methods and genetic markers for predicting twinning potential for individual animals and within herds.

SUMMARY OF THE INVENTION

One aspect of the invention features a collection of one or more polynucleotides, each of which is at least partially complementary to a sequence in a bovine genome, the presence or absence of which such complementary sequences in the bovine genome is quantitatively associated with the trait of twinning in a cattle population, wherein the collection comprises at least one sequence that is quantitatively associated with twinning with statistical significance of at least $p \le 0.01$. More particularly, the collection comprises at least one sequence that is quantitatively associated with twinning with statistical significance of at least $p \le 0.005$, and even more preferably $p \le 0.001$. In various embodiments, the collection is useful for estimating breeding value in cattle In certain embodiments, each polynucleotide represents one allele of a SNP in the bovine genome.

At least one of the polynucleotides is complementary to a sequence located on bovine chromosome 5 (BTA5). More specifically, at least one of the polynucleotides is complementary to a sequence that maps between 55-75 Mb of BTA5; or, more particularly, between 64-73 Mb of BTA5. In another embodiment, one or more of the polynucleotides is complementary to a sequence that maps on BTA5 at any of 24-26 Mb, 49-51 Mb, 64 to 65 Mb, or 69-70 Mb, or, more particularly, between 69.2 to 69.9 Mb.

At least one of the polynucleotides may be complementary to a sequence located in a genomic sequence for Insulin-like Growth Factor 1 (IGF1). Alternatively, at least one of the polynucleotides is complementary to a sequence in a genomic sequence for synapsin III (SYN3), synapsin III isoform A (SYN3A), collagen type X alpha-1 (COL10A1) precursor, eukaryotic translation initiation factor 3, subunit 7 (EIF3S7), insulin-like growth factor 1 (IGF1), inhibin beta-C (INHBC), cytoskeleton-associated protein 4 (CKAP4), or Alpha2-HS glycoprotein (AHSG.)

In various embodiments, the collection comprises at least one polynucleotide useful for detecting one or more particular SNPs of the bovine genome or BTA5, as described in detail herein.

Another aspect of the invention features a method for estimating the likelihood of twinning in one or more members of a cattle population comprising the steps of: (a)

providing a collection of one or more polynucleotides, each of which is at least partially complementary to a sequence in a bovine genome, comprising at least one sequence that is quantitatively associated with twinning with statistical significance of at least p≤0.01; (b) using the collection to determine the presence or absence of sequences complementary to one or more polynucleotides from the collection in one or more members of the cattle population genome, wherein the presence or absence of the complementary sequences is quantitatively associated with the trait of twinning in a cattle population; and (c) estimating the likelihood of twinning based on the results of step b). In certain embodiments, the estimating step b) comprises a laboratory analysis and step c) comprises a statistical calculation. In other embodiments, step b) comprises a field test, and in specific embodiments may comprises a threshold estimate or a visual indicator of acceptability.

Preferably, the method utilizes at least one sequence that is quantitatively associated with twinning with statistical significance of at least p≤0.01, more preferably, p≤0.005, even more preferably, p≤0.001.

In various embodiments, the method is useful for estimating breeding value in cattle In certain embodiments, each polynucleotide represents one allele of a SNP in the bovine genome.

The method utilizes at least one of the polynucleotides complementary to a sequence located on bovine chromosome 5 (BTA5). More specifically, at least one of the polynucleotides is complementary to a sequence that maps between 55-75 Mb of BTA5; or, more particularly, between 64-73 Mb of BTA5. In another embodiment, one or more of the polynucleotides is complementary to a sequence that maps on BTA5 at any of 24-26 Mb, 49-51 Mb, 64 to 65 Mb, or 69-70 Mb, or, more particularly, between 69.2 to 69.9 Mb.

In another embodiment, the method utilizes at least one polynucleotides complementary to a sequence located in a genomic sequence for Insulin-like Growth Factor 1 (IGF1). Alternatively, at least one of the polynucleotides is complementary to a sequence in a genomic sequence for synapsin III (SYN3), synapsin III isoform A (SYN3A), collagen type X alpha-1 (COL10A1) precursor, eukaryotic translation initiation factor 3, subunit 7 (EIF3S7), insulin-like growth factor 1 (IGF1), inhibin beta-C (INHBC), cytoskeleton-associated protein 4 (CKAP4), or Alpha2-HS glycoprotein (AHSG.)

In various embodiments, the method utilizes at least one polynucleotide useful for detecting one or more particular SNPs of the bovine genome or BTA5, as described in detail herein.

Another aspect of the invention features a kit for estimating breeding value or predicting the likelihood of twinning comprising: (1) a collection of polynucleotides as described above; and (2) instructions for using the collections for estimating breeding value or predicting the likelihood or genetic potential for twinning.

Other features, and advantages of the present invention will be readily apparent to those skilled in the art, by reference to the drawings, detailed description and examples that follow.

DETAILED DESCRIPTION

Definitions

Figure 1:
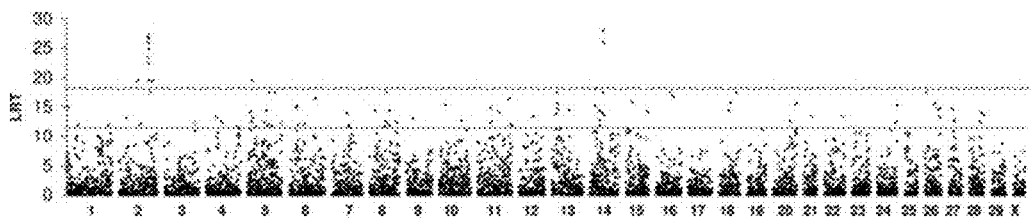
FIG. 1: Genome-wide single marker association tests. Log likelihood ratio test (LRT) of each marker association test is plotted by SNP in sequential order position (not proportional to Mb location). SNP results are organized by chromosome with chromosome identification indicated along the x-axis. Significant ($p=2.3\times10^{-5}$, solid line) and suggestive ($p=7\times10^{-4}$, dotted line) thresholds are indicated with horizontal lines.

The following abbreviations may be used herein:
cM, centiMorgan;
CWER, comparison-wise error rates;
FDR; false discovery rate;
HWE, Hardy-Weinberg equilibrium;
IBD, identity by descent;
Kb, kilobase;
LD, linkage disequilibrium;
LLD, linkage-linkage disequilibrium;
LRT, log-likelihood ratio;
MAF, minor allele frequency;
Mb, megabase;
NCBI, National Center for Biotechnology Information;
PEV, prediction error variance;
PTA, predicted transmitting ability;
QTL, quantitative trait loci; and
SNP, single nucleotide polymorphism.

The term "individual" when referring to an animal means an individual animal of any species or kind.

The term "animal" is used in a general sense and means a human or other animal, including avian, bovine, canine, equine, feline, hicrine, lupine, murine, ovine, and porcine animals. Preferably the animal is a mammal, particularly a bovine. Unless otherwise specified, or clear from the context, the term "mammal" herein includes human. The term "non-human" animal may be used herein to refer to any animal other than human.

As used herein, "linkage disequilibrium" (or "LD") refers to allelic association between specific alleles at two or more neighboring loci in the genome, e.g., within a population. LD can be determined for a single marker or locus, or multiple markers. LD is sometimes expressed herein as $r^2$ values where $r^2=1/(4N_ec+1)$ where c=recombination rate (M), and Ne=effective population size. (Sved, 1971)

As used herein, "allele" refers to one or more alternative forms of a particular sequence that contains a SNP. The sequence may or may not be within a gene, and may be within a coding or noncoding portion of such a gene, and may be within an exon or an intron of a particular gene.

"Quantitative trait locus," (or "QTL"), as used herein is a genomic sequence that is associated with a particular phenotypic trait. Multiple QTL may be identified for a particular trait, and they are frequently found on different chromosomes. The number of QTLs that associate significantly with a particular phenotypic trait may provide an indication of the genetic architecture of a trait, the number of genes that effect the trait, or the extent of the effect of one or more of those genes. One or more QTL that significantly associate with a trait may be candidate genes underlying that trait, which can be sequenced and identified. The significance of the degree of association of a given QTL with a particular trait can be assessed statistically, e.g. through QTL mapping of the alleles that occur in a locus and the phenotypes that they produce. Statistical analysis is preferred to demonstrate whether an observed association with a trait is significant. The presence of a QTL, and its location identify a particular region of the genome as potentially containing a gene that is associated, directly (e.g., structurally) or indirectly (e.g., regulatory) with the trait being analyzed. The probability of association can be plotted for various markers associated with the trait spaced across a chromosome, or throughout the genome.

Positions on chromosomes of the bovine (*Bos taurus*) genome (BTA) are calculated with reference to bovine genome assembly 3.1 unless otherwise noted.

A "polynucleotide" includes single-stranded or a multi-stranded nucleic acid molecules comprising two or more sequential bases, including any single strand or parallel and anti-parallel strands of a multi-stranded nucleic acid. Polynucleotide may be of any length, and thus, include very large nucleic acids, as well as short ones, such as oligonucleotides.

The term "oligonucleotide" typically refers to short polynucleotides, generally no greater than about 50 nucleotides. It will be understood that if a nucleotide sequence is denoted by a DNA sequence (i.e., A, T, G, C), the corresponding RNA sequence (i.e., A, U, G, C, wherein "U" replaces "T") is also included.

As used throughout, ranges herein are stated in shorthand, so as to avoid having to set out at length and describe each and every value within the range. Any appropriate value within the range can be selected, where appropriate, as the upper value, lower value, or the terminus of the range. For example, a range of 0.1-1.0 represents the terminal values of 0.1 and 1.0, as well as the intermediate values of 0.2, 0.3, 0.4, 0.5, 0.6, 0.7, 0.8, 0.9, and all intermediate ranges encompassed within 0.1-1.0, such as 0.2-0.5, 0.2-0.8, 0.7-1.0, and so on.

As used herein and in the appended claims, the singular form of a word includes the plural, and vice versa, unless the context clearly dictates otherwise. Thus, the references "a", "an", and "the" are generally inclusive of the plurals of the respective terms. For example, reference to "a SNP", "a method", or "a trait" includes a plurality of such "SNPs", "methods", or "traits." Reference herein, for example to "an association" includes a plurality of such associations, whereas reference to "chromosomes" includes a single chromosome where such interpretation is not precluded from the context. Similarly, the words "comprise", "comprises", and "comprising" are to be interpreted inclusively rather than exclusively. Likewise the terms "include", "including" and "or" should all be construed to be inclusive, unless such a construction is clearly prohibited from the context. Where used herein the term "examples," particularly when followed by a listing of terms is merely exemplary and illustrative, and should not be deemed to be exclusive or comprehensive.

The methods and compositions and other advances disclosed here are not limited to particular methodology, protocols, and reagents described herein because, as the skilled artisan will appreciate, they may vary. Further, the terminology used herein is for the purpose of describing particular embodiments only, and is not intended to, and does not, limit the scope of that which is disclosed or claimed.

Unless defined otherwise, all technical and scientific terms, terms of art, and acronyms used herein have the meanings commonly understood by one of ordinary skill in the art in the field(s) of the invention, or in the field(s) where the term is used. Although any compositions, methods, articles of manufacture, or other means or materials similar or equivalent to those described herein can be used in the practice of the present invention, the preferred compositions, methods, articles of manufacture, or other means or materials are described herein.

All patents, patent applications, publications, technical and/or scholarly articles, and other references cited or referred to herein are in their entirety incorporated herein by reference to the extent allowed by law. The discussion of those references is intended merely to summarize the assertions made therein. No admission is made that any such patents, patent applications, publications or references, or any portion thereof, are relevant, material, or prior art. The right to challenge the accuracy and pertinence of any assertion of such patents, patent applications, publications, and other references as relevant, material, or prior art is specifically reserved. Full citations for publications not cited fully within the specification are set forth at the end of the specification.

Details

The present invention springs in part from the inventors' development of a particularly advantageous approach to identifying genomic regions or genes associated with twinning rate in cattle. The approach first combines the use of linkage and linkage disequilibrium, as well as single-marker association testing using a moderate density whole-genome marker map for twinning rate QTL, to identify putative QTL regions. Twenty independent regions on 14 chromosomes were identified showing significant association for twinning rate (P<0.0007). In addition, 82 and 13 positive single-marker associations reached suggestive and significant thresholds (Lander & Kruglyak, 1995), respectively. Results obtained by this initial approach are then confirmed by (1) validating putative QTL from the linkage-linkage disequilibrium (LLD) analysis results, (2) validating single marker association analyses, and (3) identifying a reduced marker panel to predict genetic merit for twinning rate.

In addition, the inventors have refined the mapping of twinning-rate QTL on bovine chromosome 5 (BTA5) and have identified several positional candidate genes associated with twinning or ovulation rate. Twinning and ovulation rate QTL were mapped previously in the 60-70 Mb genomic region of chromosome 5 (Lien et al. 2000, Cruickshank et al. 2004). Meuwissen et al. (2002) reported the marker bracket of CSSM22 (60.26 Mb) and ILSTS66 (60.27 Mb) showed the highest significance level for twinning rate QTL with the linkage-linkage disequilibrium method. Their result putatively narrowed the genomic region of QTL location to within a 0.7 cM interval between 72.4 cM and 72.9 cM, relative to the USDA-MARC linkage map. However, a significant association between CSSM22 and ILSTS66 and twinning rate may have been detected due to linkage disequilibrium between this marker bracket and a twinning rate QTL outside the region narrowly bounded by these markers. The present inventors have discovered more than two QTL on chromosome 5 through the use of a linkage-linkage disequilibrium analysis with a higher density of SNP markers compared with previous twinning or ovulation rate QTL studies.

Several possible functional candidate genes have also been identified. Of these, IGF1 is a functional candidate gene in the 60-70 Mb QTL region. Association between twinning rate and IGF1 polymorphisms has been previously investigated (Lien et al. 2000, Meuwissen et al. 2002); however, no significant associations between SNPs and twinning rate were identified in that study. In accordance with an embodiment of the present invention, a single marker association testing and linkage-linkage disequilibrium analysis provide support for IGF1 as a candidate gene. As discussed in detail below and in Example 3, IGF1 SNPs 2 and 19 were consistently associated with twinning rate across data sets.

Thus, one aspect of the invention features a collection of polynucleotide sequences, or polynucleotides, each of which is at least partially complementary to a sequence in the bovine genome. The presence or absence of the at least partially complementary sequences, i.e. the sequences in the bovine genome, is quantitatively associated with the trait of twinning in a cattle population. It is known in the art that twinning and ovulation rate are related. Therefore, for purposes herein, it is to be understood that a quantitative association with ovulation rate can be considered a quantitative association with twinning. In various embodiments, the collection comprises at least one sequence that is quantitatively associated with twinning with statistical significance of at least $p \leq 0.01$. Preferred are those collections comprising at least one sequence that is quantitatively associated with twinning with statistical significance of at least $p \leq 0.001$, or even less. In various embodiments, the statistical significance of the quantitative association with twinning is $p \leq 0.001$, $p \leq 0.0009$, $p \leq 0.0008$, $p \leq 0.0007$, $p \leq 0.0006$, $p \leq 0.0005$, or even less. Most preferred are embodiments that have statistical significance of $p \leq 10^{-4}$, $10^{-5}$, or even $10^{-6}$, or lower. Thus, the more highly significant (i.e., the lower the p value) the association is, the more useful the polynucleotide collection can be for predicting twinning. In certain embodiments, polynucleotides useful for indicating the presence or absence of genomic sequences whose association with twinning is, from a statistical view, only suggestive, may be useful herein. More preferred are those polynucleotides useful for indicating the presence or absence of genomic sequences whose association with twinning is highly suggestive, significant, or even highly significant. The skilled artisan will understand that the statistical significance levels deemed suggestive, highly suggestive, significant, or highly significant will vary based on the particular statistical measures used, and the underlying data used to generate the measures of association. Examples of such statistical measures are shown in the working examples.

The collection of polynucleotides is useful for predicting twinning rate or likelihood of twinning within an individual member of a population, or within a herd, and is also useful for other purposes such as estimating breeding value in cattle, whether for genetic purposes (e.g. breed improvement, herd management, and the like), or for economic considerations (e.g., determining or estimating sale or replacement value of an animal or reproductive material from an animal, predicting the value of offspring, estimating gain or loss for milk or meat production (e.g., practical cost or impact of twinning for farmer), or the like, or a combination thereof.

The polynucleotides in the collection can be any sequences, for example, they could encompass a portion of structural genes, regulatory genes, or other sequences, e.g., SNPs, microsatellite sequences, or other sequences of any length found in a genome. The polynucleotides of the collections may correspond to either strand of a nucleic acid heteroduplex. In some embodiments, the polynucleotides are completely complementary to a portion of a genome, while in others they may be less than completely complementary, provided that they are useful for detecting at least a partially complementary sequence in the genome. For example, in various applications the polynucleotides may be used as primers for amplifying specific sequences to be detected, which may not require 100% complementarity. In other embodiments, the polynucleotide may be used as probes for binding to various sequences to be detected. In one embodiment, each polynucleotide is useful for detecting the presence or absence of one allele of a SNP in the bovine genome. In other embodiments, each polynucleotide comprises one allele of a SNP in the bovine genome, or its complement.

The collection can comprise as few as a single polynucleotide, identifying or comprising one location on the bovine genome that predicts likelihood of ovulation or twinning Or the collection can comprise two or more polynucleotides identifying or comprising a region or location on the bovine genome associated with likelihood of ovulation or twinning. Likewise, the collection can comprise two or more polynucleotides identifying or comprising two or more locations or regions in the bovine genome associated with likelihood of ovulation or twinning. By "two or more", is meant 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 82, 84, 85, 86, 87, 88, 89, 90, 90, 92, 93, 94, 95, 96, 97, 98, 99, 100 or more polynucleotides and/or locations or regions in the bovine genome associated with ovulation or twinning rate. Even larger collections may be useful, including collections comprising 110, 120, 130, 140, 150, 160, 170, 180, 190, 200 or more (or incremental numbers in between) polynucleotides and/or locations or regions in the bovine genome associated with ovulation or twinning rate.

The collection can comprise sequences distributed throughout the genome. In one embodiment of the collection, at least one of the polynucleotides is complementary to a sequence located on any bovine chromosome. In one embodiment, the preferred chromosomes include one or more of chromosomes 2, 5, 7, 8, 9, 10, 12, 14, 23, and 26. In another, bovine chromosome 5 (BTA5) is preferred. Especially preferred are particular regions of chromosome 5, including those that are near or encode certain genes. In one embodiment, at least one of the polynucleotides is complementary to a sequence that maps between 55-75 Mb of BTA5. In another embodiment, at least one of the polynucleotides is complementary to a sequence that maps between 64-73 Mb of BTA5.

In various embodiments, the collection comprises one or more polynucleotides complementary to or comprising a sequence that maps on BTA5 at any of 25-35 Mb, 49-51 Mb, 64 to 65 Mb, 64-70 Mb, or 69-70 Mb. Collections comprising polynucleotides complementary to or comprising a sequence that maps on BTA5 between 69.2 to 69.9 Mb are also useful herein. Also useful are polynucleotides that can identify the presence or absence of sequences which map to various overlapping or more specific locations, as set forth in the Examples that follow.

In one embodiment, the collection comprises at least one polynucleotide complementary to a sequence located in a genomic sequence for Insulin-like Growth Factor 1 (IGF1). As mentioned above, IGF1 has been identified herein as a positional candidate that is significantly associated with twinning. Thus, certain preferred collections of polynucleotides feature one or more sequences that can be used to identify the presence or absence of, for example, SNPs within IGF1.

Other genes and sequences near genes may be associated with twinning based on the results. In one embodiment, the collection comprises at least one polynucleotide complementary to a sequence in a genomic sequence for any of synapsin III (SYN3), synapsin III isoform A (SYN3A), collagen type X alpha-1 (COL10A1) precursor, eukaryotic translation initiation factor 3, subunit 7 (EIF3S7), insulin-like growth factor 1 (IGF1), inhibin beta-C (INHBC), inhibin beta-E (INHBE), cytoskeleton-associated protein 4 (CKAP4), small nuclear ribonucleoprotein polypeptide F (SNRPF), or Alpha2-HS glycoprotein (AHSG).

The collection can also comprise at least one polynucleotide useful for detecting one or more specific SNPs. For example, as described in Example 1, the following SNPs have been quantitatively associated with twinning, and are thus sequences for detecting their presence are useful herein: NCBI ID Nos.: ss38323359, ss38323363, ss38323365, ss38323360, ss38323358, ss38323366, ss38325118, ss38323361, ss38329163, ss38324813, ss38331774, ss38323369, ss38336298, ss38335633, ss38326907, ss38336726, ss38323652, ss46526720, ss38330411, ss38332219, ss38325193, ss38335345, ss38333314, ss46526291, ss38330877, ss38336723, ss38335309, ss38333309, ss38333310, ss38333663, ss38329960, ss38330391, ss38322517, ss38323940, ss38334298, ss38332526, ss38336725, ss38328717, ss38322429, ss38331771, ss38327056, ss38336504, ss38323808, ss38335213, ss38324980, ss38330878, ss46526879, ss38331316, ss38331238, ss38328850, ss38330358, ss38322515, ss38333671, ss38328261, ss38331718, ss38324897, ss38336695, ss38331244, ss38322430, ss38328727, ss38326485, ss38324963, ss38324144, ss38332685, ss38324979, ss38324438, ss38327684, ss38329891, ss38328514, ss38328176, ss38325374, ss38328732, ss38325794, ss38336045, ss38326801, ss38323430, ss38327854, ss38334807, ss38331602, ss46526524, ss46527005, ss38329662, ss46526960, ss38324252, ss38331831, ss38327198, ss38328592, ss38322778, ss38332613, ss38330112, or ss38322851, or Affymetrix ID Nos: 351958, 346215, 352891, or 348800.

Other embodiments feature collections which comprise at least one polynucleotide useful for detecting one or more of the SNPs: rs29011599, rs29024681, rs29021155, rs29018125, NGS_38815, IGF1_SNP_2, IBISS4snp1087, BTA_146334, rs29021023, rs41643915, IGF1_SNP_3, rs29020900, 342895, 346579, 353083, 348806, 342533, 348984, 346294, 350040, 353778, 347457, 352924, or 344647.

In various embodiments of the collections or the methods below, the SNPs comprise one or more of the SNPs listed in Table A, which have been associated with likelihood of twinning with the probability of $p<0.01$.

TABLE A

SNPs Useful for Predicting Twinning

| SNP ID | Chromosome | location (Mb)* | location (bp) | Name |
|---|---|---|---|---|
| Rs29011599 | BTA23 | 39.167513 | 39167513 | rs29011599 |
| 342895 | BTA07 | 63.145607 | | rs29011411 |
| BTB_01387869 | BTA14 | 35.836 | 35836440 | BTB-01387869 |
| BTA_34389 | BTA14 | 26.825 | 26824533 | Hapmap44230-BTA-34389 |
| 346579 | Unassigned | 0.1 | | rs29021107 |
| NGS_25065 | BTA14 | 18.877 | 18876538 | ARS-BFGL-NGS-25065 |
| NGS_102351 | BTA14 | 22.604 | 22603704 | ARS-BFGL-NGS-102351 |
| 353083 | BTA01 | 32.137635 | | rs29009758 |
| NGS_28234 | BTA14 | 19.362 | 19361957 | ARS-BFGL-NGS-28234 |
| 348806 | BTA23 | 45.827007 | | rs29022783 |
| Rs29024681 | BTA06 | 79.523 | | rs29024681 |
| Rs43711280 | BTA06 | 13.334137 | 13334137 | rs43711280 |
| BTB_00553442 | BTA14 | 15.935 | 15934673 | BTB-00553442 |
| 353661 | BTA06 | 79.522733 | | rs29024685 |
| 349058 | BTA14 | 21.397893 | | rs29010470 |
| Rs29010471 | BTA14 | 19.174 | | rs29010471 |
| BTC_060018 | BTA14 | 11.023 | 11022828 | Hapmap33448-BTC-060018 |
| Rs29021155 | BTA11 | 60.655 | | rs29021155 |
| BTB_00566358 | BTA14 | 37.459 | 37458775 | BTB-00566358 |
| UA_IFASA_662 | BTA14 | 10.876 | 10875942 | UA_IFASA_6621 |
| Rs29018125 | BTA08 | 63 | 65595479 | Hapmap57239-rs29018125 |
| 345125 | BTA07 | 57.368766 | | rs29024709 |
| BTB_01640837 | BTA14 | 36.095 | 36095274 | BTB-01640837 |
| Rs43593025 | BTA09 | 36.222498 | 36222498 | rs43593025 |
| 345659 | BTA23 | 40.390349 | | rs29020409 |
| NGS_105600 | BTA14 | 11.985 | 11985274 | ARS-BFGL-NGS-105600 |
| UA_IFASA_974 | BTA14 | 16.788 | 16787645 | UA_IFASA_9744 |
| NGS_38815 | BTA14 | 32.377 | 32376943 | ARS-BFGL-NGS-38815 |
| Rs42576017 | BTA09 | 84.852484 | 84852484 | rs42576017 |
| BTB_00554463 | BTA14 | 16.523 | 16523349 | BTB-00554463 |
| 344087 | BTA08 | 58.589588 | | rs29020823 |
| BTA_35994 | BTA14 | 16.137 | 16136944 | Hapmap41517-BTA-35994 |
| Rs41257131 | BTA05 | 69.956 | | rs41257131 |
| NGS_74296 | BTA14 | 18.45 | 18450040 | ARS-BFGL-NGS-74296 |
| Rs29015331 | BTA12 | 53.142923 | 53142923 | rs29015331 |
| 350925 | BTA11 | 61.111228 | | rs29026881 |
| 351455 | BTA01 | 26.481443 | | rs29010972 |
| IGF1_SNP_2 | BTA05 | | | IGF1_SNP_2 |
| UA_IFASA_535 | BTA14 | 8.133 | 110348989 | UA-IFASA-5357 |
| NGS_32892 | BTA14 | 27.557 | 27556509 | ARS-BFGL-NGS-32892 |
| BTC_064278 | BTA14 | 10.293 | 10293409 | Hapmap23620-BTC-064278 |
| 343553 | BTA15 | 15.912146 | | rs29015662 |
| BTC_009441 | BTA14 | 9.498 | 9498495 | Hapmap27677-BTC-009441 |
| 342533 | BTA24 | 56.263923 | | rs29015105 |
| NGS_68879 | BTA14 | 20.217 | 20216880 | ARS-BFGL-NGS-68879 |
| 348984 | BTA07 | 69.93493 | | rs29012592 |
| Rs29022922 | BTA03 | 99.70654 | 99706540 | rs29022922 |
| 351863 | BTA06 | 79.685587 | | rs29018255 |
| Rs29011598 | BTA23 | 39.161007 | 39161007 | rs29011598 |
| BTA_34285 | BTA14 | 23.32 | 23320027 | Hapmap41234-BTA-34285 |
| Rs29020454 | BTA14 | 39.152227 | 39152227 | rs29020454 |
| 344240 | BTA15 | 15.914696 | | rs29015664 |
| BAC_17596 | BTA14 | 33.736 | 33735947 | ARS_BFGL_BAC_17596 |
| BTC_069412 | BTA14 | 10.768 | 10768340 | Hapmap23304-BTC-069412 |
| UA_IFASA_853 | BTA14 | 12.61 | 12609632 | UA_IFASA_8537 |
| IBISS4snp108 | BTA14 | | | IBISS4snp1087 |
| Rs29027275 | BTA07 | 60.306 | | rs29027275 |
| UA_IFASA_806 | BTA14 | 36.932 | 36931827 | UA_IFASA_8067 |
| 345940 | BTA01 | 104.426701 | | rs29016850 |
| 346294 | BTA14 | 35.942595 | | rs29012557 |
| Rs29012205 | BTA03 | 99.650394 | 111990685 | Hapmap60034-rs29012205 |
| BTB_00564573 | BTA14 | 34.474 | 34473718 | BTB-00564573 |
| Rs29014046 | BTA14 | 26.072 | 26072216 | Hapmap60213-rs29014046 |
| BTA_42171 | BTA14 | 15.515 | 15515273 | Hapmap38314-BTA-42171 |
| BTA_146334 | BTA09 | 35.45476 | 35454760 | Hapmap27597-BTA-146334 |
| 350040 | BTA06 | 41.880315 | | rs29015348 |
| 350255 | BTA12 | 43.324066 | | rs29025358 |
| BTB_00983321 | BTA14 | 36.845 | 36844856 | BTB-00983321 |
| UA_IFASA_8317 | BTA14 | 38.245 | 38245445 | UA_IFASA_8173 |
| Rs29018356 | BTA26 | 5.419816 | 5071319 | Hapmap60861-rs29018356 |
| 353778 | BTA04 | 33.77989 | | rs29010454 |
| Rs41257060 | BTA18 | 9.180167 | 9180167 | rs41257060 |

TABLE A-continued

SNPs Useful for Predicting Twinning

| SNP ID | Chromosome | location (Mb)* | location (bp) | Name |
|---|---|---|---|---|
| RS29023153 | BTA18 | 81.93884 | 5720430 | Hapmap54020-rs29023153 |
| NGS_109705 | BTA26 | 8.343595 | 8343595 | ARS-BFGL-NGS-109705 |
| BTC_058037 | BTA14 | 8.377 | 8376618 | Hapmap22733-BTC-058037 |
| 351958 | BTA14 | 35.63073 | | N/A |
| BTA_117246 | BTA14 | 20.421 | 20420773 | Hapmap50246-BTA-117246 |
| 351128 | BTA04 | 44.351856 | | rs29017408 |
| Rs41630079 | BTA23 | 22.458431 | 22458431 | rs41630079 |
| ARS_USMARC_2 | BTA14 | 14.615 | 14614797 | ARS_USMARC_20 |
| 347929 | BTA13 | 13.907594 | | rs29023434 |
| Rs41654960 | BTA06 | 13.076723 | 13076723 | rs41654960 |
| NGS_39645 | BTA22 | 41.805633 | 41805633 | ARS-BFGL-NGS-39645 |
| 343419 | Unassigned | 0.1 | | rs29019730 |
| 352477 | BTA13 | 13.90762 | | rs29023435 |
| BTC_065402 | BTA14 | 25.007 | 25006867 | Hapmap23524-BTC-065402 |
| NGS_117252 | BTA14 | 9.99 | 9990358 | ARS-BFGL-NGS-117252 |
| Rs41257406 | BTA11 | 95.986 | | rs41257406 |
| Rs41622614 | BTA14 | 39.251444 | 39251444 | rs41622614 |
| 346113 | Unassigned | 0.1 | | rs29022856 |
| 350005 | BTA02 | 24.13038 | | rs29014793 |
| Rs29021023 | BTA26 | 35.766 | | rs29021023 |
| Rs29021895 | BTA14 | 11.53 | | rs29021895 |
| 348422 | BTA18 | 11.239122 | | rs29021176 |
| NGS_112623 | BTA14 | 18.683 | 18683218 | ARS-BFGL-NGS-112623 |
| 347656 | BTA15 | 5.131999 | | rs29026137 |
| 348966 | BTA01 | 136.701531 | | rs29012088 |
| 347181 | BTA01 | 3.098043 | | rs29012841 |
| 345586 | BTA07 | 60.772232 | | rs29014932 |
| BTC_010226 | BTA14 | 11.748 | 11748067 | Hapmap23784-BTC-010226 |
| 347457 | BTA28 | 7.107731 | | rs29020955 |
| RS29011274 | BTA01 | 83.619259 | 83619259 | rs29011274 |
| Rs29010308 | BTA05 | 16.836 | 17272102 | Hapmap55237-rs29010308 |
| 352924 | BTA06 | 20.51922 | | rs29024705 |
| 352831 | BTA14 | 11.826138 | | rs29025879 |
| Rs43596422 | BTA09 | 35.670291 | 35670291 | rs43596422 |
| Rs41643915 | BTA22 | 45.735107 | 45735107 | rs41643915 |
| 345483 | BTA11 | 43.717906 | | rs29010503 |
| 343311 | BTA11 | 43.71812 | | rs29010502 |
| BTB_00555233 | BTA14 | 18.078 | 18078367 | BTB-00555233 |
| IGF1_SNP_3 | BTA05 | | | IGF1_SNP_3 |
| 344647 | BTA25 | 13.02804 | | rs29010042 |
| Rs29020019 | BTA14 | 21.191 | 21191021 | Hapmap60530-rs29020019 |
| Rs29020900 | BTA14 | 19.91 | 19910198 | Hapmap54398-rs29020900 |
| 349178 | BTA08 | 53.33558 | | rs29015209 |
| BTC_057468 | BTA14 | 8.85 | 8850017 | Hapmap30158-BTC-057468 |
| 347863 | BTA05 | 53.606067 | | rs29018610 |
| IGFBP5_SNP_1 | BTA02 | | | IGFBP5_SNP_1 |
| BTC_009295 | BTA14 | 9.265 | 9264515 | Hapmap31246-BTC-009295 |
| 354320 | BTA20 | 45.25198 | | rs29017434 |
| NGS_37911 | BTA14 | 14.274 | 14274020 | ARS-BFGL-NGS-37911 |
| 351968 | BTA01 | 24.821808 | | rs29013556 |
| 345460 | BTA25 | 12.919628 | | rs29010040 |
| NGS_36089 | BTA14 | 23.89 | 23890322 | ARS-BFGL-NGS-36089 |
| Rs29013534 | BTA26 | 41.299 | | rs29013534 |
| 354046 | BTA10 | 86.478816 | | rs29025325 |
| 342709 | Unassigned | 0.1 | | rs41256874 |
| Rs29014603 | BTA24 | 37.894 | | rs29014603 |
| Rs43151146 | BTA12 | 53.520216 | 53520216 | rs43151146 |
| BTB_01417924 | BTA14 | 22.383 | 22382726 | BTB-01417924 |
| IGF1_SNP_4 | BTA05 | | | IGF1_SNP_4 |
| NGS_95360 | BTA23 | 21.816693 | 21816693 | ARS-BFGL-NGS-95360 |
| 352758 | BTA04 | 39.4991 | | rs29027100 |
| NGS_104239 | BTA14 | 12.861 | 12860774 | ARS-BFGL-NGS-14239 |
| IGFBP2_INDEL | BTA02 | | | |
| Rs29015262 | BTA01 | 83.898922 | 83898922 | rs29015262 |
| BTA_75794 | BTA14 | 17.342 | 17342324 | BTA-75794-no-rs |
| 353440 | BTA06 | 13.627253 | | rs29013621 |
| BTA_160247 | BTA14 | 32.005 | 32004992 | Hapmap33516-BTA-160247 |
| IGFBP2_SNP_3 | BTA02 | | | IGFBP2_SNP_3 |
| Rs29010821 | BTA20 | 23.299301 | 23299301 | rs29010821 |
| 343530 | BTA06 | 15.070137 | | rs29025372 |
| 352263 | BTA05 | 58.47649 | | rs29021931 |
| Rs29013606 | BTA09 | 29.112806 | 29112806 | rs29013606 |
| IGF1_SNP_5 | BTA05 | | | IGF1_SNP_5 |
| Rs29010828 | BTA20 | 23.295081 | 23295081 | rs29010828 |
| NGS_117284 | BTA14 | 18.537 | 18537116 | ARS-BFGL-NGS-117284 |
| Rs41617651 | BTA20 | 23.756215 | 23756215 | rs41617651 |

TABLE A-continued

SNPs Useful for Predicting Twinning

| SNP ID | Chromosome | location (Mb)* | location (bp) | Name |
|---|---|---|---|---|
| 345993 | BTA11 | 46.665435 | | rs29024171 |
| IGF1_SNP_19 | BTA05 | | | IGF1_SNP_19 |
| 351743 | BTA08 | 49.45456 | | rs29016114 |
| BTC_073113 | BTA14 | 25.332 | 25332174 | Hapmap23509-BTC-073113 |

*(Mb location refers to Bovine Genome Assembly 3.1)

Many SNPs have been logged in various databases and contain identification numbers specific to those databases. Table B shows a correlation between ID numbers for various SNPs useful in the practice of the present invention.

TABLE B

| Affymetrix ID | Baylor ID | NCBI rs ID | Affymetrix ID | Baylor ID | NCBI rs ID |
|---|---|---|---|---|---|
| 347181 | BTA-01887 | rs29012841 | 351977 | BTA-00615 | rs29013769 |
| 351968 | BTA-00399 | rs29013556 | 350255 | BTA-09192 | rs29025358 |
| 351455 | BTA-03206 | rs29010972 | 353615 | BTA-09639 | rs29025797 |
| 353083 | BTA-02200 | rs29009758 | 347929 | BTA-14673 | rs29023434 |
| 345940 | BTA-11086 | rs29016850 | 352477 | BTA-14674 | rs29023435 |
| 343232 | BTA-00073 | rs29013238 | 343395 | BTA-05004 | rs29019171 |
| 343414 | BTA-05466 | rs29019625 | 349503 | BTA-10446 | rs29015999 |
| 348966 | BTA-01121 | rs29012088 | 352831 | BTA-09722 | rs29025879 |
| 352894 | BTA-11634 | rs29017393 | 349058 | BTA-02927 | rs29010470 |
| 350005 | BTA-04433 | rs29014793 | 351644 | BTA-08306 | rs29021868 |
| 346734 | BTA-09626 | rs29025784 | 351958 | IBISS4snp1088 | N/A |
| 345489 | BTA-03092 | rs29010859 | 346294 | BTA-01600 | rs29012557 |
| 344064 | BTA-05801 | rs29019957 | 342962 | BTA-06677 | rs29021035 |
| 349032 | BTA-02521 | rs29010075 | 347656 | BTA-09981 | rs29026137 |
| 352758 | BTA-07435 | rs29027100 | 346278 | BTA-01166 | rs29012133 |
| 351128 | BTA-11650 | rs29017408 | 348104 | BTA-01167 | rs29012134 |
| 344152 | BTA-08060 | rs29021627 | 343553 | BTA-10096 | rs29015662 |
| 350968 | BTA-08059 | rs29021626 | 344240 | BTA-10098 | rs29015664 |
| 343051 | BTA-11379 | rs29017141 | 349746 | IBISS4snp306 | N/A |
| 352891 | BTA-11485 | rs29017245 | 348422 | BTA-06819 | rs29021176 |
| 350649 | BTA-00799 | rs29013950 | 351009 | BTA-08826 | rs29022382 |
| 352263 | BTA-08373 | rs29021931 | 346682 | BTA-08825 | rs29022381 |
| 353440 | BTA-00465 | rs29013621 | 354320 | BTA-11676 | rs29017434 |
| 343530 | BTA-09206 | rs29025372 | 342875 | BTA-02845 | rs29010390 |
| 352924 | BTA-12755 | rs29024705 | 352801 | BTA-08873 | rs29022429 |
| 350040 | BTA-04998 | rs29015348 | 345659 | BTA-06043 | rs29020409 |
| 352302 | BTA-09550 | rs29025709 | 348806 | BTA-14016 | rs29022783 |
| 353661 | BTA-12733 | rs29024685 | 342533 | BTA-04749 | rs29015105 |
| 351863 | BTA-13293 | rs29018255 | 345460 | BTA-02486 | rs29010040 |
| 345125 | BTA-12759 | rs29024709 | 344647 | BTA-02488 | rs29010042 |
| 345586 | BTA-04573 | rs29014932 | 349617 | BTA-12782 | rs29024732 |
| 342895 | BTA-03650 | rs29011411 | 345949 | BTA-11257 | rs29017020 |
| 348984 | BTA-01635 | rs29012592 | 353888 | BTA-11258 | rs29017021 |
| 351743 | BTA-10561 | rs29016114 | 343540 | BTA-09719 | rs29025876 |
| 349178 | BTA-04855 | rs29015209 | 347457 | BTA-06596 | rs29020955 |
| 344087 | BTA-06462 | rs29020823 | 343092 | BTA-13993 | rs29018944 |
| 354046 | BTA-09159 | rs29025325 | 350252 | BTA-09108 | rs29025275 |
| 350212 | BTA-08458 | rs29022016 | 344205 | BTA-09264 | rs29025430 |
| 347686 | BTA-10474 | rs29016027 | 344809 | BTA-06209 | rs29020573 |
| 345483 | BTA-02962 | rs29010503 | 346579 | BTA-06750 | rs29021107 |
| 343311 | BTA-02961 | rs29010502 | 343419 | BTA-05571 | rs29019730 |
| 345993 | BTA-12216 | rs29024171 | 349771 | IBISS4snp767 | rs41257204 |
| 352905 | BTA-12213 | rs29024168 | 342709 | IBISS4snp425 | rs41256874 |
| 350925 | BTA-07215 | rs29026881 | 352215 | BTA-06885 | rs29021241 |
| 350642 | BTA-00616 | rs29013770 | 343032 | BTA-10318 | rs29015876 |

In one embodiment, the following table (Table C) can be used to construct a polynomial equation for predicting the association of a particular SNP or collection of SNPs with the trait of twinning, as described in Example 1.

TABLE C

Factors for predicting twinning using specific SNPs

| SNP ID | Coefficient | Std. Error | P-value | Gene |
|---|---|---|---|---|
| (Intercept) | −0.052452 | 0.050677 | 0.300962 | — |
| rs29011599 | 0.027694 | 0.006733 | 4.30e−05 | — |
| rs29024681 | 0.049162 | 0.007790 | 4.53e−10 | — |
| rs29021155 | 0.022143 | 0.006070 | 0.000281 | — |
| rs29018125 | −0.025313 | 0.005904 | 2.02e−05 | — |
| NGS_38815 | −0.050368 | 0.006401 | 1.13e−14 | — |
| IGF1_SNP_2 | 0.041562 | 0.006320 | 8.58e−11 | IGF1 |
| IBISS4snp1087 | −0.058557 | 0.007438 | 1.09e−14 | AHSG |
| BTA_146334 | 0.040993 | 0.005929 | 9.46e−12 | — |
| rs29021023 | −0.023879 | 0.007995 | 0.002903 | — |
| rs41643915 | −0.019959 | 0.006234 | 0.001418 | — |
| IGF1_SNP_3 | 0.043182 | 0.007457 | 9.97e−09 | — |
| rs29020900 | 0.024738 | 0.007881 | 0.001757 | — |
| 342895 | −0.036595 | 0.006397 | 1.48e−08 | — |
| 346579 | −0.021105 | 0.004676 | 7.30e−06 | — |
| 353083 | −0.023775 | 0.005242 | 6.61e−06 | — |
| 348806 | −0.053445 | 0.006548 | 1.23e−15 | — |
| 342533 | 0.040633 | 0.012344 | 0.001038 | — |
| 348984 | 0.022913 | 0.006718 | 0.000679 | — |
| 346294 | −0.027682 | 0.007883 | 0.000469 | — |
| 350040 | −0.031963 | 0.006259 | 4.08e−07 | — |
| 353778 | 0.030813 | 0.006404 | 1.78e−06 | — |
| 347457 | 0.049421 | 0.006018 | 8.34e−16 | — |
| 352924 | −0.044905 | 0.016661 | 0.007176 | — |
| 344647 | −0.030730 | 0.009300 | 0.000993 | — |

In a preferred embodiment, SNPs that have been further validated as described in Example 2 are particularly useful to identify with polynucleotides of the invention. These include, from Table 2-2: rs29012841, rs29013556, rs29010972, rs29009758, rs29016850, rs29012088, rs29014793, rs29010454, rs29017408, rs29010308, rs29018610, IGF1_SNP_3, IGF1_SNP_2, rs41257131, rs29024681, rs29024705, rs29015348, rs29018255, rs29024685, rs29024709, rs29014932, rs29027275, rs29011411, rs2901259, rs29015209, rs29020823, rs29018125, BTA_146334, rs29019730, rs29025325, rs29010503, rs29010502, rs29021155, rs29026881, rs41257406, rs29025358, rs29023435, rs29023434, rs29021895, rs29025879, NGS_74296, NGS_25065, rs29010471, NGS_28234, rs29020900, rs29010470, rs29014046, NGS_70865, NGS_38815, BAC_17596, BTB_005645, IBISS4snp1087, AffyID3519, rs29012557, BTB_013878, rs41622614, rs29015662, rs29021176, rs29022856, rs29020409, rs29022783, rs29015105, rs29010042, rs29010040, rs29015664, rs29021023, and rs29020955.

Following backward elimination analysis as described in Example 2, a reduced marker panel was developed (see Table 2-3), containing the following 18 SNPs: rs29010454, IGF1_SNP_2, IGF1_SNP_3, rs29015348, rs29024681, rs29012592, rs29011411, rs29020823, rs29015209, BTA_146334, rs29010503, AffyID3519, IBISS4snp1087, BTB_005645, NGS_28234, rs29015662, rs29022783 and rs29020955. This information and the other information set forth in Example 2 and Table 2-3 in particular may be used to predict an animal's genetic merit for twinning rate. For example, an animal can be genotyped for up to all 18 of the SNPs listed above, then using the coefficients of Table 2-3 corresponding to its set of genotypes, the values would be totaled to arrive at the animal's predicted twinning rate.

Still other SNPs that are useful in connection herewith include various SNPs on BTA5, particularly SNPs within the IGF1 region, or within the introns of IGF1 specifically, especially intron 2 of IGF1. For example SNP2, 5 and 19 have been found to be highly and consistently associated with twinning. In particular, the inventors have discovered that an allelic substitution of G to A in IGF SNP2 was associated with a reduction of twinning rate. The reduction was consistent across two independent data sets. Surprisingly, despite suspicions of associations, prior studies looked for, but found no significant associations between IGF1 SNPs and twinning rate. Several SNPs associated with twinning within the IGF1 gene are set forth in Table 3-5.

In addition, SNPs on bovine chromosome 5 (BTA5) associated with likelihood of twinning (see Table 3-4) include: ss38332405, ss38334594, ss38324419, ss38324418, ss38333537, ss38324813, ss46526664, 54966387, 54966493, 54977448, ss38322168, 58655362, 63551646, 63554840, 64273448, 65538715, ss46527005, ss46526677 and ss38322778.

It will be understood by the skilled artisan that the SNPs or other polymorphisms identified herein as markers of ovulation or twinning rate are associated with genomic regions associated with these traits. As such, preferred embodiments of the methods of the invention include identifying any of the SNPs exemplified herein, as well as any SNPs or polymorphisms within the same genomic region. In one embodiment, that genomic region comprises +/−10,000 bases of the identified SNP or other polymorphism. In another embodiment, the genomic region comprises +/−20,000 bases of the identified SNP or other polymorphism. In another embodiment, the genomic region comprises +/−30,000 bases of the identified SNP or other polymorphism. In another embodiment, the genomic region comprises +/−40,000 bases of the identified SNP or other polymorphism. In another embodiment, the genomic region comprises +/−50,000 bases of the identified SNP or other polymorphism. In another embodiment, the genomic region comprises +/−60,000 bases of the identified SNP or other polymorphism. In another embodiment, the genomic region comprises +/−70,000 bases of the identified SNP or other polymorphism. In another embodiment, the genomic region comprises +/−80,000 bases of the identified SNP or other polymorphism. In another embodiment, the genomic region comprises +/−90,000 bases of the identified SNP or other polymorphism. In another embodiment, the genomic region comprises +/−100,000 bases of the identified SNP or other polymorphism. In another embodiment, the genomic region comprises +/−110,000 bases of the identified SNP or other polymorphism. In another embodiment, the genomic region comprises +/−120,000 bases of the identified SNP or other polymorphism. In another embodiment, the genomic region comprises +/−130,000 bases of the identified SNP or other polymorphism. In another embodiment, the genomic region comprises +/−140,000 bases of the identified SNP or other polymorphism. In another embodiment, the genomic region comprises +/−150,000 bases of the identified SNP or other polymorphism. In another embodiment, the genomic region comprises +/−160,000 bases of the identified SNP or other polymorphism. In another embodiment, the genomic region comprises +/−170,000 bases of the identified SNP or other polymorphism. In another embodiment, the genomic region comprises +/−180,000 bases of the identified SNP or other polymorphism. In another embodiment, the genomic region comprises +/−190,000 bases of the identified SNP or other polymorphism. In another embodiment, the genomic region comprises +/−200,000 bases of the identified SNP or other polymorphism.

In another of its several aspects, the invention features methods of detecting sequences in a genome that provide an estimate of twinning probability or which have predictive value regarding twinning likelihood. In one embodiment, methods for estimating the likelihood of twinning in one or more members of a cattle population are provided. The methods generally comprise the steps of:

a) providing a collection of one or more polynucleotides, each of which is at least partially complementary to a sequence in a bovine genome, comprising or identifying at least one sequence that is quantitatively associated with twinning with statistical significance of at least $p \leq 0.01$;

b) using the collection to determine the presence or absence of sequences complementary to one or more polynucleotides from the collection in one or more members of the cattle population genome, wherein the presence or absence of the complementary sequences is quantitatively associated with the trait of twinning in a cattle population; and c) estimating the likelihood of twinning based on the results of step b).

The method, as the skilled artisan will appreciate, encompass use of collections of polynucleotides, for example, as described above, which are useful for detecting the presence or absence of sequences in a genome that are predictive of twinning. In one embodiment, the estimating step comprises a laboratory analysis. In such embodiments, the method comprises a statistical calculation. In other embodiments, the method comprises a field test. In many such embodiments, preferred tests are conveniently used to provide a threshold estimate or a visual indicator of acceptability. Preferably, no actual statistical calculation is required for such field tests. Such tests may require the use of a chart, or reader other device to provide a measurement of twinning rate, or other useful measurement or result that reflects the likelihood of twinning.

Preferably, the methods provided herein feature a collection of polynucleotides that comprises at least one sequence that is quantitatively associated with twinning with statistical significance of at least $p \leq 0.01$. In other embodiments, the collection comprises at least one sequence that is quantitatively associated with twinning with statistical significance of at least $p \leq 0.005$. Most preferred are methods wherein the collection comprises at least one sequence that is quantitatively associated with twinning with statistical significance of at least $p \leq 0.001$.

The method may involve the use of a collection comprising as few as a single polynucleotide, identifying one location on the bovine genome that predicts likelihood of ovulation or twinning. Or the method may utilize two or more polynucleotides identifying a region or location on the bovine genome associated with likelihood of ovulation or twinning. Likewise, the method may utilize a collection comprising two or more polynucleotides identifying two or more locations or regions in the bovine genome associated with likelihood of ovulation or twinning. By "two or more", is meant 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 82, 84, 85, 86, 87, 88, 89, 90, 90, 92, 93, 94, 95, 96, 97, 98, 99, 100 or more polynucleotides and/or locations or regions in the bovine genome associated with likelihood of ovulation or twinning. Even larger collections may be used, including collections comprising 110, 120, 130, 140, 150, 160, 170, 180, 190, 200 or more (or incremental numbers in between) polynucleotides and/or locations or regions in the bovine genome associated with ovulation or twinning rate.

The methods preferably are useful for estimating breeding value in cattle, thus preferably feature a collection of polynucleotides that is useful for estimating breeding value in cattle.

In various embodiments, the collection is useful for detecting the presence or absence of one allele of a SNP in the bovine genome. Preferably, at least one of the polynucleotides in the collection is complementary to a sequence located on bovine chromosome 5 (BTA5).

In certain embodiments of the methods, at least one of the polynucleotides in the collection is complementary to a sequence that maps between 55-75 Mb of BTA5, between 64-73 Mb of BTA5, or at any of 25-35 Mb, 49-51 Mb, 64 to 65 Mb, or 69-70 Mb of BTA5.

In a particular method, one or more of the polynucleotides in the collection is complementary to a sequence that maps on BTA5 between 69.2 to 69.9 Mb. Even more preferred are methods wherein at least one of the polynucleotides in the collection is complementary to a sequence located in a genomic sequence for Insulin-like Growth Factor 1 (IGF1).

In various embodiments, the method features collections of polynucleotides wherein at least one of the polynucleotides in the collection is complementary to a sequence in a genomic sequence for synapsin III (SYN3), synapsin III isoform A (SYN3A), collagen type X alpha-1 (COL10A1) precursor, eukaryotic translation initiation factor 3, subunit 7 (EIF3S7), insulin-like growth factor 1 (IGF1), inhibin beta-C (INHBC), inhibin beta-E (INHBE), cytoskeleton-associated protein 4 (CKAP4), small nuclear ribonucleoprotein polypeptide F (SNRPF), or Alpha2-HS glycoprotein (AHSG).

The method can also utilize a collection comprising at least one polynucleotide useful for detecting one or more specific SNPs. For example, as described in Example 1, the following SNPs have been quantitatively associated with twinning, and are thus sequences for detecting their presence are useful herein: NCBI ID Nos.: ss38323359, ss38323363, ss38323365, ss38323360, ss38323358, ss38323366, ss38325118, ss38323361, ss38329163, ss38324813, ss38331774, ss38323369, ss38336298, ss38335633, ss38326907, ss38336726, ss38323652, ss46526720, ss38330411, ss38332219, ss38325193, ss38335345, ss38333314, ss46526291, ss38330877, ss38336723, ss38335309, ss38333309, ss38333310, ss38333663, ss38329960, ss38330391, ss38322517, ss38323940, ss38334298, ss38332526, ss38336725, ss38328717, ss38322429, ss38331771, ss38327056, ss38336504, ss38323808, ss38335213, ss38324980, ss38330878, ss46526879, ss38331316, ss38331238, ss38328850, ss38330358, ss38322515, ss38333671, ss38328261, ss38331718, ss38324897, ss38336695, ss38331244, ss38322430, ss38328727, ss38326485, ss38324963, ss38324144, ss38332685, ss38324979, ss38324438, ss38327684, ss38329891, ss38328514, ss38328176, ss38325374, ss38328732, ss38325794, ss38336045, ss38326801, ss38323430, ss38327854, ss38334807, ss38331602, ss46526524, ss46527005, ss38329662, ss46526960, ss38324252, ss38331831, ss38327198, ss38328592, ss38322778, ss38332613, ss38330112, or ss38322851, or Affymetrix ID Nos: 351958, 346215, 352891, or 348800.

Other embodiments of the method utilize collections which comprise at least one polynucleotide useful for detecting one or more of the SNPs: rs29011599, rs29024681, rs29021155, rs29018125, NGS_38815, IGF1_SNP_2, IBISS4snp1087, BTA_146334, rs29021023, rs41643915, IGF1_SNP_3, rs29020900, 342895, 346579, 353083, 348806, 342533, 348984, 346294, 350040, 353778, 347457, 352924, or 344647.

In one embodiment of the method, the information in Table C above can be used to construct a polynomial equation for predicting the association of a particular SNP or collection of SNPs with the trait of twinning, as described in Example 1.

In a preferred embodiment, the method is used to query the bovine genome for SNPs that have been further validated as described in Example 2. These include, from Table 2-2: rs29012841, rs29013556, rs29010972, rs29009758, rs29016850, rs29012088, rs29014793, rs29010454, rs29017408, rs29010308, rs29018610, IGF1_SNP_3, IGF1_SNP_2, rs41257131, rs29024681, rs29024705, rs29015348, rs29018255, rs29024685, rs29024709, rs29014932, rs29027275, rs29011411, rs2901259, rs29015209, rs29020823, rs29018125, BTA_146334, rs29019730, rs29025325, rs29010503, rs29010502, rs29021155, rs29026881, rs41257406, rs29025358, rs29023435, rs29023434, rs29021895, rs29025879, NGS_74296, NGS_25065, rs29010471, NGS_28234, rs29020900, rs29010470, rs29014046, NGS_70865, NGS_38815, BAC_17596, BTB_005645, IBISS4snp1087, AffyID3519, rs29012557, BTB_013878, rs41622614, rs29015662, rs29021176, rs29022856, rs29020409, rs29022783, rs29015105, rs29010042, rs29010040, rs29015664, rs29021023, and rs29020955.

Following backward elimination analysis as described in Example 2, a reduced marker panel has been developed (see Table 2-3), containing the following 18 SNPs: rs29010454, IGF1_SNP_2, IGF1_SNP_3, rs29015348, rs29024681, rs29012592, rs29011411, rs29020823, rs29015209, BTA_146334, rs29010503, AffyID3519, IBISS4snp1087, BTB_005645, NGS_28234, rs29015662, rs29022783 and rs29020955. This information and the other information set forth in Example 2 and Table 2-3 in particular, may be used to predict an animal's genetic merit for twinning rate. For example, an animal can be genotyped for up to all 18 of the SNPs listed above, then using the coefficients of Table 2-3 corresponding to its set of genotypes, the values are totaled to arrive at the animal's predicted twinning rate.

Still other SNPs that are useful in these methods include various SNPs on BTA5, particularly SNPs within the IGF1 region, or within the introns of IGF1 specifically, especially intron 2 of IGF1. For example SNP2, 5 and 19 have been found to be highly and consistently associated with twinning. In particular, the inventors have discovered that an allelic substitution of G to A in IGF SNP2 was associated with a reduction of twinning rate. The reduction was consistent across two independent data sets.

In addition, SNPs on bovine chromosome 5 (BTA5) associated with likelihood of twinning (see Table 3-4) include: ss38332405, ss38334594, ss38324419, ss38324418, ss38333537, ss38324813, ss46526664, 54966387, 54966493, 54977448, ss38322168, 58655362, 63551646, 63554840, 64273448, 65538715, ss46527005, ss46526677 and ss38322778.

As mentioned above, preferred embodiments of the method of the invention involves genotyping one or more animals to detect the presence of one or more polymorphisms that can be quantitatively associated with twinning rate, or transmission of twinning rate, in the animals. In particular, the polymorphisms comprise SNPs. An exemplary embodiment utilizes the reduced marker panel and attendant information shown in Table 2-3, and the prediction equation(s) described in Example 2.

Genotyping for polymorphisms, including SNPs, is well known in the art. Numerous methods and technology platforms are commercially available to accomplish SNP genotyping, and the skilled artisan will understand which methods are most suited to the purposes described herein. Methods particularly suitable to genome-wide and more localized genotyping of animals are set forth herein in Examples 1, 2 and 3.

It will be understood by the skilled artisan that the SNPs or other polymorphisms identified herein as markers of ovulation or twinning rate are associated with genomic regions associated with these traits. As such, preferred embodiments of the methods of the invention include identifying any of the SNPs exemplified herein, as well as any SNPs or polymorphisms within the same genomic region. In one embodiment, that genomic region comprises +/−10,000 bases of the identified SNP or other polymorphism. In another embodiment, the genomic region comprises +/−20,000 bases of the identified SNP or other polymorphism. In another embodiment, the genomic region comprises +/−30,000 bases of the identified SNP or other polymorphism. In another embodiment, the genomic region comprises +/−40,000 bases of the identified SNP or other polymorphism. In another embodiment, the genomic region comprises +/−50,000 bases of the identified SNP or other polymorphism. In another embodiment, the genomic region comprises +/−60,000 bases of the identified SNP or other polymorphism. In another embodiment, the genomic region comprises +/−70,000 bases of the identified SNP or other polymorphism. In another embodiment, the genomic region comprises +/−80,000 bases of the identified SNP or other polymorphism. In another embodiment, the genomic region comprises +/−90,000 bases of the identified SNP or other polymorphism. In another embodiment, the genomic region comprises +/−100,000 bases of the identified SNP or other polymorphism. In another embodiment, the genomic region comprises +/−110,000 bases of the identified SNP or other polymorphism. In another embodiment, the genomic region comprises +/−120,000 bases of the identified SNP or other polymorphism. In another embodiment, the genomic region comprises +/−130,000 bases of the identified SNP or other polymorphism. In another embodiment, the genomic region comprises +/−140,000 bases of the identified SNP or other polymorphism. In another embodiment, the genomic region comprises +/−150,000 bases of the identified SNP or other polymorphism. In another embodiment, the genomic region comprises +/−160,000 bases of the identified SNP or other polymorphism. In another embodiment, the genomic region comprises +/−170,000 bases of the identified SNP or other polymorphism. In another embodiment, the genomic region comprises +/−180,000 bases of the identified SNP or other polymorphism. In another embodiment, the genomic region comprises +/−190,000 bases of the identified SNP or other polymorphism. In another embodiment, the genomic region comprises +/−200,000 bases of the identified SNP or other polymorphism.

In yet another of its several aspects, the invention features kits that comprise one or more of the collections of polynucleotides useful for detecting sequences in a genome that are quantitatively associated with twinning, and instructions for use of the collection(s) for estimating breeding value or predicting the likelihood of twinning.

The kits can comprise as few as a single polynucleotide, identifying one location on the bovine genome that predicts likelihood of ovulation or twinning. Or the kits can comprise two or more polynucleotides identifying a region or location on the bovine genome associated with likelihood of ovulation or twinning. Likewise, the kits can comprise two or more polynucleotides identifying two or more locations or regions in the bovine genome associated with ovulation or twinning rate. By "two or more", is meant 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 82, 84, 85, 86, 87, 88, 89, 90, 90, 92, 93, 94, 95, 96, 97, 98, 99, 100 or more polynucleotides and/or locations or regions in the bovine genome associated with likelihood of ovulation or twinning Even larger collections may be useful, including collections comprising 110, 120, 130, 140, 150, 160, 170, 180, 190, 200 or more (or incremental numbers in between) polynucleotides and/or locations or regions in the bovine genome associated with ovulation or twinning rate.

In one embodiment the kit comprises one or more PCR primer sets for amplifying a genomic region associated with twinning rate. In another embodiment, the kit comprises comprising one or more nucleic acid probe sets that specifically bind to a genomic region comprising a SNP or other feature associated with twinning rate. The kit may further include one or more reagents for the detection or capture of such SNPs or other features, or information pertaining thereto. In one embodiment, the kit comprises a polynucleotide microarray. The kit may also include computer programs or software to perform calculations used in the various methods described herein.

The kits preferably contain polynucleotides useful for estimating breeding value in cattle. In various embodiments, the kits are useful for detecting the presence or absence of one allele of a SNP in the bovine genome. Preferably, at least one of the polynucleotides in the kit is complementary to a sequence located on bovine chromosome 5 (BTA5).

In certain embodiments, at least one of the polynucleotides in the kit is complementary to a sequence that maps between 55-75 Mb of BTA5, between 64-73 Mb of BTA5, or at any of 25-35 Mb, 49-51 Mb, 64 to 65 Mb, or 69-70 Mb of BTA5.

In certain embodiments, the kit may contain one or more polynucleotides complementary to a sequence that maps on BTA5 between 69.2 to 69.9 Mb. Even more preferred are kits in which at least one of the polynucleotides is complementary to a sequence located in a genomic sequence for Insulin-like Growth Factor 1 (IGF1).

In various embodiments, the kits comprise polynucleotides wherein at least one is complementary to a sequence in a genomic sequence for synapsin III (SYN3), synapsin III isoform A (SYN3A), collagen type X alpha-1 (COL10A1) precursor, eukaryotic translation initiation factor 3, subunit 7 (EIF3S7), insulin-like growth factor 1 (IGF1), inhibin beta-C (INHBC), inhibin beta-E (INHBE), cytoskeleton-associated protein 4 (CKAP4), small nuclear ribonucleoprotein polypeptide F (SNRPF), or Alpha2-HS glycoprotein (AHSG).

The kits can also comprise at least one polynucleotide useful for detecting one or more specific SNPs. For example, as described in Example 1, the following SNPs have been quantitatively associated with twinning, and are thus sequences for detecting their presence are useful herein: NCBI ID Nos.: ss38323359, ss38323363, ss38323365, ss38323360, ss38323358, ss38323366, ss38325118, ss38323361, ss38329163, ss38324813, ss38331774, ss38323369, ss38336298, ss38335633, ss38326907, ss38336726, ss38323652, ss46526720, ss38330411, ss38332219, ss38325193, ss38335345, ss38333314, ss46526291, ss38330877, ss38336723, ss38335309, ss38333309, ss38333310, ss38333663, ss38329960, ss38330391, ss38322517, ss38323940, ss38334298, ss38332526, ss38336725, ss38328717, ss38322429, ss38331771, ss38327056, ss38336504, ss38323808, ss38335213, ss38324980, ss38330878, ss46526879, ss38331316, ss38331238, ss38328850, ss38330358, ss38322515, ss38333671, ss38328261, ss38331718, ss38324897, ss38336695, ss38331244, ss38322430, ss38328727, ss38326485, ss38324963, ss38324144, ss38332685, ss38324979, ss38324438, ss38327684, ss38329891, ss38328514, ss38328176, ss38325374, ss38328732, ss38325794, ss38336045, ss38326801, ss38323430, ss38327854, ss38334807, ss38331602, ss46526524, ss46527005, ss38329662, ss46526960, ss38324252, ss38331831, ss38327198, ss38328592, ss38322778, ss38332613, ss38330112, or ss38322851, or Affymetrix ID Nos: 351958, 346215, 352891, or 348800.

Other embodiments feature kits comprising at least one polynucleotide useful for detecting one or more of the SNPs: rs29011599, rs29024681, rs29021155, rs29018125, NGS_38815, IGF1_SNP_2, IBISS4snp1087, BTA_146334, rs29021023, rs41643915, IGF1_SNP_3, rs29020900, 342895, 346579, 353083, 348806, 342533, 348984, 346294, 350040, 353778, 347457, 352924, or 344647.

In one embodiment, the information in Table C above can be used to construct a polynomial equation for predicting the association of a particular SNP or collection of SNPs with the trait of twinning, as described in Example 1. Kits comprising polynucleotides comprising or identifying such SNPs may be assembled.

In a preferred embodiment, the kits are used in a method to query the bovine genome for SNPs that have been further validated as described in Example 2. These include, from Table 2-2: rs29012841, rs29013556, rs29010972, rs29009758, rs29016850, rs29012088, rs29014793, rs29010454, rs29017408, rs29010308, rs29018610, IGF1_SNP_3, IGF1_SNP_2, rs41257131, rs29024681, rs29024705, rs29015348, rs29018255, rs29024685, rs29024709, rs29014932, rs29027275, rs29011411, rs2901259, rs29015209, rs29020823, rs29018125, BTA_146334, rs29019730, rs29025325, rs29010503, rs29010502, rs29021155, rs29026881, rs41257406, rs29025358, rs29023435, rs29023434, rs29021895, rs29025879, NGS_74296, NGS_25065, rs29010471, NGS_28234, rs29020900, rs29010470, rs29014046, NGS_70865, NGS_38815, BAC_17596, BTB_005645, IBISS4snp1087, AffyID3519, rs29012557, BTB_013878, rs41622614, rs29015662, rs29021176, rs29022856, rs29020409, rs29022783, rs29015105, rs29010042, rs29010040, rs29015664, rs29021023, and rs29020955.

Following backward elimination analysis as described in Example 2, a reduced marker panel has been developed (see Table 2-3), containing the following 18 SNPs: rs29010454, IGF1_SNP_2, IGF1_SNP_3, rs29015348, rs29024681, rs29012592, rs29011411, rs29020823, rs29015209, BTA_146334, rs29010503, AffyID3519, IBISS4snp1087, BTB_005645, NGS_28234, rs29015662, rs29022783 and rs29020955. This information and the other information set forth in Example 2 and Table 2-3 in particular, may be used to predict an animal's genetic merit for twinning rate. For example, an animal can be genotyped for up to all 18 of the SNPs listed above, then using the coefficients of Table 2-3 corresponding to its set of genotypes, the values are totaled to arrive at the animal's predicted twinning rate. Kits comprising polynucleotides and other reagents useful for identifying these genomic regions may be constructed.

Still other SNPs that are useful for constructing kits include various SNPs on BTA5, particularly SNPs within the IGF1 region, or within the introns of IGF1 specifically, especially intron 2 of IGF1. For example SNP2, 5 and 19 have been found to be highly and consistently associated with twinning. In particular, the inventors have discovered that an allelic substitution of G to A in IGF SNP2 was associated with a reduction of twinning rate. The reduction was consistent across two independent data sets.

In addition, SNPs on bovine chromosome 5 (BTA5) associated with likelihood of twinning (see Table 3-4) include: ss38332405, ss38334594, ss38324419, ss38324418, ss38333537, ss38324813, ss46526664, 54966387, 54966493, 54977448, ss38322168, 58655362, 63551646, 63554840, 64273448, 65538715, ss46527005, ss46526677 and ss38322778.

EXAMPLES

The invention can be further illustrated by the following examples, although it will be understood that these examples included merely for purposes of illustrating and better describing certain aspects of what is disclosed herein. The examples do not limit the scope of the invention unless otherwise specifically indicated.

Example 1

Single marker association with twinning rate was tested across the entire genome in the North American Holstein population. The results of the single marker association tests were also compared with the results of QTL analysis from linkage mapping and linkage disequilibrium mapping.

The number of SNPs required for a genome-wide scan using association tests and linkage combined with linkage disequilibrium (LLD) were estimated based on the linkage disequilibrium pattern observed in the North American Holstein population.

Materials and Methods:

All animals used in this study were registered Holstein bulls from the United States and Canada. The sons used were from 19 paternal-half sib families and were chosen for having twinning rate predicted transmitting ability (PTA, Johanson et al. 2001) of high accuracy and values in the upper and lower tails for the distribution within family if there were more than approximately 30 sons in a family. Mean and median number of daughter records per sire, for calculation of PTAs, were 1071 and 513, respectively. In addition, sons were selected for balanced representation of maternal grandsires within family. Three extended families consisted of two, four, and seven half-sib families, extending to two, three, and four generations, respectively. The other families were one generation half-sib families.

DNA was extracted from semen samples using a modified phenol-chloroform extraction protocol as previously described (Cruickshank et al. 2004). The Affymetrix Bovine 10k SNP panel (Affymetrix. Calif.) was used to genotype 233 bulls. Thirty-three of the 233 failed in genotyping. Of the remaining samples, sixty-eight were provided as whole-genome amplified DNA using the GenomiPhi kit (Amersham Biosciences, Piscataway, N.J.) and all others were provided as genomic DNA. A total of 9,910 SNP markers obtained from the bovine genome sequencing project were typed. These SNPs were selected from across the genome considering genomic distribution and minor allele frequency (MAF). Eight percent of selected SNPs existed within exons and 60% were located within 50 kb upstream or downstream of genes. Genotypes were tested for Hardy-Weinberg equilibrium to identify possible typing errors.

Marker Map Construction:

Linkage analysis was performed using CRIMAP 2.4 (Green et al. 2004). Physical locations of SNP markers were available from genomic assembly v3.1. If the location of a marker based on linkage mapping was different (>30 cM) from its expected position, based on physical genomic information, it was considered as a genome assembly error or a genotyping error. Those SNPs were excluded for association tests and LLD analysis. Double recombinations between closely-linked loci (<5 cM) were considered as genotyping errors. This type of genotyping error detected as departures from Mendelian inheritance were treated as missing data.

Haplotype Construction:

Haplotypes were constructed using information on partial haplotypes inherited from sires, as well as linkage distance between closely-linked markers. This method extended minimization of recombination to include all informative markers in offspring (Windig and Meuwissen, 2004). The most probable paternally inherited haplotype of offspring in each half-sib family was obtained using the chrompic option of CRIMAP. Paternal haplotype of each half-sib was inferred using paternally-inherited alleles and linkage phase in offspring inferred by CRIMAP. After the paternal allele was identified, the other allele was deduced as the maternally-inherited allele in offspring. This procedure was implemented using a perl script.

Genome-Wide Association Tests:

To reduce false-positive errors, 6,154 markers along 8,483 physically-mapped SNPs were selected for testing twinning rate association, based on having a genotype call rate greater than 80% and a minor allele frequency greater than 5%. Association between a marker locus and twinning rate PTA was evaluated with a model including effects of sire and SNP genotype. A weighted least square analysis was performed using the known error variance structure obtained from the PTA prediction error variance (PEV).

Statistical thresholds for a genome-wide search were determined, accounting for multiple comparisons. To decide the threshold level for a genome-wide scan, an analytical method proposed by Lander and Kruglyak (1995) was used. The genome-wide significance level corresponding to exceeding threshold (T) is calculated using $\mu(T)=[C+2\rho GT^2]\alpha(T)$, where C is the number of chromosomes, $\rho$ is the expected rate of recombination per Morgan, G is the genome length in Morgans, and $\alpha(T)$ is the point-wise significance level of exceeding level T. For LLD and association tests, is two, considering within-family and historical recombinations. C is 30 and G is 30. Comparison-wise error rates (CWER) of $2.3\times10^{-5}$ and $7.2\times10^{-4}$ yielded experiment-wise error rates corresponding to the significant and suggestive levels. For linkage QTL threshold, significant ($p=5.0\times10^{-5}$) and suggestive level ($p=0.002$) were calculated with $\rho=1$.

Linkage disequilibrium between markers was measured to evaluate genome coverage of single marker association tests using the Affymetrix bovine 10K SNP panel (Affymetrix, Calif.). LD was calculated with all pairs of SNPs within a 10 Mb genomic region of the same chromosome. Pairwise $r^2>0.5$ between SNPs within 500 kb on autosomal chromosomes was considered as the threshold for estimating the genomic region captured by tag SNPs, which were representative of adjacent SNPs. SNPs selected for genome-wide association tests were used to estimate $r^2$. Linkage disequilibrium was analyzed using Haploview software (Barrett et al. 2004).

Linkage and Linkage Disequilibrium QTL Mapping:

The LLD analysis estimated QTL effects associated with paternal and maternal alleles after accounting for background genetic effects on twinning rate. Identity by descent (IBD) within family was estimated based on haplotype relationship within family and identity by descent probabilities of non-informative genomic regions between sire and offspring was estimated using informative flanking markers. IBD probabilities were calculated using marker haplotypes and the coalescent theory (Meuwissen and Goddard, 2001). IBD probabilities were calculated using a window of four or six markers. If a six-marker window extended greater than three Mb, the window was reduced to four markers to minimize errors in the IBD prediction by spurious LD. Polygenic linkage and linkage disequilibrium effects were estimated as random effects in the following linear model:

$$y = Zu + Wq + e$$

where: y is a vector of twinning rate PTAs; W is an incidence matrix of haplotypes relating phenotypic records to QTL alleles; Z is a diagonal incidence matrix relating individual polygenic effects to individual sons; u and q are random effects assumed to be distributed u~(0, A$\sigma_u^2$) and q~(0, G$\sigma_q^2$), where $\sigma_u^2$, and $\sigma_q^2$ are the polygenic variance and the additive QTL variance, respectively; A is the matrix explaining additive genetic relationship among animals; and G is the allele relationship (IBD) matrix between haplotypes.

Polygenic and random QTL effects were estimated using the ASReml package (Gilmour et al. 2002). The log likelihood of the data under models of linkage only or LLD was compared with that under the null hypothesis of no QTL effect at the central marker bracket of the four- or six-marker windows. Analyses were performed for all marker windows across the genome, advancing the window marker-by-marker.

Simulation to Evaluate Predictive Accuracy of Model:

A simulation was used to evaluate accuracy of identity by descent prediction between two haplotypes in a population representing that used here, i.e., corresponding SNP density and linkage disequilibrium pattern. A population of 1,000 animals obtained from random selection and mating of 100 males and 100 females ($N_e$=200) was simulated for 300 generations. Simulation conditions were chosen based on producing an LD pattern corresponding to that observed here for the North American dairy cattle population. A window size of 0.2-2.0 Mb consisting of a biallelic QTL locus located in the center of six evenly-spaced SNP markers was simulated to estimate IBD probability of the biallelic locus at the middle of the six-marker window. All loci were set in complete LD in the founder population with the two haplotypes having equal frequencies. In the final population, 100 haplotypes from different individuals were randomly sampled to calculate IBD probability of the QTL. To evaluate accuracy of IBD prediction, an average of the absolute difference between predicted IBD probability and true IBD probability was calculated using 100 replications. Linkage disequilibrium ($r^2$) was measured in the sampled population. Linkage map distance was approximated so that 1 Mb was equivalent to 1 cM. This simulation was implemented using R (www.r-project.org).

Results:

Genotypes for Genome-Wide Scan:

The results of the SNP screening selection process are summarized in Table 1-1. Ninety SNP markers that deviated from the Hardy-Weinberg equilibrium (HWE) were considered as genotyping error (p<0.001). Linkage analysis was used to identify SNPs that were positioned incorrectly. Compared to bovine genome assembly 3.1, the genomic position of 295 autosomal SNPs deviated more than 30 Mb from the position inferred by linkage mapping based on the assumption that 1 cM was equivalent to 1 Mb. This was less than 5% of SNPs selected for linkage analysis. The percentage of non-Mendelian inheritance errors in genotypes was less than 0.5% of the total genotypes. Although marker loci were not evenly distributed across the genome, mean and median of interval distance between adjacent loci selected for the genome-wide scan was 0.31 Mb and 0.22 Mb on the bovine genome assembly 3.1. Total size of the bovine genome assembly 3.1 was approximately 2,400 Mb. Of 7,146 SNPs selected for the genome wide scan, 1,964 SNPs were located within 50 kb upstream or downstream of genes and 2,667 SNPs existed within known genes. The remaining SNPs (2,515) were located in intergenic regions. According to the available genomic annotation of databases at the National Center for Biotechnology Information (NCBI) (url is ncbi.nlm.nih.gov/mapview) over 20,000 genes were annotated on the bovine genome assembly 3.1 using transcribed sequences, known sequence from other species, or bioinformatics gene prediction tools.

TABLE 1-1

Summary of SNP markers selection.

| SNP screening method | Selected SNPs | Eliminated SNPs |
|---|---|---|
| Original genotypes | 9,919 | — |
| Physically mapped in genome assembly 3.1 | 8,433 | 1,436 |
| Genotyping success rate > 80% | 8,018 | 465 |
| Hardy-Weinberg equilibrium test (p < 0.001) | 7,928 | 90 |
| Heterozygous in at least one sire (for linkage analysis) | 7,492 | 436 |
| Incorrect locus order or Mendelian segregation errors (selection for LLD) | 7,146 | 346 |
| Minor allele exists in two or more half-sib families & minor allele frequency > 5% (selection for marker association test) | 6,454 | 809 |

Coverage Evaluation by Linkage Disequilibrium:

Linkage disequilibrium (LD) ($r^2$) was measured between pairs of closely positioned loci across the bovine genome. Linkage disequilibrium was evaluated for 14,140 SNP pairs within 500 kb of each other. Mean and median $r^2$ between all SNP pairs within 500 kb were 0.28 and 0.09. The mean genomic distance between marker pairs was 22.5 kb at a threshold of $r^2$>0.5. This distance decreased to 6.5 kb at $r^2$>0.8. On the simplified assumption that a SNP captures the variation of other SNPs associated at $r^2$>0.5, coverage with the 6,545 SNPs used in the association testing was approximately 150-300 Mb of the bovine genome at the $r^2$=0.5 threshold. When $r^2$=0.2 was used as a threshold of LD, the mean distance between two loci was 73.3 kb. LD was weak ($r^2$<0.1) when the genomic distance between two markers was over 100 kb. LD of few marker pairs (<0.5%) extended up to 500 kb at the $r^2$=0.5 threshold.

Single Marker-Phenotype Association Test:

The genome-wide scan detected potential association between markers and twinning rate on most chromosomes. This test produced 95 positive associations (FIG. 1) at the suggestive threshold (p<0.0007). Of the 95 SNPs associated with twinning rate, thirteen loci were associated at the significant threshold level, p<2.3×10$^{-5}$. (see Table 1-2). Significant (p<2.3×10$^{-5}$) associations were located on chromosome 2 (nine SNPs), chromosome 14 (three SNPs) and chromosome 5 (one SNP). The most significant marker association accounted for 23% of the variance in twinning rate PTA, corresponding to approximately 2% of the phenotypic variance for twinning rate.

TABLE 1-2

Genome-wide significant and suggestive single marker associations with bovine twinning rate.

| SNP ID (NCBI dbSNP) | Chromosome | Position (bp) | Significance (p) |
|---|---|---|---|
| 351958* | 14 | 35630730 | 6.1E-08 |
| ss38323359 | 2 | 102908665 | 2.6E-07 |
| ss38323363 | 2 | 102908937 | 2.7E-07 |
| 346215* | 14 | 35630276 | 3.4E-07 |
| ss38323365 | 2 | 102909009 | 3.5E-07 |
| ss38323360 | 2 | 102908818 | 5.8E-07 |
| ss38323358 | 2 | 102908604 | 1.2E-06 |
| ss38323366 | 2 | 102909120 | 2.1E-06 |
| ss38325118 | 2 | 60717386 | 1.0E-05 |
| ss38323361 | 2 | 102908874 | 1.2E-05 |
| ss38329163 | 2 | 107664703 | 1.4E-05 |
| ss38324813 | 5 | 16835901 | 1.7E-05 |
| ss38331774 | 14 | 11826138 | 2.1E-05 |
| ss38323369 | 2 | 102909189 | 3.0E-05 |
| ss38336298 | 5 | 74152696 | 3.2E-05 |
| ss38335633 | 5 | 94167125 | 3.3E-05 |
| ss38326907 | 8 | 53335580 | 3.3E-05 |
| ss38336726 | 13 | 13907620 | 3.5E-05 |
| ss38323652 | 14 | 35942595 | 3.6E-05 |
| ss46526720 | 16 | 44201685 | 3.7E-05 |
| ss38330411 | 18 | 44352521 | 3.7E-05 |
| ss38332219 | 26 | 4139063 | 3.8E-05 |
| ss38325193 | 16 | 48530530 | 4.4E-05 |
| ss38335345 | 6 | 79685587 | 5.2E-05 |
| ss38333314 | 11 | 90404790 | 5.3E-05 |
| ss46526291 | 15 | 19270036 | 7.1E-05 |
| ss38330877 | 18 | 24417031 | 7.7E-05 |
| ss38336723 | 13 | 13907157 | 8.3E-05 |
| ss38335309 | 20 | 66751407 | 8.6E-05 |
| ss38333309 | 26 | 25816607 | 8.7E-05 |
| ss38333310 | 26 | 25816776 | 8.9E-05 |
| ss38333663 | 10 | 14728252 | 9.4E-05 |
| ss38329960 | 24 | 59173205 | 9.8E-05 |
| ss38330391 | 14 | 11950458 | 1.0E-04 |
| ss38322517 | 6 | 13627253 | 1.1E-04 |
| ss38323940 | 1 | 3097998 | 1.1E-04 |
| ss38334298 | 6 | 18142242 | 1.2E-04 |
| ss38332526 | 11 | 40666353 | 1.2E-04 |
| ss38336725 | 13 | 13907594 | 1.3E-04 |
| ss38328717 | 26 | 35765651 | 1.3E-04 |
| ss38322429 | 26 | 41299476 | 1.3E-04 |
| ss38331771 | 27 | 12798363 | 1.3E-04 |
| ss38327056 | 13 | 38888532 | 1.4E-04 |
| ss38336504 | 5 | 67908996 | 1.5E-04 |
| ss38323808 | 8 | 22450832 | 1.5E-04 |
| ss38335213 | 8 | 63000355 | 1.5E-04 |
| ss38324980 | 14 | 21397838 | 1.5E-04 |
| ss38330878 | 18 | 24416870 | 1.5E-04 |
| ss46526879 | 15 | 70362925 | 1.6E-04 |
| ss38331316 | 28 | 31402223 | 1.7E-04 |
| ss38331238 | 5 | 10929300 | 1.8E-04 |
| ss38328850 | 11 | 60654721 | 1.8E-04 |
| ss38330358 | 14 | 29438577 | 1.8E-04 |
| ss38322515 | 7 | 55292134 | 1.9E-04 |
| ss38333671 | 13 | 6391027 | 2.0E-04 |
| ss38328261 | 28 | 37620053 | 2.1E-04 |
| ss38331718 | 14 | 37472909 | 2.2E-04 |
| ss38324897 | 21 | 41141313 | 2.4E-04 |
| ss38336695 | 22 | 48871417 | 2.5E-04 |
| ss38331244 | 12 | 43324066 | 2.6E-04 |
| ss38322430 | 26 | 41304563 | 2.6E-04 |
| ss38328727 | 5 | 17309229 | 2.8E-04 |
| ss38326485 | 2 | 24130380 | 2.9E-04 |
| ss38324963 | 4 | 33779890 | 3.0E-04 |
| ss38324144 | 9 | 28629530 | 3.1E-04 |
| ss38332685 | 27 | 20207785 | 3.3E-04 |
| ss38324979 | 14 | 21397893 | 3.5E-04 |

TABLE 1-2-continued

Genome-wide significant and suggestive single marker associations with bovine twinning rate.

| SNP ID (NCBI dbSNP) | Chromosome | Position (bp) | Significance (p) |
|---|---|---|---|
| ss38324438 | 10 | 61109327 | 3.8E-04 |
| ss38327684 | 5 | 62463316 | 3.9E-04 |
| ss38329891 | 27 | 21184304 | 3.9E-04 |
| ss38328514 | 8 | 58589588 | 4.1E-04 |
| ss38328176 | 20 | 52237178 | 4.1E-04 |
| ss38325374 | 4 | 52832040 | 4.2E-04 |
| ss38328732 | 8 | 99165959 | 4.2E-04 |
| 352891* | 5 | 12826659 | 4.3E-04 |
| ss38325794 | 11 | 40729983 | 4.3E-04 |
| ss38336045 | 28 | 29997007 | 4.3E-04 |
| ss38326801 | 24 | 56263923 | 4.4E-04 |
| ss38323430 | 5 | 117885058 | 4.7E-04 |
| ss38327854 | 3 | 95595378 | 4.9E-04 |
| ss38334807 | 6 | 20519220 | 5.1E-04 |
| 348800* | 2 | 70113131 | 5.2E-04 |
| ss38331602 | 6 | 42472402 | 5.2E-04 |
| ss46526524 | 1 | 138435263 | 5.4E-04 |
| ss46527005 | 5 | 69688243 | 5.4E-04 |
| ss38329662 | 7 | 60306431 | 5.7E-04 |
| ss46526960 | 11 | 95986323 | 5.7E-04 |
| ss38324252 | 1 | 32137635 | 5.8E-04 |
| ss38331831 | 8 | 63904909 | 5.8E-04 |
| ss38327198 | 11 | 98893419 | 5.8E-04 |
| ss38328592 | 14 | 22133626 | 5.8E-04 |
| ss38322778 | 5 | 84526473 | 6.1E-04 |
| ss38332613 | 8 | 49454560 | 6.6E-04 |
| ss38330112 | 4 | 105383388 | 6.8E-04 |
| ss38322851 | 5 | 25542789 | 6.8E-04 |

*Affymetrix Bovine GeneChip ID.

Figure 2:
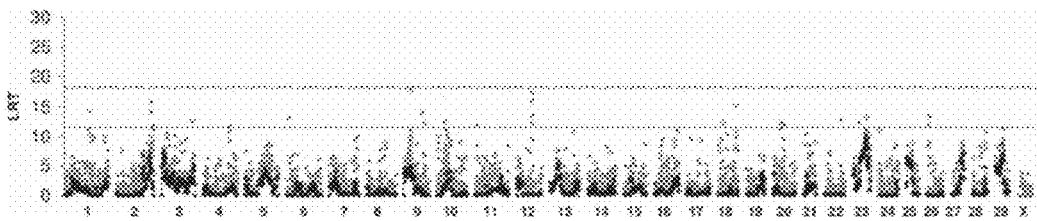
FIG. 2: Genome-wide scan using linkage combined with linkage disequilibrium. Log likelihood ratio of linkage only (dark dots) and LLD (light dots) are plotted by the center of haplotype window in sequential order by chromosome (x axis, not proportional to Mb location). Significant ($p=2.3\times10^{-5}$, solid line) and suggestive ($p=7\times10^{-4}$, dotted line) thresholds are indicated with horizontal lines.

Linkage Combined with Linkage Disequilibrium Mapping:

A total of 7,146 loci on autosomal chromosomes used in the linkage and LD scan were chosen for being informative in at least one half-sib family. Average distance between informative markers was approximately 1 Mb or 1 cM in all families. A linkage effect surpassing a suggestive level (p<0.002) was detected only on chromosome 23 (FIG. 2). The LLD scan detected 26 suggestive QTL (p<0.0007) (Table 1-3). These suggestive QTL effects were detected on fifteen chromosomes (FIG. 2). No significant (p<2.3×10$^{-5}$) QTL regions were detected across the genome. The most significant QTL was detected on chromosome 9 (p=2.5×10$^{-5}$), which was also supported by weak linkage (p<0.01).

TABLE 1.3

Genome-wide suggestive bovine twinning rate QTL using LLD.

| 3rd and 4th SNPs of six-marker window (NCBI dbSNP ID) | Chromosome | Center of six-marker window (Mb) | Six-marker window (Mb) | P-value |
|---|---|---|---|---|
| ss38330838-ss38322499 | 9 | 29.092 | 0.856 | 2.5E-05 |
| ss38322561-ss38337181 | 12 | 50.214 | 2.042* | 2.9E-05 |
| ss38325409-ss38336770 | 12 | 49.751 | 1.094 | 6.3E-05 |
| ss38332854-ss38328543 | 2 | 116.349 | 1.56 | 6.7E-05 |
| ss38332214-ss46526423 | 18 | 47.732 | 0.962 | 9.2E-05 |
| ss38325561-ss38325562 | 1 | 83.619 | 2.238* | 1.5E-04 |
| ss38323369-ss38327053 | 2 | 116.612 | 2.324 | 1.8E-04 |
| ss38331300-ss38329161 | 9 | 74.021 | 1.24 | 1.8E-04 |
| ss38325408-ss38325409 | 12 | 49.618 | 1.278 | 2.3E-04 |
| ss38323081-ss38335448 | 26 | 5.285 | 2.16 | 2.7E-04 |
| ss46526082-ss38332663 | 23 | 38.623 | 1.903 | 2.9E-04 |
| ss38330235-ss46526082 | 23 | 38.127 | 2.156 | 2.9E-04 |
| ss38322529-ss38322531 | 6 | 7.927 | 0.236 | 3.0E-04 |
| ss38325164-ss38323757 | 22 | 42.684 | 0.949 | 3.6E-04 |
| ss38336088-ss38323292 | 3 | 99.576 | 1.412 | 3.9E-04 |

TABLE 1.3-continued

Genome-wide suggestive bovine twinning rate QTL using LLD.

| 3rd and 4th SNPs of six-marker window (NCBI dbSNP ID) | Chromosome | Center of six-marker window (Mb) | Six-marker window (Mb) | P-value |
|---|---|---|---|---|
| ss38330033-ss38330031 | 10 | 21.292 | 0.823 | 4.1E−04 |
| ss38330766-ss38330767 | 9 | 80.493 | 0.941 | 4.6E−04 |
| ss38335585-ss38335584 | 20 | 23.445 | 0.351 | 4.6E−04 |
| ss38336442-ss38325081 | 18 | 8.206 | 0.755* | 4.6E−04 |
| ss38336770-ss38322561 | 12 | 49.941 | 2.365 | 4.7E−04 |
| ss38322389-ss38322388 | 23 | 17.256 | 0.135* | 4.7E−04 |
| ss38322510-ss38322328 | 11 | 2.615 | 2.454 | 5.2E−04 |
| ss38335045-ss38335044 | 26 | 3.838 | 0.807 | 5.3E−04 |
| ss38335623-ss46526297 | 20 | 35.674 | 0.871 | 5.6E−04 |
| ss38331067-ss46526233 | 2 | 124.49 | 1.365 | 6.0E−04 |
| ss38324775-ss46526399 | 4 | 94.348 | 1.608 | 6.2E−04 |

* Four-marker window size (six-marker size > 2.5 Mb)

Figure 3:
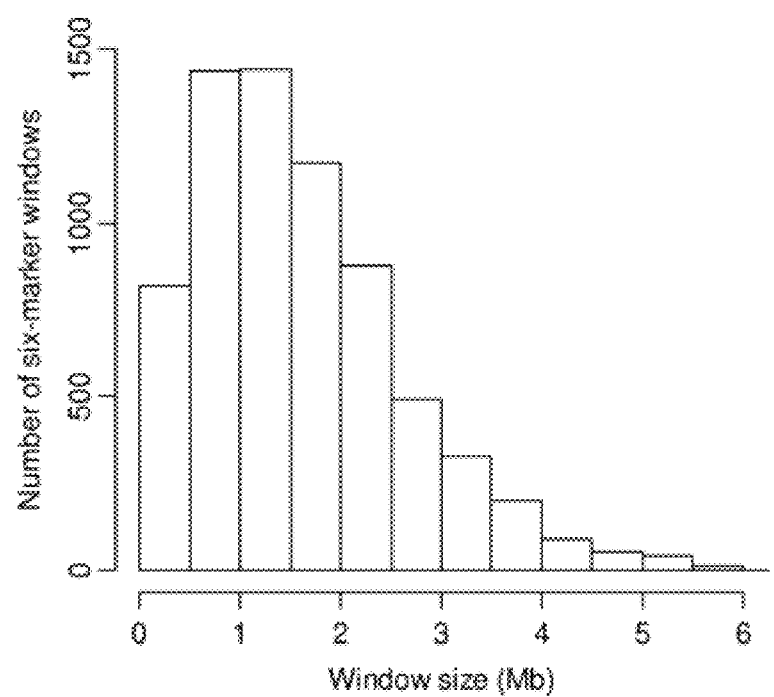
FIG. 3. Distribution of six-marker windows by physical size. The distribution is shown for distances spanned by six-marker windows across the genome. Bin size was 500 kb.

Accuracy of IBD Prediction:

The marker density of the genomic regions was considered in deciding numbers of markers (four or six) in each window for estimating IBD. Distribution of six-marker window size is shown in FIG. 3. The mean and median of six-marker windows were 2.58 Mb and 1.42 Mb, respectively. For six-marker windows extending over 1 Mb, an average LD between adjacent marker pairs within the same bracket was $r^2<0.1$.

Table 1-4 shows the relationship between accuracy of IBD estimation and LD using simulated data. The simulation was performed with four different marker spacings with six markers located within 0.2, 0.5, 1.0, or 2.0 cM. The number of generations used was 300. The marker spacing and number of generations were selected to obtain a LD pattern similar to the typical breakage of LD observed using six-marker brackets across the bovine genome in this study. The mean error of IBD prediction using 6 marker windows, calculated as mean absolute value of the difference between true (IBD=0 or 1) and predicted identity by decent probability was lower than 0.15, for LD of $r^2>0.6$. As LD decayed to $r^2$ in the range of 0.3 to 0.1, the error of IBD prediction increased to 0.25-0.3 (Table 1-3).

TABLE 1-4

Linkage disequilibrium, linkage map distance and error in IBD prediction.

| Size of six-marker windows (cM/M b) | Mean LD ($r^2$) (±s.d.)[1] | Average deviation from true IBD (±s.d.)[2] |
|---|---|---|
| 0.2 | 0.671 (±0.016) | 0.136 (±0.025) |
| 0.5 | (0.369 (±0.017) | 0.227 (±0.020) |
| 1.0 | 0.139 (±0.013) | 0.319 (±0.017) |
| 2.0 | 0.021 (±0.004) | 0.391 (±0.008) |

[1]LD between adjacent marker pairs within six-marker windows was used to calculate mean LD ($r^2$).
[2]An average of the absolute difference between predicted IBD probability and true IBD probability.

Comparison between association tests and LLD: To compare the methods, the genomic regions identified by single marker association tests were compared to QTL identified with LLD analysis. Of 87 SNPs associated with twinning rate at a suggestive level (p<0.0007), only one marker, on chromosome 26, was located within a four- or six-marker windows detected by LLD (p<0.0007).

Example 2

In Example 1, a genome-wide search with a moderate density 10K marker set identified many marker associations with twinning rate either through single marker analysis or combined linkage-linkage disequilibrium (haplotype) analysis. The objective of the study described in this example was to validate putative marker associations using an independent set of phenotypic data.

Figure 4:
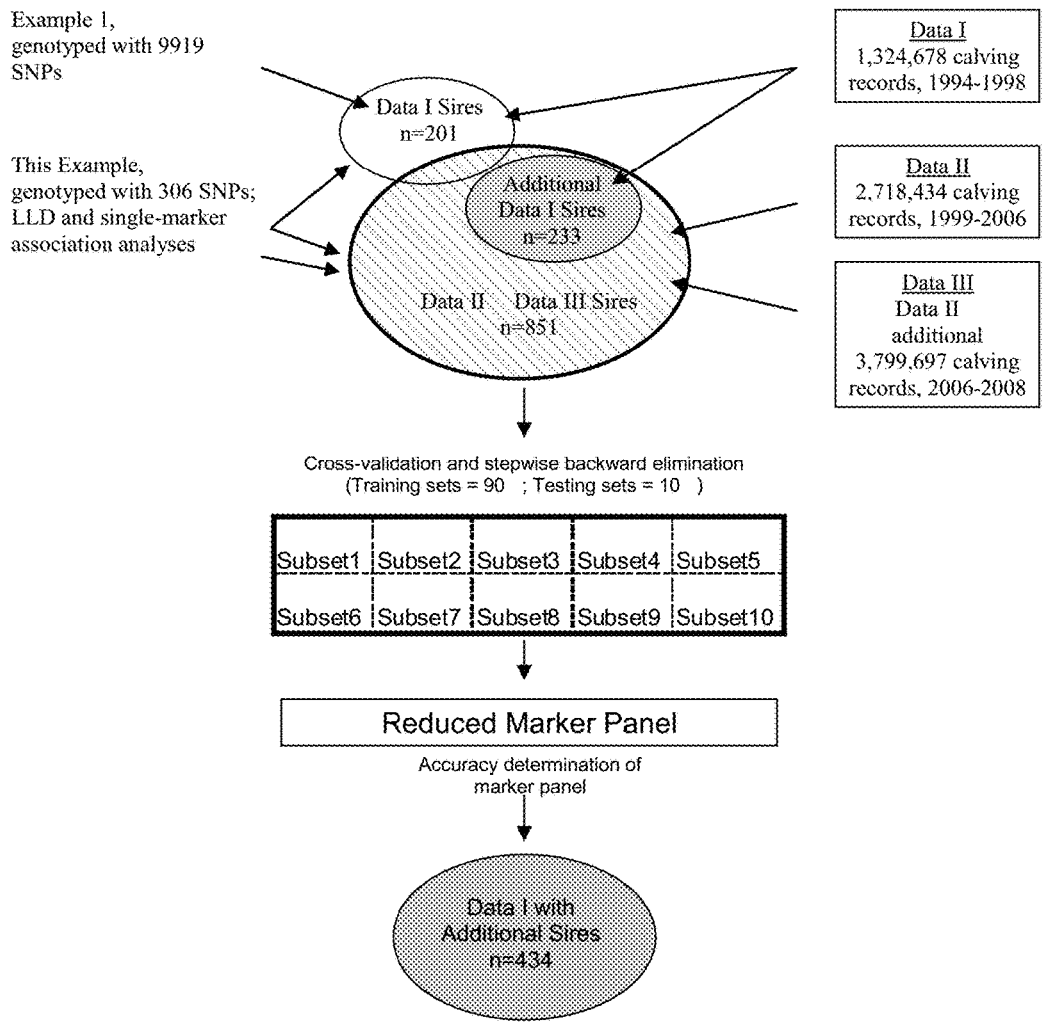
FIG. 4. Diagram describing phenotypic datasets and genotypic data generated during the progression of the study described in Example 2, which expands on Example 1. Multiple datasets were investigated as data were acquired (Data I, II, III). Cross-validation of two versions of Data III, which depended on how missing genotypes were treated, uncovered a list of SNPs for use in reduced marker panels. Ultimately, two prediction equations (M, NM), reflecting the two versions of Data III, were examined for their efficacy in predicting genetic merit for twinning rate in two versions of Data I.

Materials and Methods:

Experimental Outline:

A general layout of the study is diagramed in FIG. 4. Briefly, the current study expands on the original set forth in the previous example, but with additional sires being genotyped in the phenotypic dataset (Data I) collected from 1994 to 1998. Genotyping was also performed in an additional dataset comprised of records collected from 1999 to 2006 (Data II). Animals in Data II had minimal overlap with the animals in the original Data I. Single marker and LLD analyses were performed on Data I and Data II. Additional data subsequently became available for sires in Data II, and is referred to as Data III. A cross-validation step, followed by a stepwise backward elimination analysis, was performed on this expanded dataset. The accuracy for which the reduced marker panel was able to predict genetic merit for twinning was analyzed. Marker-predicted breeding values were compared to phenotypic values of twinning in Data I.

Data:

Animals used in this study included 921 registered Holstein bulls from 100 paternal half-sib families. Eleven pedigrees consisted of 71 half-sib families extending two or more generations. Twenty-nine pedigrees consisted of single generation pedigrees, and accounted for 11% of the total genotyped individuals. Twinning rate predicted transmitting ability scores (PTAs) were calculated using calving records from 1994 to 1998 (Data I) and 1999 to 2006 (Data II), and the underlying liability scores from threshold model analysis were used as the trait in marker association analyses (Johanson et al. 2001; see Example 1). Data I and Data II consisted of 434 and 851 bulls with twinning rate PTAs, respectively. Three hundred sixty-four bulls were in common between the two datasets. Individuals constituting Data II consisted of 11 pedigrees extending two or more generations, and 20 pedigrees extending one generation. Data I consisted of 9 pedigrees extending two or more generations, and 11 pedigrees extending one generation.

Additional calving records (from 2007-2008) subsequently became available at a later stage of the analysis. New records were added to the original data composing Data II (expanded data referred to herein as Data III). Adjusted daughter averages (Data III) were calculated for genotyped sires and consequently utilized as the phenotype in marker cross-validation analyses. Daughter averages were calculated utilizing daughter calving records adjusted for herd, parity, year, and month of calving.

The calculation of the PTA phenotype is described in detail in Johanson et al. (2001) and in the previous example. Briefly, single or twin births recorded on cows were analyzed in a model including fixed effects of parity (p), herd-year (hy), season (n), and sire group of calf (g), along with random effects of cow's sire (s) and the residual (ε).

$$y_{ijklmn} = \mu + p_i + hy_j + n_k + g_l + s_m + \varepsilon_{ijklmn}$$

The season effect included 4 levels signifying the quarter of the year in which the calves were born. Unknown sires were grouped into four groups based on birth-year quarter of the calf From the assessment of twinning rate PTAs, bulls were chosen satisfying requirements of high accuracy of prediction and PTA values in the upper and lower tails of the within-family distribution. In addition, selection accounted for maternal grandsire, intending to balance representation and avoid stratification within the sample population. During all analyses, twinning rate PTAs (Data I, Data II) were weighted by the inverse of their prediction error variance, while adjusted daughter averages (Data III) were weighted by the number of daughters of each sire.

Markers:

Markers were selected based on results from Example 1. Markers implicated in significant single-marker associations (P<0.001), as well as those located in significant LLD regions (Table 2-1), were genotyped. Additional previously ungenotyped markers were selected for genotyping. The intension for these added markers was to increase marker density of regions targeted in the LLD analysis. Therefore, relating to their past use with the data presented here, both previously genotyped and previously ungenotyped markers are incorporated in this analysis.

TABLE 2-1

LLD region descriptions.

| BTA | No. of SNPs | Start Position (Mb)+ | Region Size (Mb)+ | Average spacing (kb) | Median spacing (kb) | Average $r^2$ (*) |
|---|---|---|---|---|---|---|
| 1 | 9 | 83.61 | 5.21 | 650.66 | 281.42 | 0.184 |
| 2 | 10 | 111.93 | 1.51 | 167.54 | 182.13 | 0.300 |
| 3 | 9 | 99.80 | 4.54 | 568.10 | 393.52 | 0.206 |
| 6 | 10 | 11.29 | 1.73 | 191.72 | 206.06 | 0.327 |
| 9a | 9 | 79.74 | 3.09 | 440.97 | 278.66 | 0.287 |
| 9b | 8 | 33.62 | 1.62 | 202.13 | 174.98 | 0.025 |
| 12 | 12 | 51.89 | 4.79 | 435.12 | 232.48 | 0.115 |
| 18 | 10 | 6.26 | 4.48 | 498.31 | 658.74 | 0.053 |
| 20 | 10 | 21.82 | 2.06 | 228.39 | 180.24 | 0.396 |
| 22 | 11 | 40.13 | 9.95 | 995.26 | 756.98 | 0.136 |
| 23b | 9 | 17.98 | 7.36 | 818.24 | 514.38 | 0.341 |
| 23a | 10 | 39.29 | 7.06 | 882.82 | 883.16 | 0.075 |
| 26 | 12 | 4.75 | 5.34 | 485.51 | 168.09 | 0.179 |

(*) Average correlation coefficient between adjacent marker pairs.
+Megabase

DNA was extracted from semen samples using a modified phenol-chloroform extraction protocol as described previously (Cruickshank et al. 2004). Genotyping service was performed using competitive allele-specific PCR or single-base primer extension followed by mass spectrometry detection. Upon completion of marker genotyping, genotype data were subjected to both marker and sample triage. Departure from Hardy Weinberg Equilibrium (HWE) was determined, and markers were excluded from analysis if the observed frequencies were in excess of expectation based on $\chi^2$ test (P<1×10$^{-7}$). Markers having minor allele frequencies (MAF) less than 0.02 were excluded from analysis. Markers having fewer than 80% of the samples successfully genotyped were discarded. Individuals having fewer than 80% of the markers successfully genotyped were also discarded.

Based on the aforementioned criteria, the final list of markers successfully utilized in the analysis encompassed 24 markers genotyped by Sequenom Inc. (San Diego, United States), 104 markers genotyped by DNA Landmarks Inc. (Saint-Jean-sur-Richelieu, Canada), and 178 markers genotyped by Kbiosciences Inc. (Hoddesdon, United Kingdom), for a total of 306 genotyped SNP markers. Physical location of SNP markers were assigned based on the most recent build of the bovine genome assembly (build 4.0). Genome coordinates for markers residing on BTA14 were assigned based on UMD 2.0 assembly (Zimin et al. 2009) due to relocation of markers from the earlier assembly of build 4.0. Linkage disequilibrium ($r^2$) was assessed on all possible combinations of marker pairs within each chromosome segment. The HAPLOVIEW software (Barrett & Cardon 2006) was utilized for this procedure.

Linkage-Linkage Disequilibrium Tests:

The presence of QTL was evaluated utilizing a linkage (paternal inheritance) combined with linkage disequilibrium (maternal inheritance) (LLD) analysis. Haplotype information, identity by descent (IBD) probabilities, and analysis of variance modeling contributed to the evidence for or against QTL presence. Haplotypes were constructed from the pedigree and genotype data. Maternal and paternal haplotypes were predicted by simulated annealing using a Markov chain Monte Carlo (MCMC) algorithm within SIMWALK2 (Sobel & Lange 1996). Prior to haplotype determination, testing of Mendelian-inconsistent and Mendelian-consistent inheritance was performed. Individuals having a posterior mistyping probability greater than 0.10 at any locus were treated as missing genotypes for that locus (approximately 1.7% of the genotype data).

As described by Meuwissen & Goddard (2001), calculation of IBD probabilities at marker midpoints was performed. Each calculation utilized the information from a six-marker haplotype window. IBD probabilities were estimated by walking across the genomic regions of interest, interval by interval. Thirteen chromosome regions showing positive results for the presence of QTL in Example 1, were targeted (see Table 2-1 above).

The amount of variance accounted for by the polygenic, paternal and maternal QTL effects was estimated using the following model:

$$y = Z_s u_s + Z_d u_d + W_p q_p + W_m q_m + e$$

where y is a vector of twinning rate PTAs, $Z_s$ and $Z_d$ are incidence matrices relating individual polygenic effects of sire and dam to individual bulls, $W_p$ and $W_m$ are incidence matrices relating phenotypic records to paternally and maternally inherited QTL haplotype probabilities. The random effects $u_s u_d$, $q_p$ and $q_m$, were assumed to be normally distributed u~N(0, A$\sigma^2_u$) and q~N(0, G$\sigma^2_q$), where $\sigma^2_u$ and $\sigma^2_q$ are the sire/dam and additive paternal/maternal QTL variances, respectively. A signifies the paternal/maternal relationship matrices, and G signifies the IBD probability matrix between haplotypes. Polygenic and random QTL effects were estimated using the ASReml package of Gilmour (2002).

The log likelihood of the data under a LLD model with a QTL present was compared to the null hypothesis of a model excluding a QTL effect in linkage disequilibrium. The test statistic took the form of a likelihood ratio test (LRT)

$$LRT = -2((\log_e(L_s) - \log_e(L_g))$$

where $L_s$ is the likelihood of the reduced model and $L_g$ is the likelihood of the full model. The LRT follows a $\chi^2_{df=2}$ distribution under the null hypothesis of no difference between models.

Single-Marker Association Tests:

Single-marker associations were analyzed in a weighted least squares regression approach. Twinning rate PTAs were weighted by the inverse of their prediction error variance (PEV) and analyzed for significant association with SNP genotype using a model which included the genotype code (0, 1, or 2 copies of allele 1 present) and sire effect acquired from pedigree. Statistical threshold levels suitable for a replication study (P<0.01) as proposed by Lander & Kruglyak (1995) were used in this validation.

Cross-Validation:

As is the case with most statistical software applications, observations are eliminated from a dataset if they have missing data for any fixed effect within the analysis model. This phenomenon occurred while performing the backward elimination analysis with multiple markers. Therefore, missing genotypes were predicted. In the creation of a new version if Data III referred to herein as NM, missing values were reassigned with the most frequent genotype as indicated by the population genotypic frequencies within Data II. The RandomForest package within the statistical software R (URL at R-project.org/) was utilized to create the missing genotype transformation.

A conservative panel of markers for use in the final prediction equation may be chosen through cross-validation. Secondarily, efficacy of prediction equations may be tested on data subsets through cross-validations. To achieve this, Data III was broken down into ten data subsets (one-tenth in size to Data III). Subsets were created by random sampling within family without replacement from Data III (i.e. family structure maintained as much as possible within data subsets). Nine data subsets were combined to create a training dataset nine-tenths the original size of Data III for model development. The remaining one-tenth constituted a testing dataset for assessment of model efficacy. This was repeated 10 times, subsequently combining all possible combinations of data subsets into training and testing datasets. A generalized linear model (PROC GLM) was utilized in a stepwise backward elimination approach with SAS statistical analysis software (SAS Institute Inc., Cary, N.C.) on each training dataset with the purpose of identifying a reduced panel of markers for use in predicting genomic breeding values. Markers whose association tests passed validation criterion were available for entry into the model. Markers were allowed to remain in the model providing the significance level remained below threshold (P<0.001).

Prediction Equations:

Genotype coefficients were determined for markers remaining in the reduced marker panel from each training set (i.e. 1 reduced panel from each of 10 training sets) using a GLM model (SAS Institute Inc., Cary, N.C.). Marker-predicted adjusted daughter averages were calculated in each testing subset utilizing the genotype coefficients derived from the training set. Weighted Pearson correlation coefficients were calculated between true and marker-predicted adjusted daughter averages in each testing subset.

A final reduced marker panel was constructed after stepwise backward elimination analysis of the 10 training datasets. Markers represented at high frequency (i.e., in half or more) were chosen for inclusion in this panel. Marker genotype coefficients were then determined utilizing the entire Data III. These markers and their coefficients formed the final prediction equation which was later applied in Data I to predict genomic breeding values. Weighted correlations of marker-predicted adjusted daughter averages with true adjusted and true unadjusted daughter averages and PTAs was performed to determine accuracy of the final reduced marker panel. Lastly, markers chosen for the final reduced marker panel were checked for their association with other dairy production traits. The same model as described in the single marker association analyses for twinning rate was used. Available production traits included daughter yield deviations for milk, protein, fat, fat percent, protein percent, and milk protein, as well as daughter deviations for somatic cell score (SCS), productive life (PL), and daughter pregnancy rate (DPR).

Results:

Triage of the genotype data resulted in 13 markers discarded for low MAF (<2%), 7 markers for departure from HWE, and one marker for having fewer successfully genotyped samples than the set threshold. Sixty-two individuals were discarded from all analyses due to having fewer successfully genotyped markers than the set threshold. An additional mistyping analysis was performed as required by SIMWALK2 software (Sobel & Lange 1996; Sobel et al. 2002) prior to haplotype estimation. In total, 2,093 genotypes were treated as missing based on having a posterior mistyping probability greater than 0.10, for a total 1.69% mistyping rate.

Genome coordinates of the original markers in each LLD region were based on build 3.1 of the bovine genome. More accurate genomic locations have been assigned during build 4.0, resulting in relocation of a few of the original markers. As a result, the spacing of a few markers at the end of the marker group was larger than desired, and is reflected in the comparison of the median and average marker spacing (Table 2-1).

TABLE 2-1

LLD region descriptions.

| BTA | No. of SNPs | Start Position (Mb)+ | Region Size (Mb)+ | Average spacing (kb) | Median spacing (kb) | Average $r^2$ (*) |
|---|---|---|---|---|---|---|
| 1 | 9 | 83.61 | 5.21 | 650.66 | 281.42 | 0.184 |
| 2 | 10 | 111.93 | 1.51 | 167.54 | 182.13 | 0.300 |
| 3 | 9 | 99.80 | 4.54 | 568.10 | 393.52 | 0.206 |
| 6 | 10 | 11.29 | 1.73 | 191.72 | 206.06 | 0.327 |
| 9a | 9 | 79.74 | 3.09 | 440.97 | 278.66 | 0.287 |
| 9b | 8 | 33.62 | 1.62 | 202.13 | 174.98 | 0.025 |
| 12 | 12 | 51.89 | 4.79 | 435.12 | 232.48 | 0.115 |
| 18 | 10 | 6.26 | 4.48 | 498.31 | 658.74 | 0.053 |
| 20 | 10 | 21.82 | 2.06 | 228.39 | 180.24 | 0.396 |
| 22 | 11 | 40.13 | 9.95 | 995.26 | 756.98 | 0.136 |
| 23b | 9 | 17.98 | 7.36 | 818.24 | 514.38 | 0.341 |
| 23a | 10 | 39.29 | 7.06 | 882.82 | 883.16 | 0.075 |
| 26 | 12 | 4.75 | 5.34 | 485.51 | 168.09 | 0.179 |

(*) Average correlation coefficient between adjacent marker pairs.
+Megabase

Linkage-Linkage Disequilibrium Testing:

Thirteen of the most significant LLD regions identified in Example 1 were selected for this phase of validation. Eight to twelve markers were genotyped in each region of interest. Marker haplotypes spanned physical distances of between 0.40-9.3 megabases (Mb) as they walked across genomic regions of interest. Chromosomal regions were analyzed in each of Data I and Data II. The criterion for validation of a LLD region to be considered validated was that the LRT was statistically significant at P<0.001 in both datasets.

Figure 5:
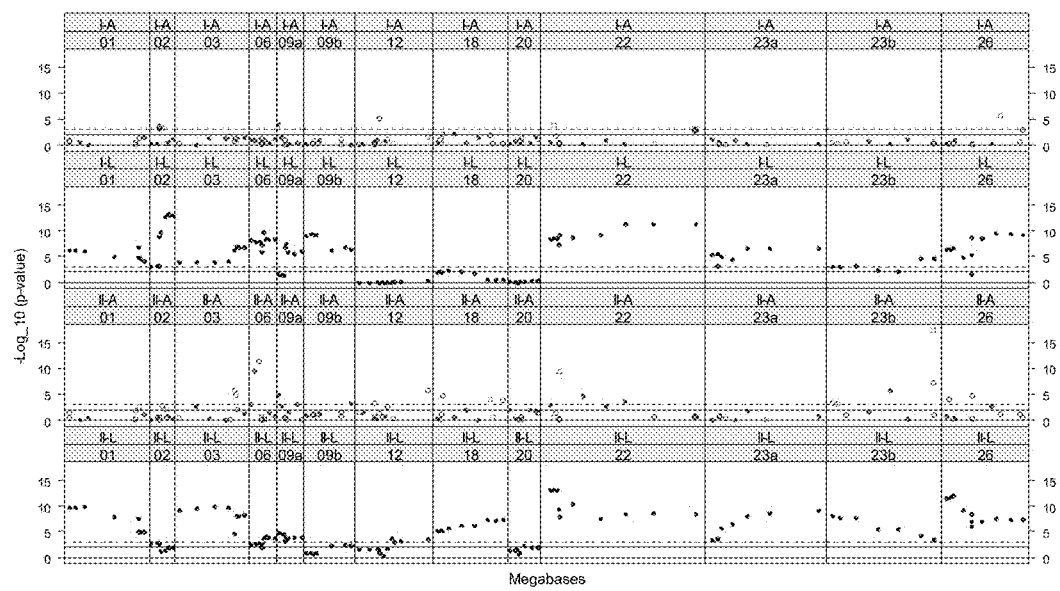
FIG. 5. Distribution of six-marker windows by physical size. Distances covered by each 6-marker haplotype during LLD analysis are binned according to size. Bin size is 500 kb.

Ten regions in both Data I and Data II showed positive results for the presence of QTL (FIG. 5). Regions on BTA12 and BTA18 showed significance in Data II, but not Data I. Regions on BTA 2 and BTA 9b showed significance in Data I, but not Data II. The eight remaining regions, corresponding to chromosomes 1, 3, 6, 9a, 22, 23(2), and 26, showed significant results at analogous locations within each region in both Data I and Data II.

Figure 6:
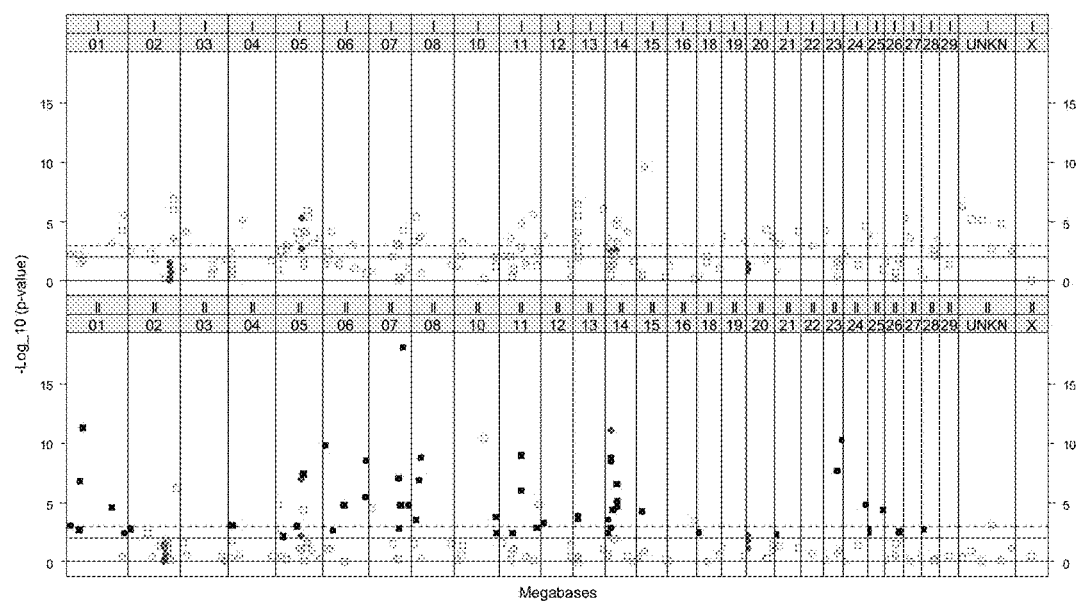
FIG. 6. LLD and association results plotted by physical location. Markers from thirteen regions were analyzed with a LLD (L) and an association (A) analysis utilizing Data I (I) and Data II (II). Regions are labeled according to chromosome and analysis. The $-\text{Log}_{10}$ P-value is plotted according to the relative location of the marker or marker interval in Mb. Solid and dashed horizontal lines indicate $-\text{Log}_{10}$ P-values of 2 and 3, respectively. For the plot of association results (-A), open circles reflect previously genotyped markers from the original significant haplotype (Example 1). Closed circles reflect markers that were added for this analysis. The closed square reflects a marker from the original haplotype that was also found significant in Example 1, and was therefore a marker slated for validation.

Single-Marker Association Testing:

Three-hundred six markers representing all bovine chromosomes but BTA17 were analyzed in the single marker association tests. The amount of marker representation on each chromosome was variable, and as expected, many marker associations surpassed the significance threshold (FIG. 5, FIG. 6). Of the previously genotyped markers analyzed, 65 and 94 were significant (P≤0.01) in Data II and Data I, respectively. For the previously ungenotyped markers tested for single-marker association, 37 and 10 markers were significant (P≤0.01) for Data II and Data I, respectively.

Agreement between single-marker association tests and LLD tests for the locations of QTL was not always consistent. Two and 18 significant single-marker associations (P<0.001) concur with the general vicinity of QTL peaks from the LLD results in each analysis of Data I and Data II, respectively. For Data I, the two significant single-marker associations were located on BTA22 and BTA26. For Data II, the 18 single-marker associations were located on BTA3, 9a, 12, 18, 22, 23b and 26. One single-marker association test was significant in both Data I and Data II, but the LLD analysis of Data I fell short of significance in that region.

Criteria necessary to be considered a validated single marker test included a significance level of P≤0.01 in Data II. In addition, phenotypic effects must have been of the same sign as had been previously discovered in the original analysis of the reduced Data I. Fifty-five markers in the previously genotyped group were validated, resulting in a 31% validation rate. A more stringent validation criterion was necessary for the marker associations in the previously ungenotyped group of markers. Twelve markers having effects of the same sign and a significance threshold surpassing P≤0.01 in both Data I and Data II were considered validated for association with twinning rate PTAs, and resulted in a 4.7% previously ungenotyped marker validation rate. Results of the marker validations are summarized in Table 2-2, where "effect" as used in the table is a regression coefficient that indicates the average change in twinning rate phenotype as one substitutes one allele for another. The phenotype in this case is twinning rate predicted transmitting ability (PTA).

TABLE 2.2

Single-marker association results for validated markers[1].

| SNP ID | Mb* | BTA | Data II | | Data I | | Status[+] |
|---|---|---|---|---|---|---|---|
| | | | Effect | −log10(P) | Effect | −log10(P) | |
| rs29012841 | 3.70 | BTA01 | −0.024 | 3.1 | −0.028 | 2.3 | PG |
| rs29013556 | 27.28 | BTA01 | 0.023 | 2.7 | 0.029 | 2.2 | PG |
| rs29010972 | 28.34 | BTA01 | 0.041 | 6.8 | 0.024 | 1.4 | PG |
| rs29009758 | 36.37 | BTA01 | −0.042 | 11.3 | −0.022 | 1.7 | PG |
| rs29016850 | 115.88 | BTA01 | 0.032 | 4.6 | 0.033 | 3.2 | PG |
| rs29012088 | 148.39 | BTA01 | 0.022 | 2.4 | 0.051 | 5.6 | PG |
| rs29014793 | 27.76 | BTA02 | −0.024 | 2.8 | −0.032 | 2.5 | PG |
| rs29010454 | 43.90 | BTA04 | −0.027 | 3.2 | −0.034 | 2.4 | PG |
| rs29017408 | 46.41 | BTA04 | 0.039 | 3.0 | 0.027 | 0.8 | PG |
| rs29010308 | 15.23 | BTA05 | 0.021 | 2.1 | 0.028 | 1.9 | PG |
| rs29018610 | 55.07 | BTA05 | −0.023 | 3.0 | −0.041 | 4.1 | PG |
| IGF1_SNP_3 | 66.79 | BTA05 | 0.024 | 2.2 | 0.039 | 2.7 | PNG |
| IGF1_SNP_2 | 66.82 | BTA05 | −0.040 | 7.0 | −0.045 | 5.3 | PNG |
| rs41257131 | 72.56 | BTA05 | 0.042 | 7.4 | 0.029 | 1.6 | PG |
| rs29024681 | 8.48 | BTA06 | −0.055 | 9.8 | −0.030 | 1.4 | PG |
| rs29024705 | 23.71 | BTA06 | −0.066 | 2.6 | −0.076 | 4.2 | PG |
| rs29015348 | 44.44 | BTA06 | −0.033 | 4.8 | −0.024 | 1.5 | PG |
| rs29018255 | 86.22 | BTA06 | 0.065 | 5.5 | 0.059 | 3.1 | PG |
| rs29024685 | 86.64 | BTA06 | 0.052 | 8.6 | 0.024 | 1.1 | PG |
| rs29024709 | 61.70 | BTA07 | −0.037 | 7.1 | −0.001 | 0.0 | PG |
| rs29014932 | 62.91 | BTA07 | 0.025 | 2.8 | 0.037 | 3.0 | PG |
| rs29027275 | 64.57 | BTA07 | −0.034 | 4.8 | −0.006 | 0.2 | PG |
| rs29011411 | 68.12 | BTA07 | −0.063 | 18.1 | −0.040 | 4.3 | PG |
| rs29012592 | 76.40 | BTA07 | −0.033 | 4.8 | −0.023 | 1.0 | PG |
| rs29015209 | 55.72 | BTA08 | −0.034 | 3.5 | −0.060 | 5.4 | PG |
| rs29020823 | 59.88 | BTA08 | −0.040 | 6.9 | −0.036 | 3.6 | PG |
| rs29018125 | 62.79 | BTA08 | −0.045 | 8.8 | −0.038 | 3.7 | PG |
| BTA_146334 | 33.62 | BTA09 | 0.032 | 4.8 | 0.041 | 3.9 | PNG |
| rs29019730 | 89.50 | BTA10 | 0.055 | 3.8 | 0.040 | 1.2 | PG |
| rs29025325 | 92.35 | BTA10 | −0.026 | 2.4 | −0.026 | 2.0 | PG |
| rs29010503 | 46.70 | BTA11 | −0.022 | 2.4 | −0.008 | 0.4 | PG |
| rs29010502 | 46.70 | BTA11 | 0.022 | 2.4 | 0.008 | 0.4 | PG |
| rs29021155 | 66.09 | BTA11 | −0.047 | 9.0 | −0.043 | 4.9 | PG |
| rs29026881 | 66.72 | BTA11 | −0.037 | 6.1 | −0.032 | 2.8 | PG |
| rs41257406 | 100.98 | BTA11 | 0.023 | 2.9 | 0.019 | 1.3 | PG |
| rs29025358 | 48.24 | BTA12 | 0.029 | 3.3 | 0.048 | 3.8 | PG |
| rs29023435 | 9.62 | BTA13 | 0.034 | 3.7 | 0.048 | 4.1 | PG |
| rs29023434 | 9.62 | BTA13 | −0.034 | 3.9 | −0.056 | 5.5 | PG |
| rs29021895 | 13.78 | BTA14 | 0.025 | 3.6 | 0.018 | 1.2 | PG |
| rs29025879 | 14.06 | BTA14 | −0.029 | 2.4 | −0.036 | 2.2 | PG |
| NGS_74296 | 20.36 | BTA14 | 0.040 | 6.6 | 0.032 | 2.4 | PNG |
| NGS_25065 | 20.73 | BTA14 | 0.052 | 11.8 | 0.047 | 4.1 | PNG |
| rs29010471 | 20.97 | BTA14 | −0.047 | 8.5 | −0.011 | 0.5 | PG |
| NGS_28234 | 21.24 | BTA14 | −0.051 | 11.1 | −0.035 | 2.5 | PNG |
| rs29020900 | 21.76 | BTA14 | 0.031 | 2.9 | 0.025 | 1.2 | PG |
| rs29010470 | 21.79 | BTA14 | 0.048 | 8.8 | 0.030 | 2.2 | PG |
| rs29014046 | 27.73 | BTA14 | −0.031 | 4.4 | −0.022 | 1.4 | PG |
| NGS_70865 | 31.98 | BTA14 | −0.027 | 2.8 | −0.046 | 4.3 | PNG |
| NGS_38815 | 34.34 | BTA14 | 0.026 | 3.6 | 0.040 | 3.6 | PNG |
| BAC_17596 | 35.00 | BTA14 | −0.036 | 4.7 | −0.041 | 3.6 | PNG |
| BTB_005645 | 35.61 | BTA14 | 0.037 | 5.1 | 0.039 | 2.6 | PNG |
| IBISS4snp1087 | 38.56 | BTA14 | 0.037 | 6.6 | 0.043 | 4.7 | PG |

TABLE 2.2-continued

Single-marker association results for validated markers[1].

| SNP ID | Mb* | BTA | Data II Effect | Data II −log10(P) | Data I Effect | Data I −log10(P) | Status[+] |
|---|---|---|---|---|---|---|---|
| AffyID3519 | 39.77 | BTA14 | −0.030 | 4.7 | −0.044 | 5.1 | PG |
| rs29012557 | 40.07 | BTA14 | 0.032 | 5.2 | 0.035 | 3.3 | PG |
| BTB_013878 | 40.24 | BTA14 | −0.058 | 13.4 | −0.037 | 2.6 | PNG |
| rs41622614 | 43.40 | BTA14 | 0.026 | 3.0 | 0.038 | 3.8 | PNG |
| rs29015662 | 23.04 | BTA15 | −0.032 | 4.3 | −0.011 | 0.5 | PG |
| rs29021176 | 13.07 | BTA18 | −0.024 | 2.5 | −0.009 | 0.4 | PG |
| rs29022856 | 41.27 | BTA21 | 0.031 | 2.3 | 0.022 | 0.7 | PG |
| rs29020409 | 42.01 | BTA23 | −0.046 | 7.7 | −0.033 | 1.6 | PG |
| rs29022783 | 51.04 | BTA23 | −0.053 | 10.3 | −0.035 | 1.9 | PG |
| rs29015105 | 56.62 | BTA24 | 0.067 | 4.9 | 0.067 | 4.6 | PG |
| rs29010042 | 12.73 | BTA25 | −0.035 | 2.8 | −0.074 | 3.9 | PG |
| rs29010040 | 12.81 | BTA25 | −0.032 | 2.5 | −0.070 | 3.7 | PG |
| rs29015664 | 23.04 | BTA25 | −0.034 | 4.4 | −0.017 | 0.9 | PG |
| rs29021023 | 37.63 | BTA26 | 0.031 | 2.5 | 0.031 | 1.8 | PG |
| rs29020955 | 8.76 | BTA28 | 0.023 | 2.7 | 0.005 | 0.2 | PG |

[+]PG = Previously genotyped (Example 1); PNG = Previously not genotyped
*Megabase
[1]All PNG markers were previously found significant in Example 1.
Sires used in the analysis of Example 1 are a subset of Data I.

Figure 7:
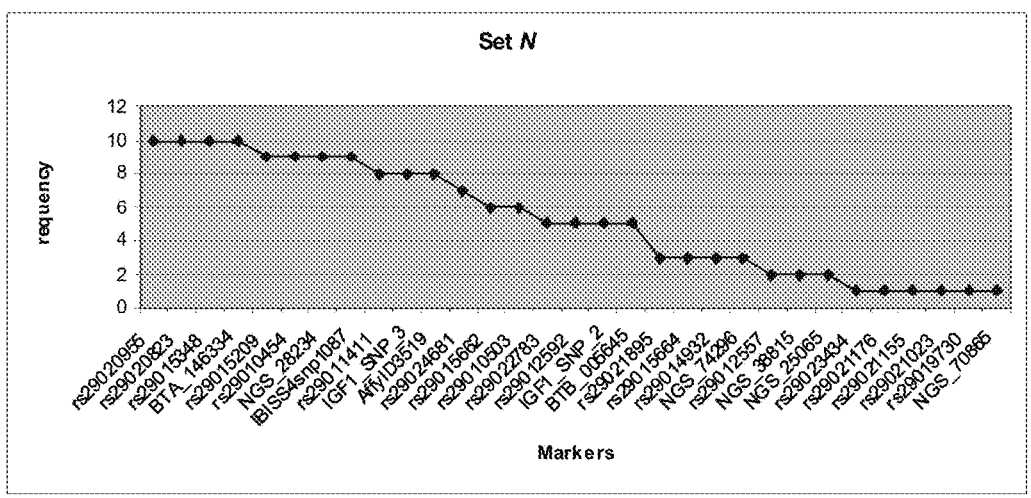
FIG. 7. Association results of markers tested for validation of Example 1 results, as well as previously ungenotyped markers. The $-\text{Log}_{10}$ P-value from Data I (I) and Data II (II) are plotted according to chromosome and Mb location (Mb location not to scale). Chromosome UNKN refers to unmapped marker loci. Solid and dashed horizontal lines indicate $-\text{Log}_{10}$ P-values of 2 and 3, respectively. Data points indicated as a filled circle reflect markers not previously genotyped. Data points indicated as a square were previously genotyped. Data points indicated as a solid square in Data II reflect markers now considered validated. They had been found significant in Example 1.

Cross-Validation:

Sixty-seven markers (Table 2-2) entered the stepwise backward elimination analysis. Markers were allowed to exit the model if their significance value failed to exceed P<0.001. As expected, the marker IDs, along with the frequency at which each marker remained in the model across the ten data subsets was variable (FIG. 7). Thirty one markers were represented at least once. Markers not remaining in the 10 reduced marker panels for the training subsets are not represented in FIG. 7. Of the markers represented at least once, frequency of representation ranged from 1 to 10, with a median representation of 5. Eighteen markers in NM attained the criteria necessary to be included in the final marker panel (Table 2-3).

Efficacy of the reduced marker panel on predicting adjusted daughter averages was compared within each of the testing subsets. As previously mentioned, the markers and subsequently the coefficients predicted for each training subset, were variable. Total number of markers remaining in the model averaged 16.4 across the ten subsets in NM. Pearson correlation coefficients between marker-predicted and adjusted daughter averages in the 10 subsets from NM were calculated. Individuals having missing genotypes assume they are genotype 3, which is set to a zero value, and were subsequently removed. The average, median, and variance for the 10 correlation values obtained in NM were 0.418, 0.458, and 0.082, respectively.

Prediction Equations:

Eighteen markers remained in the reduced marker panel. Four markers coincide near previously detected QTL peaks

TABLE 2-3

Reduced marker panel used for predicting genomic breeding values.

| Parameter | BTA | Mb | Genotypes[1] | Genotype Estimates[2] | | S.E. of estimates[2] | | Genotypic Frequency[3] | | |
|---|---|---|---|---|---|---|---|---|---|---|
| Intercept | | | | 1.046 | | 0.008 | | | | |
| rs29010454 | 4 | 43.90 | AA/AG/GG | −0.010 | −0.001 | 0.002 | 0.001 | 0.10 | 0.54 | 0.35 |
| IGF1_SNP_2 | 5 | 66.82 | AA/AG/GG | 0.008 | 0.004 | 0.002 | 0.001 | 0.26 | 0.55 | 0.19 |
| IGF1_SNP_3 | 5 | 66.79 | AA/AG/GG | 0.009 | 0.007 | 0.003 | 0.001 | 0.04 | 0.29 | 0.67 |
| rs29015348 | 6 | 44.44 | CC/CG/GG | 0.010 | 0.002 | 0.002 | 0.002 | 0.57 | 0.35 | 0.07 |
| rs29024681 | 6 | 8.48 | AA/AG/GG | 0.016 | 0.016 | 0.003 | 0.003 | 0.76 | 0.22 | 0.02 |
| rs29012592 | 7 | 76.40 | AA/AG/GG | −0.007 | −0.006 | 0.002 | 0.002 | 0.64 | 0.29 | 0.07 |
| rs29011411 | 7 | 68.12 | CC/CG/GG | 0.006 | 0.004 | 0.002 | 0.001 | 0.09 | 0.49 | 0.42 |
| rs29020823 | 8 | 59.88 | CC/CT/TT | 0.008 | 0.001 | 0.002 | 0.002 | 0.40 | 0.50 | 0.10 |
| rs29015209 | 8 | 55.72 | GG/GT/TT | 0.013 | 0.011 | 0.003 | 0.003 | 0.65 | 0.31 | 0.04 |
| BTA_146334 | 9 | 33.62 | CC/CT/TT | −0.012 | −0.006 | 0.001 | 0.001 | 0.22 | 0.56 | 0.23 |
| rs29010503 | 11 | 46.70 | AA/AG/GG | 0.003 | −0.002 | 0.002 | 0.001 | 0.27 | 0.56 | 0.16 |
| AffyID3519 | 14 | 39.77 | CC/CG/GG | −0.014 | −0.019 | 0.004 | 0.004 | 0.24 | 0.51 | 0.25 |
| IBISS4snp1087 | 14 | 38.56 | AA/AC/CC | −0.023 | −0.002 | 0.004 | 0.002 | 0.26 | 0.53 | 0.21 |
| BTB_005645 | 14 | 35.61 | AA/AG/GG | −0.011 | −0.012 | 0.003 | 0.003 | 0.65 | 0.31 | 0.04 |
| NGS_28234 | 14 | 21.24 | AA/AG/GG | 0.005 | 0.005 | 0.002 | 0.001 | 0.15 | 0.56 | 0.29 |
| rs29015662 | 15 | 23.04 | CC/CT/TT | 0.006 | 0.002 | 0.002 | 0.002 | 0.39 | 0.52 | 0.09 |
| rs29022783 | 23 | 51.04 | AA/AG/GG | 0.007 | 0.003 | 0.002 | 0.002 | 0.65 | 0.33 | 0.03 |
| rs29020955 | 28 | 8.76 | CC/CT/TT | −0.010 | −0.001 | 0.002 | 0.002 | 0.33 | 0.55 | 0.12 |

[1]Genotype categories 1 through 3 represented between hashes.
[2]Estimates (of difference in actual twinning rate among genotypes) reflect differences from the third genotype category, which is set to zero.
[3]Genotypic frequencies reflected in order of 'Genotype' category.

on BTA14 (Cobanoglu et al. 2005; Gonda et al. 2004). Two markers lie directly under the most likely position estimates from previous QTL detection on BTA5 (Cruikshank et al. 2004; Lien et al. 2000; Miewessen et al. 2002). One additional marker lays near previously detected QTL on BTA23 (Cruikshank et al. 2004). The remaining markers lie in locations not previously implicated in QTL detection, and include regions on chromosomes 4, 6, 7, 8, 9, 11, 15, and 28.

Genomic predictions of daughter averages for the bulls in Data I were calculated. Correlation of marker-predicted daughter averages with adjusted daughter averages, unadjusted daughter averages, and PTAs were 0.59, 0.14, and 0.34, respectively.

The majority of markers chosen for the reduced marker panel showed little association with dairy production traits. Marker rs29024681 located on BTA6 was significantly associated with protein percent (P<0.0001). No other marker association surpassed a significant threshold (P<0.001).

Example 3

The objectives of the study reported in this example were 1) to refine the location of the twinning or ovulation rate QTL on *Bos taurus* chromosome 5 (BTA5) as previously reported, by using a denser set of markers and a larger population along with a combined linkage-linkage disequilibrium analysis, 2) to test for evidence in the Holstein population of the QTL previously reported, and 3) to examine positional candidate genes.

Materials and Methods:

Animal Resources:

All animals used in this study were registered Holstein bulls from the United States and Canada. Twenty-five half-sib families were selected for use. Sires of the half-sib families had above average twinning rate values, as well as a moderate to large number of sons for which twinning rate predicted transmitting ability (PTA) had been calculated. A total of 358 bulls, including sires, with an average of 1,021 daughters per bull were genotyped. Two separate estimates of twinning rate predicted transmitting ability were used in analyses. The first dataset (Johanson et al., 2001; Data I) was based on daughter records obtained between 1994 and 1998, while the second dataset (Data II) used records obtained between 1998 and 2006. Twinning rate PTAs derived from Data II have not been described previously and are based on threshold model analysis of 2,718,434 Holstein calving records obtained from the Dairy Herd Improvement Association. The model for analysis of Data II included herd-year-season (with seasons January-June and July-December within each herd-year), age-parity (with up to 7 lactations and 2-mo age groups within each lactation), and sire (with relationships). A minimum of 10 calvings per herd with twinning rate >0.00% and <50% were required (mainly to eliminate herds that didn't report twinning). Overall frequency of multiple births was 4.06%. Triplets were included (coded as twins), though there were very few of these. Data I and Data II twinning rate predicted transmitting abilities were available for 342 and 291 sons, respectively. A total of 289 sons had predicted transmitting ability estimates from both data sets. Data I and Data II PTAs represent two substantially independent estimates of twinning rate phenotype for the bulls given that they are based on separate daughter records. The correlation between number of daughter records for bulls represented in both data sets was low (r=0.14). Predicted transmitting abilities of milk production, yields of protein and fat, percentages of milk protein and fat, productive life span, somatic cell score, and daughter pregnancy rate were obtained from the Animal Improvement Program Laboratory (AIPL) at USDA for examination of pleiotropic or correlated associations of candidate gene polymorphisms.

SNP Discovery:

Seventeen genes were initially targeted for SNP discovery to increase marker density in selected areas of BTA5. PCR primer pairs (Table 3-1) were designed using Primer3 software (primer3-web 0.3.0; http://primer3.sourceforge.net/) and genomic sequence information from Build 3.1 of the bovine genome sequence.

TABLE 3-1

SNP discovery: PCR primers, amplicons and polymorphisms (the number following each sequence is its SEQ ID NO)

| Gene | Primer pair | Forward primer | Reverse Primer | SNP | SNP location[1] |
|---|---|---|---|---|---|
| IFNG | 1 | TTCAACTACTCCGGCCTAACTC (1) | AGCAAGTGACTGAGTCCAAGAG (2) | A/G | 45363726 |
| IFNG | 2 | TCAGTCCTAGAGAAGTCCCTTA (3) | CTAATGAAGAACTCTGACACCC (4) | A/C | 45366254 |
| PPM1H | 1 | CCATTCCCATCTGATTTTGAGT (5) | GGGATTTTTCAAAGGACACTACA (6) | T/C | 50646545 |
| PPM1H | 1 | CCATTCCCATCTGATTTTGAGT (5) | GGGATTTTTCAAAGGACACTACA (6) | A/T | 50646565 |
| PPM1H | 2 | ACCTGTCTCTGCAATTCAAAGTC (7) | GTATTCTCCCTACACCGAAATCA (8) | none | |
| INHBE | 1 | AATGGAAACAAGATTGGGACAG (9) | TCCTTATCTGTCCTCCCACAGT (10) | none | |
| INHBE | 2 | AATGTTCCTTCCAGTGGAGTTC (11) | AAACTGTCCAAGAAGATGGGAG (12) | none | |
| INHBE | 3 | GTGATTTTTCTCTGCCCTCTCC (13) | TCTTGAAACTCCGACTGGACTG (14) | none | |
| INHBE | 4 | ATTTGGGCCGGGTCTTAAGTTC (15) | AAGCAGCAAATCCTTGAGGGAC (16) | none | |
| INHBE | 5 | CCACCTGTGAGGACAGCAAAG (17) | TACCTCAAGCTCCGTGACCAG (18) | none | |
| INHBE | 6 | GACACGTATGATGCAAGAAGGA (19) | CCATTTAAAGGCAGTGAGGAGT (20) | none | |
| INHBE | 7 | GACTCAGTACCACCAGTGTCCA (21) | TGGCTGGGGTATTTATAACCTG (22) | none | |
| INHBE | 8 | AAAAGCCTGAGGAGCCTAGTG (23) | GAGGCATTTGCTCTGAGATTG (24) | none | |

TABLE 3-1-continued

SNP discovery: PCR primers, amplicons and polymorphisms (the number following each sequence is its SEQ ID NO)

| Gene | Primer pair | Forward primer | Reverse Primer | SNP | SNP location[1] |
|---|---|---|---|---|---|
| INHBE | 9 | TCTTCTCTCCCCAGACTTTCC (25) | TGGCCTAGCAAACTAGCAAGA (26) | A/G | |
| INHBE | 9 | TCTTCTCTCCCCAGACTTTCC (25) | TGGCCTAGCAAACTAGCAAGA (26) | T/C | |
| INHBE | 10 | AGGGTACAGAGCCAGATGGATA (27) | TGCTCAATCTTCTCAAGGTCAA (28) | none | |
| INHBC | 1 | CCTTCAACTTTACCCTCATCTC (29) | CGTAGGAAGACTGAGATGACTG (29) | T/C | 54971414 |
| INHBC | 2 | TGTAAAGCCTGGAATATGGTTG (31) | GATCTTACGAAGTCTCTCTCCAC (32) | none | |
| INHBC | 3 | CTGCCCACTAAATTCTCTACCC (33) | AGCATCTTGGACAAGCTGCAC (34) | A/G | 54977605 |
| INHBC | 4 | GATGATCTCATACTCCTGTCCCTC (35) | ACATGACAATGACCTACAGTGTCC (36) | none | |
| SNRPF | 1 | GAGCATGGTCTGTTCAGGTGGTA (37) | ACTTGTCCATGCAGTTCAAACCT (38) | A/T | 58655355 |
| SNRPF | 1 | GAGCATGGTCTGTTCAGGTGGTA (37) | ACTTGTCCATGCAGTTCAAACCT (38) | A/G | 58655185 |
| SYCP3 | 1 | TGAGCACTGTTGAGATTTCCTA (39) | GGTGGGGGTAAATCTTGAATA (40) | none | |
| SYCP3 | 2 | GTGCATGAGAGGATTTTGAGGGT (41) | GGAAATCTCAACAGTGCTCAAAAC (42) | none | |
| SYCP3 | 3 | AATTCTTGAACCAGCTTTATCC (43) | AAGTCCATTTTATCTCCAAGCA (44) | none | |
| SYCP3 | 4 | GAAAATACCATGAGCAGAGGAG (45) | GCGACTAACACTTTCACATTTTC (46) | none | |
| SYCP3 | 5 | ATTTCTGTTGCTGGCAGTTTGG (47) | GAAAGTGAAGTCGCTCAGTCGT (48) | T/C | 63550351 |
| SYCP3 | 6 | AGTCCATGGGGTCGCTAAGAGTC (49) | AAAACACCCCAATAGCCGAGGA (50) | C/G | 63551475 |
| SYCP3 | 7 | AGAAATGATTCCTAACTTGCGTG (51) | TTTTTCACCATCTTCCAGAGCTT (52) | T/C | 63553463 |
| SYCP3 | 8 | CACAGATATGAGTCCCGACCCTA (53) | TGGGTGAAGGTTTCAGAGTGGT (54) | T/G | 63554668 |
| SYCP3 | 9 | ACAGGGTTGAACGTGAAATGGAG (55) | CCCATAACTCCACTCACCAAAACA (56) | A/G | 63563991 |
| SYCP3 | 9 | ACAGGGTTGAACGTGAAATGGAG (55) | CCCATAACTCCACTCACCAAAACA (56) | T/C | 63563950 |
| SYCP3 | 10 | TGGTTTTGAACTGTCGTGCTGG (57) | CAGACTGAAACCCCCAAAACTCC (58) | None | |
| IGF1 | 1 | GGGCATAGACAAGATCCTTGACTAC (59) | TGGTGATTGGCAAAGCTAGGATGTC (60) | None | |
| IGF1 | 2 | GAAATTTGATTCATGGTGTTCCCTC (61) | AATTGTCCTCAAATTCTTAGCCACC (62) | None | |
| IGF1 | 3 | GCTGCCCTAAGAATGACAATAAACC (63) | CACCTTTCATTTGATTCTGATTGCC (64) | None | |
| IGF1 | 4 | CTGAAACCACTTCTGCCACTTTACC (65) | TGATGCTTGGCACTGTAAAGTGAGG (66) | G/A | 64222602 |
| IGF1 | 5 | AAGATGCCCATCACATCCTCCT (67) | TGTGCCTTTCAGCGACTTTCAC (68) | C/T | 64271931 |
| IGF1 | 6 | GGGAATGACGTTCTGGTT (69) | AACTGGAGAGCATCCACCAA (70) | None | |
| IGF1 | 7 | GTGCCACAAGTAGCAATGTGGA (71) | GGCATGTGCATCCATTACTGACC (72) | None | |
| IGF1 | 8 | TGGAGGGTTTCCATGAACAGGT (73) | TGTGGCTCAAGTCTCCATCCTT (74) | A/G | 64273280 |
| IGF1 | 9 | ATCTGAGAACATAACTCAGCAAA (75) | AGAGGAGGTGAAAGCTTGATGG (76) | C/A | 64273948 |
| IGF1 | 10 | ATAATACCCACCCTGACCTGCT (77) | CTCAGCAATACCTATCAGTCTCTAGC (78) | None | |
| RIC8B | 1 | CTAGTACTGGGAGGCAGCAAGA (79) | GCACATGGAAAGAGAACCAACA (80) | Indef | 65538446 |
| RIC8B | 2 | CTAGTGCCCAGCACAGAGAAA (81) | TTTGAGCTGCCAAAAGAGATG (82) | T/C | 65538923 |
| RIC8B | 3 | CAGATGGCTAAATTGAATCAAC (83) | CTAGCCCCACTCTTCACTTC (84) | none | |
| RIC8B | 4 | TGTAATCAGTTTGCAAGTCTGG (85) | GAGTTGCTTAAACCAATGGGAC (86) | none | |
| RIC8B | 5 | CAACTGCCTCTCCTCAGCTAAT (87) | AGACGTGTGACCTTGGGTAAGT (88) | none | |
| RIC8B | 6 | GTAACAGTGCGTGTGAGAGGAG (89) | GCAACCTATGGACTTGATTTGA (90) | none | |
| RIC8B | 7 | TGTGCTTATGGAAGGAAGGTTT (91) | TTCTGTGCCTTTGCTTGACTAA (92) | none | |

TABLE 3-1-continued

SNP discovery: PCR primers, amplicons and polymorphisms (the number following each sequence is its SEQ ID NO)

| Gene | Primer pair | Forward primer | Reverse Primer | SNP | SNP location[1] |
|---|---|---|---|---|---|
| RIC8B | 8 | TGAAATGTGCATCAGGGTTAAG (93) | TGTGCTTTGGGCAAGAGTATTC (94) | none | |
| RIC8B | 9 | ACACCTTACTTGACCTGGAAAC (95) | CAAGCCAACCTTACATTAAGAAC (96) | A/G | 65548378 |
| RIC8B | 10 | CCGAGAAGGAAGCTCTGTAATC (97) | GCCATTCCTGCTTTTTCAATC (98) | T/C | 65549208 |
| RIC8B | 11 | GCCTCCAAATCTTAATTTTCTTCT (99) | TCCCTTAACTCTGTAGTAGGAATG (100) | none | |
| RIC8B | 12 | TCAGCACTGATCTCTCCAGTGT (101) | CCACACATTTCCAAGCTAATGA (102) | none | |
| CKAP4 | 1 | AATGGCTACAGAAAATGCACAC (103) | CAAGGGTTGTGCAAAAGTCTTC (104) | A/G | 66075291 |
| SYN3 1 | 1 | GCAAATGCAGACTGAATTGAAC (105) | TGTGTGTACATGTGGGCATAAG (106) | A/C | 69267572 |
| SYN3 1 | 1 | GCAAATGCAGACTGAATTGAAC (105) | TGTGTGTACATGTGGGCATAAG (106) | T/C | 69267450 |
| SYN3 1 | 2 | TCAGGAAGATCCCTTGGAGAG (107) | TGAGAGAGGAGTGGACACTGAG (108) | T/A | 69276158 |
| SYN3 1 | 2 | TCAGGAAGATCCCTTGGAGAG (107) | TGAGAGAGGAGTGGACACTGAG (108) | T/C | 69276119 |
| SYN3 1 | 2 | TCAGGAAGATCCCTTGGAGAG (107) | TGAGAGAGGAGTGGACACTGAG (108) | T/C | 69276059 |
| SYN3 1 | 2 | TCAGGAAGATCCCTTGGAGAG (107) | TGAGAGAGGAGTGGACACTGAG (108) | A/C | 69276054 |
| SYN3 1 | 2 | TCAGGAAGATCCCTTGGAGAG (107) | TGAGAGAGGAGTGGACACTGAG (108) | A/G | 69275918 |
| SYN3 1 | 3 | CTTGTCCATCCTCCATCCTC (109) | CAAAATCCTCAGCAAGGCAC (110) | A/G | 69280735 |
| SYN3 1 | 3 | CTTGTCCATCCTCCATCCTC (109) | CAAAATCCTCAGCAAGGCAC (110) | A/G | 69280651 |
| SYN3 1 | 3 | CTTGTCCATCCTCCATCCTC (109) | CAAAATCCTCAGCAAGGCAC (110) | A/G | 69280619 |
| SYN3 1 | 3 | CTTGTCCATCCTCCATCCTC (109) | CAAAATCCTCAGCAAGGCAC (110) | G/C | 69280597 |
| SYN3 1 | 4 | TTGGGAGTGAGTGGAAGATGAG (111) | AACCATCCCAGGGTATTTATGAG (112) | T/C | 69282937 |
| SYN3 1 | 4 | TTGGGAGTGAGTGGAAGATGAG (111) | AACCATCCCAGGGTATTTATGAG (112) | G/C | 69282931 |
| SYN3 1 | 4 | TTGGGAGTGAGTGGAAGATGAG (111) | AACCATCCCAGGGTATTTATGAG (112) | T/C | 69282905 |
| SYN3 1 | 4 | TTGGGAGTGAGTGGAAGATGAG (111) | AACCATCCCAGGGTATTTATGAG (112) | G/A | 69282758 |
| SYN3 1 | 4 | TTGGGAGTGAGTGGAAGATGAG (111) | AACCATCCCAGGGTATTTATGAG (112) | G/A | 69282744 |
| SYN3 1 | 4 | TTGGGAGTGAGTGGAAGATGAG (111) | AACCATCCCAGGGTATTTATGAG (112) | G/A | 69282695 |
| SYN3 1 | 4 | TTGGGAGTGAGTGGAAGATGAG (111) | AACCATCCCAGGGTATTTATGAG (112) | G/A | 69282646 |
| SYN3 1 | 4 | TTGGGAGTGAGTGGAAGATGAG (111) | AACCATCCCAGGGTATTTATGAG (112) | indel | 69282533 |
| SYN3 1 | 4 | TTGGGAGTGAGTGGAAGATGAG (111) | AACCATCCCAGGGTATTTATGAG (112) | T/C | 69282448 |
| SYN3 1 | 4 | TTGGGAGTGAGTGGAAGATGAG (111) | AACCATCCCAGGGTATTTATGAG (112) | G/A | 69282419 |
| SYN3a | 1 | TGGTTAACTCATGTTGCTGGTC (113) | AACAAACCCACATGCCACC (114) | T/C | 69690399 |
| SYN3a | 1 | TGGTTAACTCATGTTGCTGGTC (113) | AACAAACCCACATGCCACC (114) | A/G | 69690037 |
| SYN3a | 2 | CGTCAGCCCATCAAGTATGTAAC (115) | TTCAATAAATCCTGAGTGCCAGT (116) | none | |
| SYN3a | 3 | GGTGAATTTGTCCCCAGAGAAC (117) | CATGACAAGACTGGAGGGAAGA (118) | A/G | 69703470 |
| SYN3a | 4 | TCGAGTCATTGGCATCCCTAGTA (119) | CTTTCTTGACATTCCTGGGCTT (120) | none | |
| SYN3a | 5 | TATAGAGGATAAAGCGGAGACAC (121) | AAAGACTCACTTGCCCAATACC (122) | none | |
| SYN3a | 6 | TCTGTAACTCGGATTGCTTTCTTG (123) | GATTGCTGCTTACCAGTCTGTGT (124) | none | |
| SYN3a | 7 | GTCGAATTGCATGATTGAAACC (125) | GCGGAACCTTTTGTGGCTATTA (126) | none | |
| TOM1 | 1 | TGGATCACTGGCTGGGACACT (127) | GTTCAGTAGGCGTGTAGTCCCAG (128) | none | |
| TOM1 | 2 | GCTGGCTTTGTCCTGTGAAGATG (129) | CGGGAAGGCAGGTAGATTGACTC (130) | none | |

TABLE 3-1-continued

SNP discovery: PCR primers, amplicons and polymorphisms (the number following each sequence is its SEQ ID NO)

| Gene | Primer pair | Forward primer | Reverse Primer | SNP | SNP location[1] |
|---|---|---|---|---|---|
| MCM5 | 1 | GCTCTCCCTTTGCGACTTTCTCT (131) | TCCAGCCTTCACAACCTACCACT (132) | none | |
| MCM5 | 2 | TCCTGGAATCGTGTGTGTGTG (133) | AGGGCTAGAACCAGTGGAGAGGA (134) | none | |
| HMOX1 | 1 | ATAGCTCATGCGTGCCAGGACT (135) | TCTGGCTACATCTTCTGGGCTCT (136) | none | |
| HMOX1 | 2 | CTGTGGATGACCTGATGGGAGTG (137) | ACACAGCCACTTTCCCAACTACCT (138) | none | |
| TXN2 | 1 | CCAAACCACTGGGACAGTGAGT (139) | GGAGGTGGAAGGGATCACATAA (140) | none | |
| TXN2 | 2 | GCGTCCAGTTCCCAGTTCCTT (141) | GGCTTGGCTGGGTGTTACTGTC (142) | A/C | 73912042 |
| EIF3S7 | 1 | TTTGAGGAAGAGATCGTGTGTG (143) | AGAAGTGAATGTGGCAAAAGAGT (144) | T/C | 73948028 |
| EIF3S7 | 1 | TTTGAGGAAGAGATCGTGTGTG (143) | AGAAGTGAATGTGGCAAAAGAGT (144) | A/G | 73948017 |
| EIF3S7 | 1 | TTTGAGGAAGAGATCGTGTGTG (143) | AGAAGTGAATGTGGCAAAAGAGT (144) | A/G | 73947882 |
| EIF3S7 | 1 | TTTGAGGAAGAGATCGTGTGTG (143) | AGAAGTGAATGTGGCAAAAGAGT (144) | A/G | 73947851 |
| EIF3S7 | 1 | TTTGAGGAAGAGATCGTGTGTG (143) | AGAAGTGAATGTGGCAAAAGAGT (144) | G/C | 73947448 |
| EIF3S7 | 2 | CCTATGTCGTTTGAATCACCAC (145) | CCCCCTCCATTATAAAGTTTTC (146) | T/C | 73949685 |
| EIF3S7 | 2 | CCTATGTCGTTTGAATCACCAC (145) | CCCCCTCCATTATAAAGTTTTC (146) | T/C | 73949318 |
| EIF3S7 | 2 | CCTATGTCGTTTGAATCACCAC (145) | CCCCCTCCATTATAAAGTTTTC (146) | T/C | 73949144 |
| SSTR3 | 1 | GAGAATGGATGGATGGATGAAT (147) | GCATTGCAGACAGATGCTTTAC (148) | none | |
| SSTR3 | 2 | CAGGCTGGTTATCATTCTGCTGTC (149) | ATCTGTACCCCACTTCCAGCCTC (150) | none | |
| SSTR3 | 3 | GTTATCATTCTGCTGTCCCCTCT (151) | TAACAAGATCTGTACCCCACTTCC (152) | none | |
| SSTR3 | 4 | CCACCCTCTTCCCTTCTAGATT (153) | TTAGCTTAAGTGCCAGCTTTCC (154) | none | |
| SSTR3 | 5 | AATGTTGGAATCAGCCCTTAGA (155) | GGGAAGAGGGTGGGATATAGAC (156) | none | |
| SSTR3 | 6 | AAGGTAACAACGCCTCCTTGTA (157) | CATCATTTGGAAAAGGGAGAAG (158) | none | |
| SSTR3 | 7 | CACGTAGATGACCAGGGAGTTG (159) | GGGAAGGACACAGTCTATCTCAG (160) | none | |
| SSTR3 | 8 | CACCAGGAAATAGAGGCCGAAG (161) | GCATTCTGATCCCACTGGTCTAC (162) | none | |
| SSTR3 | 9 | ATCGAACCCTCATCTCCTGTG (163) | GTGCTCAACATCATCAATGTGG (164) | none | |
| SSTR3 | 10 | TTGTGGTTCCCACATTTTCTCT (165) | CTTGCTTTGTGTCCTATGGTTG (166) | none | |
| SSTR3 | 11 | AGGACTCTGGAAGGCAATACAC (167) | TCCTCAGAGAAAATGTGGGAAC (168) | none | |
| SSTR3 | 12 | CAACAACCACATTGTACCAACC (169) | GAGAGCTTGATCCAAAAGCAGT (170) | none | |

[1]Genomic location based on Bovine Genome Assembly version 3.1

PCR amplicons of approximately 800 bp containing exonic and intronic regions of the targeted genes were sequenced to identify polymorphisms (Table 3-1). PCR amplification was performed in a volume of 50 µl containing 1×PCR reaction buffer, 0.2 mM of each dNTP, 0.3 µM of each forward and reverse primer, 3% DMSO, 50 ng genomic DNA, and 1 unit of GoTaq DNA polymerase (Promega, USA). The DNA template used for SNP discovery was from a sire for which there was strong evidence of heterozygosity for a BTA5 twinning rate QTL (Cruickshank et al., 2004). Touchdown PCR was used in all amplifications with an initial denaturation at 95° C. for 2 min, followed by 10 cycles with denaturation at 94° C. for 45 sec, annealing for 30 sec, and extension at 72° C. for 70 sec. Annealing was at 65° C. initially, with a 1° C. reduction per cycle, down to 56° C. Twenty-five additional cycles were performed at the same denaturation and extension temperatures and times with annealing in all cycles at 56° C. for 45 sec. The last cycle was followed by a final incubation at 72° C. for 8 minutes. PCR products were purified with the MinElute PCR purification kit (QIAGEN, La Jolla, Calif.). Sequencing was performed in both directions using forward and reverse primers with the BigDye® Terminator v3.1 Cycle Sequencing Kit (Applied Biosystems, USA). Sequencing reactions were analyzed on an ABI3700 at the University of Wisconsin-Madison Biotechnology Center.

Genotyping:

A total of 106 SNPs (Table 3-2) were successfully genotyped between 5 Mb and 85 Mb on chromosome 5. Assays were developed for an additional 14 SNPs but these failed to produce scorable genotypes. Of the 106 successfully genotyped SNPs, 71 had been used in a previous study (Kim et al., 2008) and were chosen considering marker location and minor allele frequency (MAF) in Holsteins. Minor allele frequency of all chosen markers was higher than 5% in the previous study (Kim et al. 2008). Thirty-six markers were newly developed within thirteen genes located between 55 Mb and 75 Mb on BTA5. Sixty-four of the 120 SNPs were located between 55 and 75 Mb on BTA5, to aid fine-mapping in this region.

TABLE 3-2

Location and identification of SNPs successfully genotyped.

| SNP ID | Gene | Position (Mb)[1] | SNP ID | Gene | Position (Mb)[1] |
|---|---|---|---|---|---|
| Table 3-1 | IFNG | 45363554 | ss38322851 | — | 25542789 |
| Table 3-1 | IFNG | 45366118 | ss38333998 | — | 25612221 |
| Table 3-1 | PPM1H | 50646348 | ss38329202 | — | 25805367 |
| Table 3-1 | PPM1H | 50646401 | ss46526967 | — | 26051044 |
| Table 3-1 | INHBE | 54966387 | ss38331375 | — | 26213185 |
| Table 3-1 | INHBE | 54966493 | ss46526664 | — | 27484121 |
| Table 3-1 | INHBC | 54977448 | ss38334615 | — | 30959868 |
| Table 3-1 | SNRPF | 58655362 | ss38325441 | — | 31234560 |
| Table 3-1 | SNRPF | 58655519 | ss38332189 | — | 31393992 |
| Table 3-1 | SYCP3 | 63551646 | ss38334249 | — | 32887508 |
| Table 3-1 | SYCP3 | 63553642 | ss38324817 | — | 36286204 |
| Table 3-1 | SYCP3 | 63554840 | ss38330986 | — | 37017623 |
| Table 3-1 | SYCP3 | 63564144 | ss38322423 | — | 37772751 |
| Table 3-1 | SYCP3 | 63564196 | ss38333459 | — | 38215050 |
| Table 3-1 | IGF1 | 64222809 | ss38333457 | — | 38217081 |
| Table 3-1 | IGF1 | 64272121 | ss38328259 | — | 39432441 |
| Table 3-1 | IGF1 | 64273448 | ss38332923 | — | 39860001 |
| Table 3-1 | IGF1 | 64274119 | ss38326081 | — | 43015339 |
| Table 3-1 | RIC8B | 65538715 | ss38333096 | — | 46763982 |
| Table 3-1 | RIC8B | 65548214 | ss38330228 | — | 49060290 |
| Table 3-1 | RIC8B | 65549039 | ss38332913 | — | 50736312 |
| Table 3-1 | CKAP4 | 66075473 | ss38330728 | — | 50756220 |
| Table 3-1 | SYN3 | 69267636 | ss38335703 | — | 53605874 |
| Table 3-1 | SYN3 | 69280766 | ss38335704 | — | 53606067 |
| Table 3-1 | SYN3 | 69690202 | ss38322168 | — | 58377370 |
| Table 3-1 | SYN3 | 69690568 | ss38334842 | — | 58469225 |
| Table 3-1 | SYN3 | 69690601 | ss38336375 | — | 58760185 |
| Table 3-1 | SYN3 | 69690919 | ss38323314 | — | 59750361 |
| Table 3-1 | SYN3 | 69691212 | ss38324210 | — | 60571988 |
| Table 3-1 | SYN3 | 69703674 | ss38326045 | — | 62924050 |
| Table 3-1 | EIF3S7 | 73947622 | ss38324469 | — | 63440624 |
| Table 3-1 | EIF3S7 | 73948047 | ss38323954 | — | 64228962 |
| Table 3-1 | EIF3S7 | 73949317 | ss38329400 | — | 64506317 |
| Table 3-1 | EIF3S7 | 73949530 | ss38335844 | — | 65786585 |
| Table 3-1 | EIF3S7 | 73949897 | ss38329473 | — | 66527964 |
| ss38332405 | — | 5918850 | ss38322176 | — | 66797547 |
| ss38323163 | — | 6673215 | ss38330735 | — | 67281572 |
| ss38333589 | — | 8441967 | ss38336504 | — | 67908996 |
| ss38322192 | — | 8507929 | ss38333147 | — | 69192069 |
| ss38334594 | — | 8926891 | ss46527005 | — | 69688243 |
| ss38331238 | — | 10929300 | ss46526764 | — | 69690399 |
| ss38334462 | — | 11433635 | ss46526677 | — | 69956055 |
| ss38324419 | — | 12268428 | ss38328460 | — | 74012901 |
| ss38324418 | — | 12268601 | ss38326324 | — | 74016524 |
| ss38335775 | — | 12514696 | ss38326323 | — | 74016632 |
| ss38333537 | — | 12826659 | ss38336298 | — | 74152696 |
| ss38324813 | — | 16835901 | ss38322350 | — | 76637809 |
| ss38328726 | — | 17309176 | ss38335160 | — | 78004851 |
| ss38328727 | — | 17309229 | ss38324385 | — | 78821368 |
| ss38334640 | — | 18016855 | ss38324387 | — | 78821694 |
| ss38323327 | — | 19161398 | ss38322778 | — | 84526473 |
| ss38326471 | — | 22351578 | ss38326000 | — | 87242524 |
| ss38329587 | — | 25226289 | ss38324928 | — | 87508710 |

[1]Based on Bovine Genome Assembly version 3.1.

Genotyping was performed by mass spectrometry of allele-specific primer extension reactions (Sequenom, San Diego, Calif.). Three microsatellite markers, CSSM022, ILSTS066, and BMS1216, located at 60.26, 60.27, and 69.3 Mb respectively, were also genotyped. DNA extraction and microsatellite genotyping were performed as described by Cruickshank et al. (2004).

Linkage, Linkage Disequilibrium, and Haplotypes:

Linkage map distances were estimated using CRIMAP 2.4 (Green et al. 1990). Linkage mapping was also used to examine the marker order predicted by the SNP genomic location obtained from bovine genome assembly 3.1. If the linkage map location was different (>30 cM) from its expected genomic position in genome assembly 3.1, it was considered as a probable genome assembly error.

Haplotype construction was performed using information on partial haplotypes obtained by linkage mapping. The most probable paternally inherited haplotype of offspring in each half-sib family was constructed using the chrompic option of CRIMAP. Sire haplotypes were inferred using reconstruction of paternally-inherited alleles and linkage phase in offspring obtained from CRIMAP.

LD was calculated as D' and $r^2$ between all pairs of SNPs on chromosome 5 (BTA5). Hardy-Weinberg equilibrium (HWE) was tested for each SNP to find reduction in marker heterozygosity versus that predicted under HWE. To remove linkage effects within half-sib family from LD estimation, maternally-inherited haplotypes were analyzed in Haploview for construction of LD analysis (Barrett et al. 2005).

Linkage-Linkage Disequilibrium QTL Mapping:

Combined linkage-linkage disequilibrium analysis (LLD) was conducted to fine-map QTL. Linkage effects are based on transmission of alleles from sires to sons, while LD effects are estimated based on maternally-inherited haplotypes. There is increased probability that the QTL alleles carried on marker haplotypes with greater similarity are identical by descent (IBD). IBD probability between two haplotypes was estimated using the procedure proposed by Meuwissen and Goddard (2001). To predict IBD of a genomic position, eight-marker windows were used. Calculation of the likelihood at putative QTL positions was performed using restricted maximum likelihood (REML). The statistical model was $$y = Zu + Wq + e \quad (1)$$

where: y is twinning rate PTA of the individual; u is vector of random polygenic effects; q is vector of additive QTL effects; e is vector of individual error terms; W is an incidence matrix of haplotypes relating phenotypic records to QTL alleles; and Z is a diagonal incidence matrix relating individual polygenic effects to individual sons.

The random effects u and q are assumed to be distributed u~(0, A$\sigma_u^2$) and q~(0, G$\sigma_q^2$), where: $\sigma_u^2$ and $\sigma_q^2$ are the polygenic variance and the additive QTL variance, respectively; A is the matrix explaining additive genetic relationship among animals; and G is the allele relationship (IBD) matrix between haplotypes.

To refine QTL location, Data I and II were analyzed both separately and together, in a multivariate analysis treating predicted transmitting abilities from the different data sets as separate traits. Individual random effects with corresponding variance and log likelihood ratio were estimated using the mixed procedure (SAS, 1996).

The log likelihood of the data under linkage only and LLD hypotheses was compared with that under the null hypothesis of no QTL at a given map position. The G matrix was constructed with linkage or LLD to test QTL hypotheses. The no QTL model with the A matrix accounting for additive genetic relationship is the same as the animal model (Lynch and Walsh 1998). The log likelihood test (LRT) was calculated as −2[(log likelihood of polygenic model)−(log likelihood polygenic with QTL model)], an approximation of the chi-square distribution with one (1) degree of freedom.

To determine the threshold level for a genome-wide scan, an analytical method proposed by Lander and Kruglyak (1995) was used. Comparison-wise error rates (CWER) of $2.3 \times 10^{-5}$ and $7.2 \times 10^{-4}$ yielded experiment-wise error rates corresponding to the significant and suggestive levels. For linkage QTL threshold, significant ($p=5.0 \times 10^{-5}$) and suggestive level ($p=0.002$) were used.

Association Testing:

A model that included the effects of sire and SNP genotype was used to evaluate the association between each SNP marker locus and a twinning rate PTA. A SNP genotype (or haplotype) effect and family effect were included in the linear model:

$$y = Xb + s + e \quad (2)$$

where: y is twinning rate PTA of the individual; b is a vector of the intercept and the regression coefficient; X is an incidence matrix of genotypes for b; and s is family effect. The size of vector b was variable for single SNP marker genotypes (2×1). The inverse of the prediction error variance (PEV) of PTA was used as a weight.

Positional Candidate Gene Analysis:

Based on initial mapping results, IGF1 was considered a strong positional candidate gene. This gene was screened for polymorphism over its full 72 kb genomic region, including 2 kb of flanking regions (5' and 3'), using the same approach and sire as described above (Table 3-3).

TABLE 3-3

IGF1 SNP discovery: PCR primers, amplicons and polymorphisms (Number in parentheses after each sequence is SEQ ID NO).

| Primer Pair | Forward Primer | Reverse Primer | PCR Prod | Start Base | End Base[1] | SNP (name) | SNP Location |
|---|---|---|---|---|---|---|---|
| 1 | TATTCCCACCATTCCAGAAAAC (171) | GGCGAGCAATTTTATATTCCAG (172) | 817 | 64278103 | 64277286 | | |
| 2 | GAGTAGGCTTGAGATGGTCTTTT (173) | TCAGATCCCACAGAATTGCATA (174) | 816 | 64277365 | 64276549 | C/T (SNP1) | 64277279 |
| 3 | TTCGGCACTGGGAGTTATTTAT (175) | TTTGCTGAGAATGGAAACTTGA (176) | 774 | 64276604 | 64275830 | | |
| 4 | ACTGACTTCGCCTTTCCAATAA (177) | CCAGATCTTTTACAGCAGGTCA (178) | 975 | 64275885 | 64274910 | | |
| 5 | AAAGACACAGGCTCTTGCTCAAT (179) | TCTGCACAGAAACAGAGAATGG (180) | 829 | 64271572 | 64270743 | | |
| 6 | CTGGCAATAAAGCAATTCTATCC (181) | ACATTGTCACAGAGTGCTATAAACC (182) | 750 | 64270787 | 64270037 | G/A (SNP2) | 64270644 |
| 7 | AAGGTTCTACATGGCAACTCTTA (183) | ATTGGCTCAGACATGAAACAGA (184) | 844 | 64270163 | 64269319 | | |
| 8 | GACGAGACATTTAGATCCTCCCTA (185) | CAAGACTGGTTGACATGCTCTC (186) | 757 | 64269381 | 64268624 | | |
| 9 | CACAGCTTCACCAGACATTACAT (187) | GAAGTTTAAATGCCTGCCAAAG (188) | 854 | 64268703 | 64267849 | | |
| 10 | CTCAGAAAACTGCTCCCAGAC (189) | CAGCTGTCACACAAGTGCATAG (190) | 793 | 64267936 | 64267143 | | |
| 11 | TGGATTTGAGCTACACCATTTG (191) | GTAGTCCTTGTTTTGGAGATGAG (192) | 797 | 64267220 | 64266423 | | |
| 12 | ACTTACTTGGTGGGTGGCATT (193) | TACACTGCAACACTTTGGACCT (194) | 786 | 64266502 | 64265716 | | |
| 13 | GATCCAGAACCAAAGCAAGGTC (195) | GGATCCAAAATGGAGCTATGAG (196) | 769 | 64265805 | 64265036 | | |
| 14 | CAGTGCAGGTGCCTCTCAAC (197) | TTACCTTTGGACAAATGCAGAG (198) | 847 | 64265134 | 64264287 | | |
| 15 | ATTACTTTATGCAATTGGCAAGAACGACCTGAAGTGGATTTGGAATG (199) | (200) | 789 | 64264374 | 64263585 | | |
| 16 | ACCATACACTTGGCCTTTCAAT (201) | GAAGTCAATCAAACATGGTGCT (202) | 841 | 64263639 | 64262798 | | |
| 17 | TCAGCCTCAGCACTATTGACAT (203) | AGTGGCTTCTCCAAGAGCATAC (204) | 829 | 64262902 | 64262073 | | |
| 18 | CCACCAGAAAGCAGAAACAGAT (205) | TGTGATAAGGAAGCAGTTGAGG (206) | 769 | 64262148 | 64261379 | | |
| 19 | GAGCATGGCTTTGGTGAAATA (207) | AGTGAGAACACTGAACCAGATTG (208) | 756 | 64261386 | 64260630 | | |

TABLE 3-3-continued

IGF1 SNP discovery: PCR primers, amplicons and polymorphisms (Number in parentheses after each sequence is SEQ ID NO).

| Primer Pair | Forward Primer | Reverse Primer | PCR Prod | Start Base | End Base[1] | SNP (name) | SNP Location |
|---|---|---|---|---|---|---|---|
| 20 | CACAAGTGCTTTCTCCTTACCA (209) | TCTTCATTCCATGAGTCACCAC (210) | 804 | 64260720 | 64259916 | | |
| 21 | AAAGTTTCCAGCCGTTCATAGA (211) | TGGTGGTTGAGAGCAACATTAC (212) | 820 | 64259983 | 64259163 | | |
| 22 | AAATCTGGCTGGCATTTCTG (213) | AGGAGTTCCAATTTCCAGTTCA (214) | 846 | 64259272 | 64258426 | | |
| 23 | ATAGAACTGCTCCACGCATAAC (215) | CCAATAATCCCATTTCAGAAGC (216) | 787 | 64258489 | 64257702 | | |
| 24 | ACGAGTCTTCAAACCTGTCTCC (217) | ATGCATAAAGGTCCAAGTCCAG (218) | 789 | 64257783 | 64256994 | | |
| 25 | ATCACATCCCTCAATGTGGTTC (219) | TGGTTTCGAGATGATTCAAGTG (220) | 831 | 64257113 | 64256282 | | |
| 26 | AGGGTGGAGCCGATGTAATAA (221) | CACTATTGGACACAAAGCCATC (222) | 832 | 64256357 | 64255525 | | |
| 27 | CCCTCATCACTCACCAAAACTA (223) | ACTAGACGGCATAAAGCATGAA (224) | 761 | 64255592 | 64254831 | | |
| 28 | TCCTCTAACAACACATAATCTAGCCGGGTACACAGTTGTCCAGAAGAC (225) | CTGGACTAGGGGATACAGAGGA (226) | 836 | 64254907 | 64254071 | | |
| 29 | ACTCAGTGACTTCAGCAATGGA (227) | CTGGACTAGGGGATACAGAGGA (228) | 784 | 64254206 | 64253422 | | |
| 30 | TCCATTACAAGTTCCACGCAAA (229) | AGAGGAAGCTCTCAAGGAGGAT (230) | 756 | 64253502 | 64252746 | | |
| 31 | TACTGAGGTTGCAAGTGGGTTA (231) | GGTAATAGAGCGTGGTGACCTT (232) | 762 | 64252815 | 64252053 | | |
| 32 | CCTCCCTGTGGTATTTTCTCTG (233) | CTGGATAGCTGGCATCAAGAC (234) | 791 | 64252338 | 64251547 | | |
| 33 | CTAGGGTGAGGCGATGGAAA (235) | TTGAGTTGCAAGATCCAAATGT (236) | 797 | 64251626 | 64250829 | | |
| 34 | AGTGGGATCATTCCTGTGAAAC (237) | GAGGTCTGGGAAATGTCAAGG (238) | 802 | 64250905 | 64250103 | | |
| 35 | CCCTTTCAGGGAAATCTAGGAC (239) | TGGTAAGGGATTAGGATCTCACA (240) | 766 | 64250213 | 64249447 | | |
| 36 | TTGGCTGCAAGGTATGTGAG (241) | TGAACCTGGAATTGTGTTCTTG (242) | 756 | 64249484 | 64248728 | | |
| 37 | AAAACATTTGGAAAAGCACGAT (243) | GAACTATCTCTGCATTGAGCAC (244) | 848 | 64248793 | 64247945 | | |
| 38 | AAGGATGTCAAACAAACAAGCA (245) | TCCTTAATACCTTCCCAGGACA (246) | 659 | 64248079 | 64247420 | | |
| 39 | TGATCATGTAGAAGGGAAAGCA (247) | TTTCACCATAAGCGGAAACATA (248) | 845 | 64247260 | 64246415 | | |
| 40 | ATCAGAGCAAGAGGGACTTCAC (249) | CTTGCAGAATAGAGGAGGCAGT (250) | 786 | 64246402 | 64245616 | | |
| 41 | GGAGATAGAAGAACCACGGAAT (251) | CAGCAGCAGCAGACTGAAAC (252) | 751 | 64245791 | 64245040 | | |
| 42 | CCCTCTTATCCCTGTGAAACTG (253) | TCCTTCCTTAAAAGACCACCAA (254) | 772 | 64245128 | 64244356 | | |
| 43 | AGCATTCCAGTCAGCAAGATTT (255) | TGAAATTGCTCAAGAAACATGG (256) | 821 | 64244422 | 64243601 | | |

TABLE 3-3-continued

IGF1 SNP discovery: PCR primers, amplicons and polymorphisms (Number in parentheses after each sequence is SEQ ID NO).

| Primer Pair | Forward Primer | Reverse Primer | PCR Prod | Start Base | End Base[1] | SNP (name) | SNP Location |
|---|---|---|---|---|---|---|---|
| 44 | CTGGCTTCGCTCCAGATTTTA (257) | TTAGCAGCAGCAAGACCATTTA (258) | 814 | 64243890 | 64243076 | | |
| 45 | TTTAGTGCTTGGACAGACCTGA (259) | AGCTGACAGATTTCCCAATTTC (260) | 814 | 64243150 | 64242336 | | |
| 46 | AAAGCTGGAGACAGAACAGTCA (261) | AACTCCTCTGGCAGGTTATGAA (262) | 767 | 64242419 | 64241652 | | |
| 47 | CCTACTAGAGAGTAAGGGTGACTTG (263) | AATGTAGGATGACAACCATCTGC (264) | 763 | 64241735 | 64240972 | A/G (SNP3) | 64241296 |
| 48 | GAATCAAAGATGGAAGGAAAGC (265) | GGGTATTGGGAGAAGTGAGTGA (266) | 827 | 64241065 | 64240238 | | |
| 49 | ATGCTTGAGAATCTTTCCCTG (267) | AGACCCTGCTAAATTGTAAC (268) | 878 | 64240368 | 64239490 | | |
| 50 | GGTAGATTCCCCAAGGAGAAAG (269) | CCTTGGACTCCTATTTTCCAGA (270) | 815 | 64239855 | 64239040 | | |
| 51 | CAGGATACAGTTGCCTTAGTTCC (271) | AAAACATCAGAGGGAAAATGAC (272) | 795 | 64239105 | 64238310 | | |
| 52 | GACCCCTCAACACAGAAGTACC (273) | ATTGTCAGGTGGGTATTCAAGC (274) | 804 | 64238400 | 64237596 | C/T (SNP4) | 64237899 |
| 53 | GATCCTTGGGAAGTCTGTTGTC (275) | ACCAACTTCAGGTTCACATGC (276) | 814 | 64237670 | 64236856 | G/A (SNP5) | 64236951 |
| 54 | CACAGCCTGAGAAGCACTGATA (277) | CCCATAAGGAGAGGAGGAGTTT (278) | 750 | 64236974 | 64236224 | | |
| 55 | TCAGAAGGATCATGAGAGCAGA (279) | ACCAGACTCTTGCTATCCCAAC (280) | 811 | 64236288 | 64235477 | | |
| 56 | CATGCATCTGGGTGAGAACTAA (281) | TGCAAGTTTCTCTGGAGATTGA (282) | 810 | 64235551 | 64234741 | G/A (SNP6) | 64235335 |
| 57 | CAAAGGCATCCATCTGTTCTAA (283) | GTCTTCCTCTTCCTCCTCCTTT (284) | 756 | 64234839 | 64234083 | | |
| 58 | TGGTTCATTGAGAAGATACAGGA (285) | GGGACCTCCCAAGAAAGAAT (286) | 788 | 64234180 | 64233392 | | |
| 59 | GAGCTAATCATGGTGGCTCAGT (287) | CGGCTCATCTCCAAGCTAAAAG (288) | 814 | 64233527 | 64232713 | A/G (SNP7) | 64232988 |
| 60 | GAGGTTTGGAGATAACAGACATGA (289) | GCTGAATGTTTCCTTTGGAGAG (290) | 810 | 64232789 | 64231979 | | |
| 61 | CATCAAGGAAGCCCAAGAATAC (291) | AATTAGGAGGCTGAGAAAGGTC (292) | 835 | 64232149 | 64231314 | | |
| 62 | TCCTCATGCCTCAAAACCTTTA (293) | TGCCATATGCAGAGAGGAAATA (294) | 799 | 64231419 | 64230620 | | |
| 63 | GGAAGCCAATGTTGTTTTCAG (295) | ACCACCACGTTATCTCCCATAC (296) | 793 | 64230685 | 64229892 | | |
| 64 | CTCTCTTCCCACATCTGAAAGG (297) | TTTCTCCCAAATAATCCACTCAC (298) | 811 | 64229958 | 64229147 | G/T (SNP8) | 64229843 |
| 65 | CTACACCTATCCCATGCCTTGC (299) | ATACCAGTGAAGGAGGCAACAT (300) | 779 | 64229247 | 64228468 | | |
| 66 | AAGTGGCAGATTCCAGATTTGT (301) | GTTTGCTGGTCCCACTACTTCT (302) | 838 | 64228540 | 64227702 | | |
| 67 | AACAGGGCCACAATTCCTAGA (303) | GAAAGATGCCTTCAGTGCTGTT (304) | 753 | 64227766 | 64227013 | | |

TABLE 3-3-continued

IGF1 SNP discovery: PCR primers, amplicons and polymorphisms (Number in parentheses after each sequence is SEQ ID NO).

| Primer Pair | Forward Primer | Reverse Primer | PCR Prod | Start Base | End Base¹ | SNP (name) | SNP Location |
|---|---|---|---|---|---|---|---|
| 68 | CAATGCATGAAAGTTGTGTGTG (305) | GGGCTATTCCTAGAAAATTCACCT (306) | 761 | 64227102 | 64226341 | C/T (SNP9) | 64226917 |
| 69 | GTTGGTGTAGGAAACCTGTCTG (307) | AAGAGACAGACATAGAGGACAAAC (308) | 762 | 64226493 | 64225731 | C/T (SNP10) | 64226056 |
| 70 | CGACTTTCTCCCTTGGTATACAT (309) | CTCTGGTCATTCATCATTGGTT (310) | 836 | 64226067 | 64225231 | | |
| 71 | ATGTAGCACCAATAAAGGCAGT (311) | AAACTCATCGAGGCCAACTAAA (312) | 830 | 64225294 | 64224464 | | |
| 72 | GGTTTGAGCATCTTCAGGAACT (313) | AGGCTTGATTTCTGGTTCTACA (314) | 790 | 64224607 | 64223817 | | |
| 73 | GGCCTCTCAATTGGTGAGAAA (315) | CATCATCCACCACAGGTAACAA (316) | 898 | 64223890 | 64222992 | C/T (SNP11) | 64223363 |
| 74 | CCTGAGAGGTCCATCTTTTCTG (317) | GCAAAGGTGTCATTAGGAGCTT (318) | 860 | 64220462 | 64219602 | C/T (SNP12) | 64220270 |
| 75 | CAAAACTAGCATTGTGCAGAGG (319) | AGCTGGCCTACTTTTCTTCCTT (320) | 808 | 64219666 | 64218858 | | |
| 76 | CGAGAGAGAAGCAGACAGAAAG (321) | CAATTCCAAGTGGAGGAAAGAG (322) | 760 | 64218929 | 64218169 | | |
| 77 | AAGTCGGAGTATTGGCAGGAT (323) | AGTCCATGTTGATTTGTGCTG (324) | 802 | 64218254 | 64217452 | | |
| 78 | AAGTCGGAGTATTGGCAGGAT (325) | TGCAGGTTACTCTCAGGTGGTA (326) | 768 | 64217526 | 64216758 | G/C (SNP13) | 64216781 |
| 79 | TGGAACCAGCCTCAGGTATAAG (327) | CGGAGATTCCATGTAGCCTAGT (328) | 849 | 64216832 | 64215983 | | |
| 80 | AGTAGCACTGTGTGTGTTAGAT (329) | ATTGCATTATTTTCCCAAGGAC (330) | 770 | 64216069 | 64215299 | A/G (SNP14) | 64215386 |
| 81 | CTGGTTTCAGACCCTGGCTA (331) | TCCACCCTTACATCCTAACAGC (332) | 821 | 64215364 | 64214543 | | |
| 82 | GCCTCTCACAAGCATTTGATCT (333) | ATGAGTATCAGGGAATGGTGCT (334) | 840 | 64214642 | 64213802 | | |
| 83 | AGATCTGCAAGGTCAAAATCA (335) | TTTCTCCCAAAACTATTTGCTG (336) | 786 | 64213879 | 64213093 | T/C (SNP16) | 64213395 |
| 84 | AATTCCAAATATCCTTGGTGGT (337) | TGGAAGGCTTTTCTGAACTTTT (338) | 809 | 64213160 | 64212351 | | |
| 85 | CACGTCAATCTCAAACAGATGC (339) | TATCCTGTCTTGGCAATTCCTT (340) | 850 | 64212435 | 64211585 | | |
| 86 | TTCAAACAGAGTCAGGTGGTATC (341) | GCAGGTAGCATAGTCCCTTCA (342) | 755 | 64211725 | 64210970 | A/T (SNP17) | 64211268 |
| 87 | TTTAACAAGCTTTTCCTGGTTC (343) | ATGTGGTTAGAGTGGGAAGGA (344) | 836 | 64210964 | 64210128 | | |
| 88 | CAAAGATGGCCAATAAAGAAGTC (345) | TTTAGGGAGGAAGCATTGATGT (346) | 812 | 64210290 | 64209478 | | |
| 89 | GTTTGTAGTGGGTGGAGATGGA (347) | AACCTCAGGAGATGACGTTGTT (348) | 796 | 64209544 | 64208748 | | |
| 90 | TTGTTCCTATGTGACCTCAAGC (349) | CATCTGTTGCTTTGCTCATTGT (350) | 751 | 64208840 | 64208089 | C/A (SNP18) | 64208267 |
| 91 | CTTCTAGCAGGCCTCCACTTG (351) | TAGACCCTGCTGATGGTATATG (352) | 802 | 64208171 | 64207369 | | |

TABLE 3-3-continued

IGF1 SNP discovery: PCR primers, amplicons and polymorphisms (Number in parentheses after each sequence is SEQ ID NO).

| Primer Pair | Forward Primer | Reverse Primer | PCR Prod | Start Base | End Base[1] | SNP (name) | SNP Location |
|---|---|---|---|---|---|---|---|
| 92 | CATGTGCTTTCTTGTTGCTTGT (353) | TTGACTCAGACCCATAGGGATT (354) | 750 | 64207611 | 64206861 | | |
| 93 | TTGATCACTCTAATGTTCCAGGT (355) | TTGGATTAAACATTCTGGGTTC (356) | 755 | 64206938 | 64206183 | | |
| 94 | CCTTGGATAACAGAACTGGTTG (357) | CCCATCTCTTTCTAACATTGGAT (358) | 814 | 64206256 | 64205442 | | |
| 95 | ACCCTGGCCCAAGTTGTCTAT (359) | CTGGTGTGCTACTTAACTGCTTG (360) | 750 | 64205523 | 64204773 | | |
| 96 | GTTCCTCTATCCCACTCCCTTC (361) | TTAATCCTCATACCACCCCTGT (362) | 835 | 64204863 | 64204028 | | |
| 97 | GAAACAAACATCTGACGACTCTG (363) | TCTTGGGCTTAAAGAGAGGAAA (364) | 851 | 64204173 | 64203322 | | |
| 98 | CACCTGGGAAACCAAATCTAAT (365) | TTATCTCAACCCACAGAACCCAT (366) | 849 | 64203421 | 64202572 | | |
| 99 | GAATTCAGCACCTCCAGCAT (367) | TGAGTGGATTCTGATGGAAAGA (368) | 826 | 64202694 | 64201868 | G/A (SNP19) | 64202520 |
| 100 | CCACTCCCAATTCCTCAAATAG (369) | TTCTGCCATTTGCCTATAAGGT (370) | 809 | 64201971 | 64201162 | | |

[1]Genomic location based on Bovine Genome Assembly version 3.1

A total of 848 Holstein bulls, which included 293 of those described above, were genotyped for IGF1 SNP association testing. SNPs were genotyped using a competitive allele-specific PCR system (KBiosciences, Hoddesdon, UK). PTA estimates were determined in separate analyses based on Data I and Data II, respectively. Twinning rate PTAs were available for 309 bulls from Data I (IGF1-Data I) and all 848 bulls from Data II (IGF1-Data II). Association tests were performed as described above. Single marker associations on BTA5 are shown in Table 3-4.

TABLE 3-4

Single marker associations on BTA5.

| SNP ID | Position (Mb)[1] | Data I $-\log_{10}(p)$ | Data I Effect | Data II $-\log_{10}(p)$ | Data II Effect |
|---|---|---|---|---|---|
| ss38332405 | 5.92 | 2.24 | −0.03 | 2.94 | 0.02 |
| ss38334594 | 8.93 | 0.76 | 0.01 | 8.24 | −0.06 |
| ss38324419 | 12.27 | 0.15 | 0.00 | 4.04 | −0.04 |
| ss38324418 | 12.27 | 0.94 | −0.01 | 4.86 | −0.04 |
| ss38333537 | 12.83 | 0.18 | 0.00 | 2.78 | −0.03 |
| ss38324813 | 16.84 | 2.51 | 0.02 | 3.36 | −0.03 |
| ss46526664 | 27.48 | 0.02 | 0.00 | 3.64 | −0.02 |
| 54966387 [2] | 54.97 | 1.06 | −0.02 | 3.83 | −0.06 |
| 54966493 [2] | 54.97 | 0.60 | −0.01 | 5.30 | −0.05 |
| 54977448 [2] | 54.98 | 0.47 | −0.01 | 3.49 | −0.06 |
| ss38322168 | 58.38 | 3.76 | −0.03 | 0.19 | −0.01 |
| 58655362 [2] | 58.66 | 0.11 | 0.00 | 4.68 | −0.04 |
| 63551646 [2] | 63.55 | 1.28 | −0.02 | 3.02 | −0.03 |
| 63554840 [2] | 63.55 | 0.39 | −0.01 | 4.65 | −0.05 |
| 64273448 [2, 3] | 64.27 | 4.89 | −0.02 | 0.46 | −0.01 |
| 65538715 [2] | 65.54 | 0.42 | −0.01 | 4.05 | −0.07 |
| ss46527005 | 69.69 | 0.05 | 0.00 | 3.30 | −0.02 |
| ss46526677 | 69.96 | 4.38 | 0.03 | 0.77 | 0.01 |
| ss38322778 | 84.53 | 0.02 | 0.00 | 3.48 | 0.01 |

[1]Physical position on the bovine genome assembly 3.1
[2] Base pair locations of SNP corresponding to Table 3-1.

Results:

A total of 58 polymorphisms were discovered in 65,429 bp sequenced across 17 genes in the initial SNP discovery effort. Four of the seventeen genes screened yielded no polymorphisms. The analysis revealed varying levels of polymorphism in the remaining 13 genes. The results for SNP discovery ranged from 21 SNPs and an indel found in 2934 bp of the SYN3 genomic region, to zero SNPs found in 9100 bp of the SSTR3 genomic region. One to eight (1-8) SNPs per targeted gene were arbitrarily chosen for subsequent genotyping.

Of 120 SNPs chosen for genotyping, 106 were successfully genotyped. Linkage map position of SNPs was compared with physical genomic position of SNPs on BTA5, and there was no disagreement in SNP order. SNPs used in this study spanned 81.6 Mb from 5 Mb to 86.6 Mb on BTA5. The average linkage map distance between markers was less than 1 cM for the 106 SNPs. No recombination was detected in 66 adjacent SNP marker pairs, primarily SNP pairs within genes. In these cases SNP order was inferred from bovine genome assembly 3.1. Total linkage map distance covered was 92 cM using the current data, or 78 cM based on the USDA third generation bovine linkage map (NCBI Map Viewer).

Figure 8:
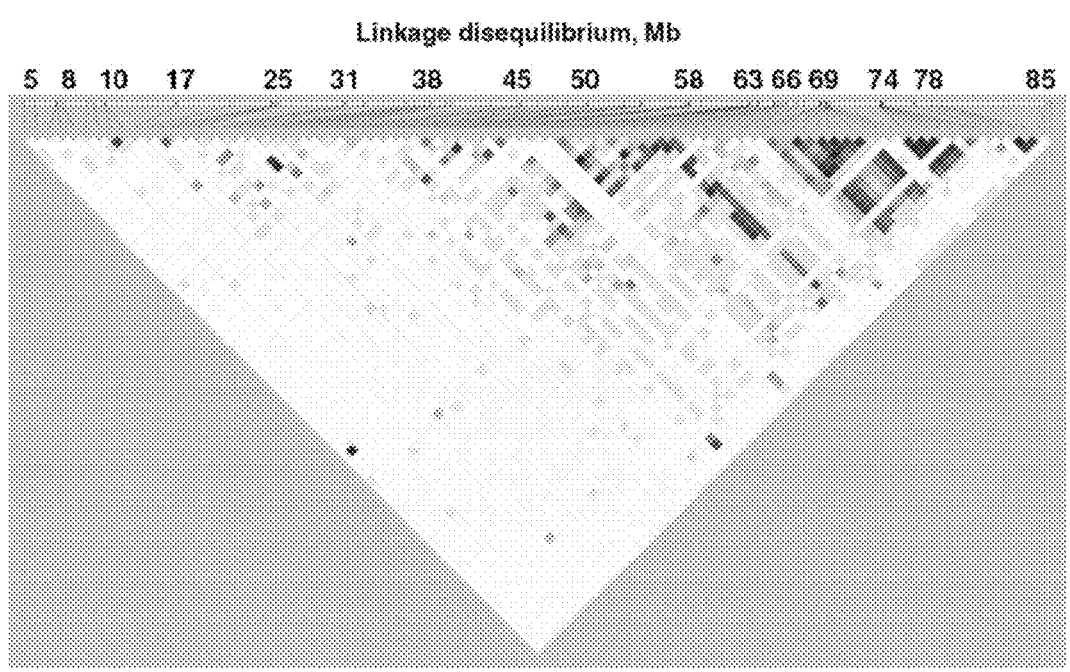
FIG. 8: Linkage disequilibrium (LD) between marker pairs between 5 Mb and 85 Mb on BTA5. LD (D') and linkage map distance between all marker pairs are plotted. Darkest square indicates high LD (D'>0.8) and lightest square indicates low LD (D'<0.2). Genomic location (Mb) of SNP markers is shown at the top of the LD plot.

Linkage map distance between adjacent SNP markers was also compared with LD ($r^2$, D') between adjacent markers. Although LD extended in some cases up to 8 cM, LD was typically decayed by 2 cM, based on $r^2 \leq 0.2$. At least one historical recombination or mutation was discovered in 94% of adjacent marker pairs that did not have any recombinants within family. Long-range LD ($r^2 > 0.5$) was discovered between genomic regions including SYN3, at 69 Mb, and EIF357, at 74 Mb (FIG. 8). Between the genomic regions corresponding to SYN3 and EIF357, mean $r^2$ among all possible SNP pairs was 0.45, and mean D' was 0.61. As only one intervening SNP was genotyped, the LD pattern between 69 and 74 Mb could not be adequately described.

The MAF range of SNPs was between 0.03 and 0.49. HWE tests detected eight SNPs in violation (p<0.05) of HWE, of which five deviated highly significantly from HWE (p<0.01) because the heterozygosity observed was lower than that predicted from allele frequencies. Two SNPs at 64 Mb, located within the IGF1 coding region, and another two SNPs, at 66 Mb and 67 Mb, respectively, also showed significant deviation.

The pattern of LD on BTA5 was surveyed prior to association testing and LLD analysis. Mean $r^2$ and D' between adjacent marker pairs were 0.16 ($r^2$) and 0.41 (D'), respectively. LD ($r^2$) within eight-marker windows varied from 0.03 to 0.71. Mean LD of each haplotype window was calculated as $r^2$ or D' between adjacent loci within eight-marker windows of the maternally-inherited haplotype. Less than fifty markers were genotyped between 5 and 55 Mb, a lower density than used for the genomic region between 55 and 75 Mb. Mean strength of LD ($r^2$) within eight-marker windows in the genomic region on BTA5 between 0 and 55 Mb was less than 0.2, while in the region between 55 Mb and 75 Mb, more than 50% of eight-marker windows were in moderate LD ($r^2$>0.4).

Figure 9:
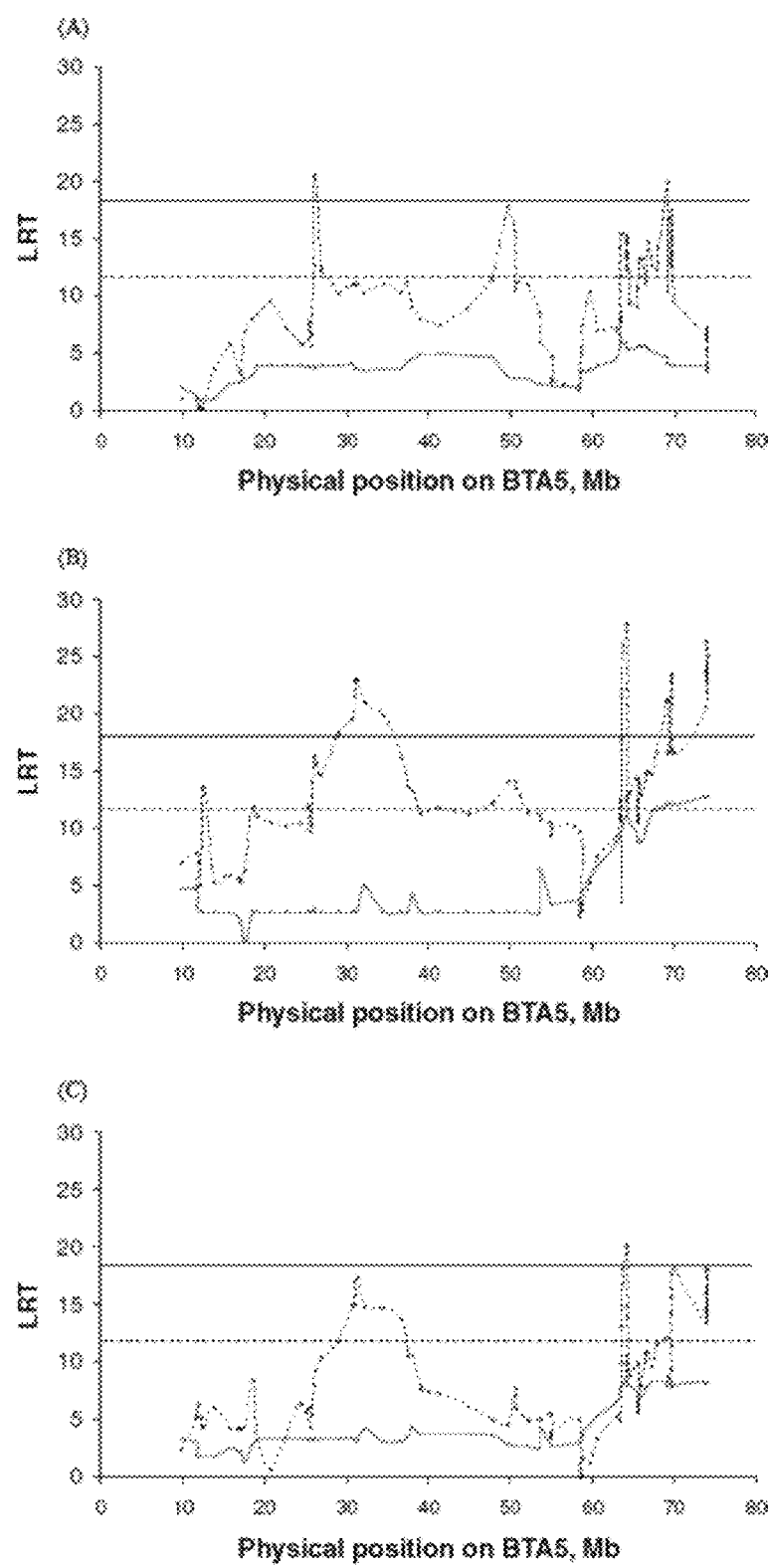
FIG. 9. Linkage and combined linkage-linkage disequilibrium (LLD) on chromosome 5. Likelihood ratio test (LRT) of linkage (light solid line) and LLD (dark dotted line) is plotted against center of eight-marker windows. (A) Results obtained using Data I; (B) Results obtained using Data II; (C) Results obtained from both Data I and Data II, plotted using multivariate analysis. Thresholds for significant (p<2.3×10-5, solid line) and suggestive (p<7.2×10-4, dotted line) linkage levels are indicated.

Evaluation for QTL affecting twinning rate resulted in multiple locations of interest on BTA5. The log-likelihood ratio (LRT) was plotted for a QTL located at the midpoint of each eight-marker window. Using Data I, the most significant LLD peak was at the midpoint of the SNP markers between 69.92 Mb and 69.99 Mb. A 2 LOD-dropoff support interval for QTL location extended from 63 Mb to 70 Mb. LLD also detected a potential QTL at 25 Mb and at 50 Mb in the 5 to 60 Mb region on BTA5 using Data I (FIG. 9A). Using Data II, LLD detected a potential QTL at 30 Mb on BTA5 (FIG. 9B). A peak at the 69 Mb regions detected using Data I was also observed using Data II, though a higher peak was observed at approximately 64 Mb, corresponding well to the location of IGF1. Multivariate analysis using Data I combined with Data II (FIG. 9C) showed the strongest evidence of QTL in the 25-35 Mb and 64-75 Mb regions, with the highest significance at 64 Mb.

Using linkage mapping alone, weak evidence of QTL (p=0.02) was detected at the 64 Mb region using Data I (FIG. 9A). This region was spanned by microsatellite markers ILSTS066 (74 cM) and BMS1216 (78 cM). The QTL was also detected by linkage mapping in the 60~70 Mb region using Data II (FIG. 9B). Segregation of a twinning rate QTL was previously identified within two North American Holstein families (Cruickshank et al. 2004) between 74 and 78 cM, corresponding to 64 to 70 Mb.

Figure 10:
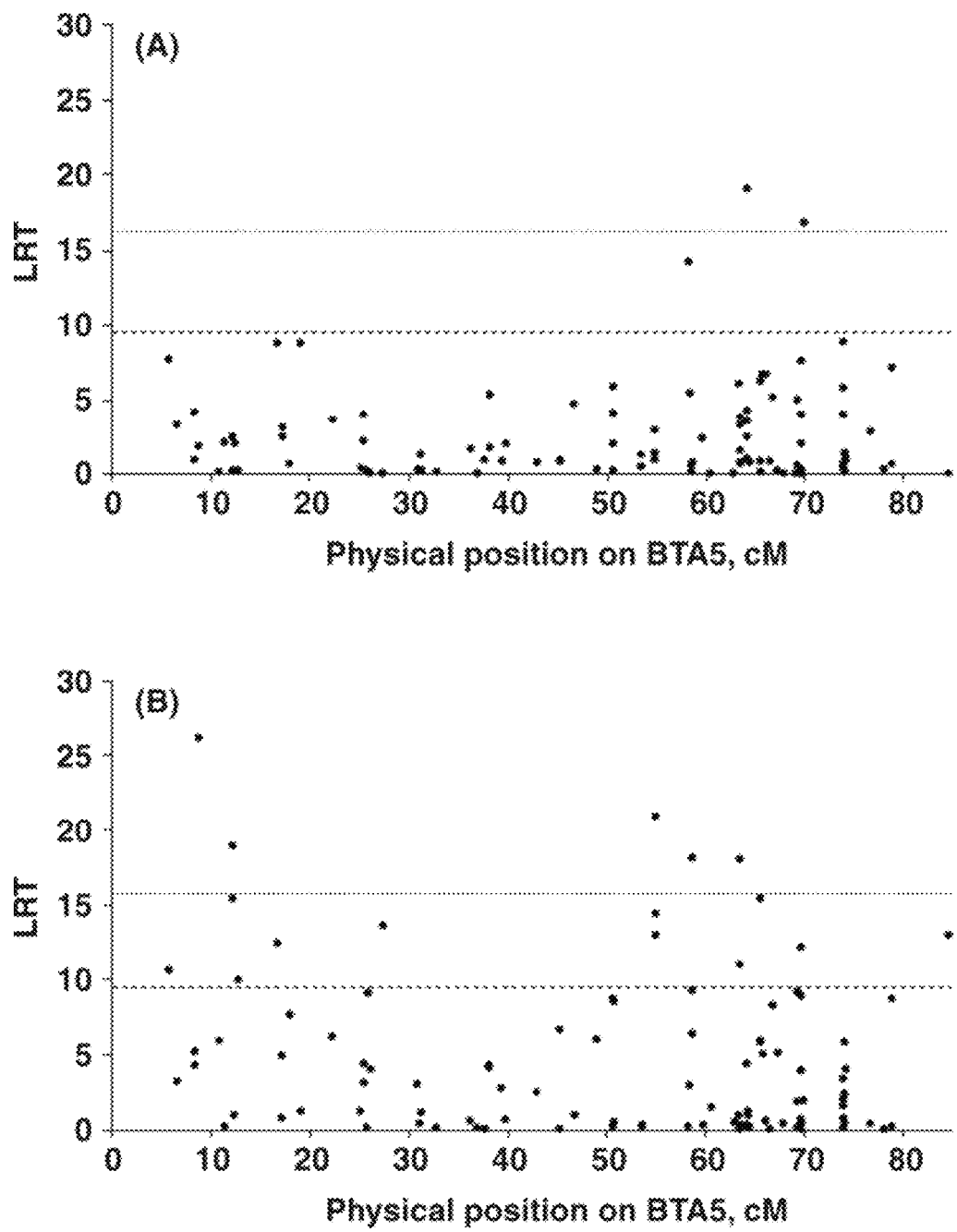
FIG. 10: Single marker association tests plotted against physical position of SNP on BTA5. (A) Results obtained using Data I; (B) Results obtained using Data II.

Regarding individual markers, one significant association ($p<2.3\times10^{-5}$) and two suggestive associations ($p<7.2\times10^4$) with twinning rate were observed between 5 Mb and 85 Mb on BTA5 using Data I. LD among these three SNPs was very weak ($r^2$~0.002) or slight ($r^2$<0.2). Using Data I, two significant SNP associations were located, one each within the IGF1 (64.2 Mb) and the COL10A1 (69.9 Mb) gene (FIG. 10A). The SNP in COL10A1 was located within 1.5 Mb from the maximum QTL peak detected by LLD for Data I (FIG. 10A). None of the SNPs between 5 Mb and 55 Mb on BTA5 were significantly associated with twinning rate using Data I (FIG. 10A). In contrast, significant ($p<2.3\times10^{-5}$) single marker associations were observed in this region using Data II (FIG. 10B). This analysis produced five significant single marker associations with twinning rate ($p<2.3\times10^{-5}$). Two such SNPs were located around the 5 Mb region. Three other SNPs were detected near the 60 Mb region on BTA5, within the genes INHBC, INHBE and SNRPF, respectively (FIG. 10B). None of these SNPs were significantly associated with twinning rate PTA in Data I (p<0.01). A total of sixteen suggestive associations ($p<7.2\times10^4$) were detected using either Data I or Data II; however, no suggestive associations in one data set were supported in the other data set at even a nominal p<0.05 level.

IGF1 was chosen for further examination as a candidate gene based on LLD results, single marker association results, and a known contribution to folliculogenesis (reviewed by Monget et al., 2002). Initial SNP discovery work focused on coding regions and revealed four SNPs. Additional SNP discovery efforts that completely covered the 72 kb region spanned by IGF1 revealed an additional eighteen SNPs (Table 3-3). Thirteen of these additional SNPs were successfully genotyped in the expanded set of bulls (Table 3-5), and none had genotype frequencies departing from expectation under Hardy-Weinberg equilibrium.

TABLE 3-5

Single-marker association tests of IGF1 SNP with twinning-rate predicted transmitting ability in the candidate gene analysis.

| SNP identification | Location, bp | Minor allele frequency | IGF1-data I (n = 309) | | IGF1-data II (n = 848) | |
|---|---|---|---|---|---|---|
| | | | Effect | P-value | Effect | P-value |
| SNP2 | 64270644 | 0.46 | 0.035 | 0.003 | 0.039 | $1.05 \times 10^{-6}$ |
| SNP3 | 64241296 | 0.21 | −0.025 | 0.082 | −0.026 | 0.005 |
| SNP4 | 64237899 | 0.21 | −0.026 | 0.075 | −0.023 | 0.018 |
| SNP5 | 64236951 | 0.39 | 0.052 | $2.66 \times 10^{-6}$ | 0.016 | 0.034 |
| SNP9 | 64226917 | 0.22 | −0.029 | 0.063 | −0.003 | 0.727 |
| SNP10 | 64226056 | 0.36 | 0.034 | 0.013 | −0.021 | 0.014 |
| SNP11 | 64223363 | 0.03 | −0.057 | 0.24 | −0.032 | 0.135 |
| SNP12 | 64220270 | 0.36 | 0.061 | $2.75 \times 10^{-7}$ | 0.012 | 0.1 |
| SNP14 | 64215386 | 0.36 | −0.052 | $1.33 \times 10^{-4}$ | 0.019 | 0.029 |
| SNP16 | 64213395 | 0.36 | −0.056 | $2.95 \times 10^{-5}$ | 0.022 | 0.009 |
| SNP17 | 64211268 | 0.15 | 0.019 | 0.282 | −0.022 | 0.038 |
| SNP18 | 64208267 | 0.36 | 0.057 | $3.17 \times 10^{-5}$ | −0.021 | 0.013 |
| SNP19 | 64202520 | 0.44 | 0.059 | $9.14 \times 10^{-7}$ | 0.015 | 0.048 |

[1]Effects are expressed in the underlying threshhold model liability scale, which has no units. An effect of 0.03 would correspond to an increase in twinning rate of approximately 0.6%.

Bovine IGF1 consists of four exons of 60, 182, 157, and 63 bp. The size of introns 1, 2 and 3 are 4475, 51274 bp, and 15229 bp respectively. Of the thirteen successfully genotyped SNPs, seven SNPs were located in intron 2, five were located in intron 3, and one was located very close to the 3' UTR region. No SNPs were discovered in IGF1 exons.

A consistent, significant association with twinning rate PTA (p=0.003 and p=$1.05 \times 10^{-6}$, for IGF1-Data I and IGF1-Data II, respectively) was identified for IGF1 SNP2, located in intron 2. The allele substitution effect of G to A for IGF SNP2 was associated with a reduction of twinning rate and the direction of the effect was consistent between the two data sets (Table 3-5). Likewise, SNPs 5 and 19 were also associated with twinning rate in both sets of data with a consistent sign of the effect. However, in both cases the association in IGF1-Data II was only nominal (p<0.05), and other SNPs in high LD with these two (SNPs 12, 14, 16 and 18) exhibited lesser significance or inconsistent effects. The remaining SNPs were either not significantly associated or had allele substitution effect estimates of opposite sign from the two data sets (Table 3-5). Associations of IGF1 SNP 2 with lactation or production traits was not significant (p>0.05). SNP2 was not located in a known regulatory sequence or a region highly conserved across species, suggesting it is a marker in high LD with the underlying, functional polymorphism.

Figure 11:
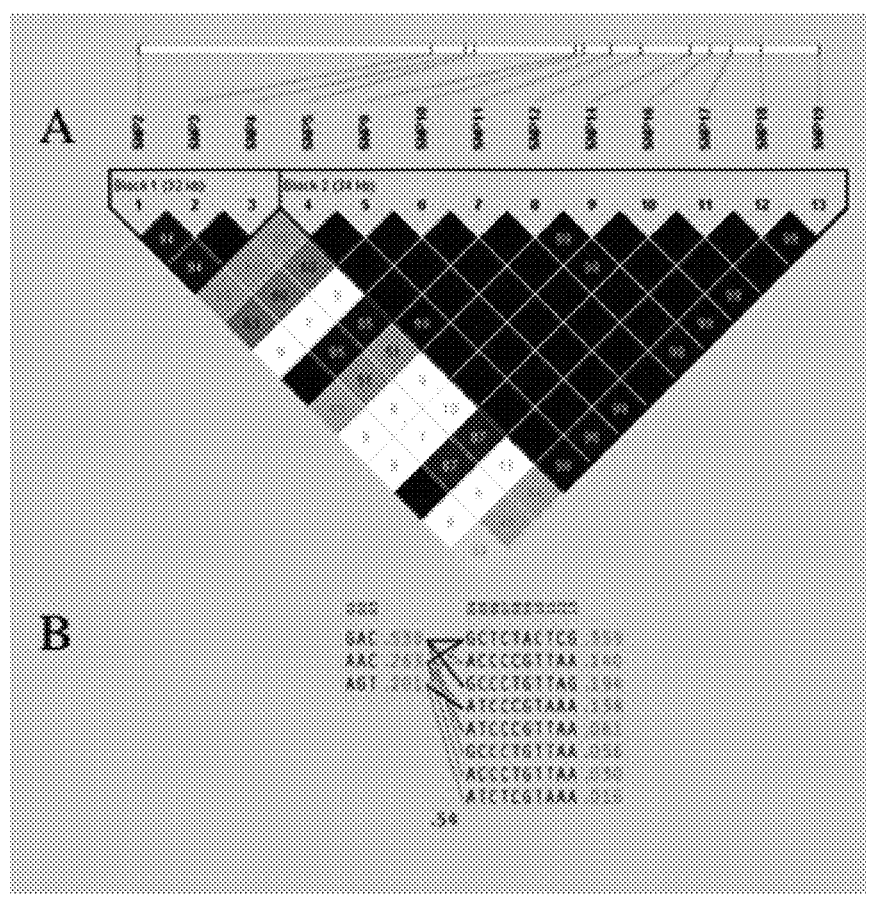
FIG. 11. Haplotype block structure of the IGF1 gene. (A) The approximate physical location of each SNP is shown at the top of the figure, and pairwise LD (D') values are indicated in the triangular figure below. Increasing LD is indicated with darker fill. Two haplotype blocks were observed within the IGF1 locus. (B) The frequency of haplotypes within each block are shown together with the multiallelic D' between the two blocks (0.54). GCTC-TACTCG (SEQ ID NO:371); ACCCCGTTAA (SEQ ID NO:372); GCCCTGTTAG (SEQ ID NO:373); ATCCCG-TAAA (SEQ ID NO:374); GCCCTGTTAA (SEQ ID NO:375); ACCCTGTTAA (SEQ ID NO:376); ATCTCG-TAAA (SEQ ID NO:377).

Two haplotype blocks (Wang et al. 2002) were detected in IGF1 using the D' measure of linkage disequilibrium (FIG. 11). Multiple haplotypes were observed within each block. One haplotype block spanned SNP2, 3 and 4 in intron2 (Haploblock1) and another haplotype block extended from SNP5 to SNP19 in introns 2 and 3 and the 3' downstream region (Haploblock 2) of IGF1. Haploblocks 1 and 2 are distinguished by historical recombination in the middle of intron 2.

REFERENCES

Abel K., Reneland R., Kammerer S., Mah S., Hoyal C., Cantor C. R., Nelson M. R. & Braun A. (2006) Genome-wide SNP association: Identification of susceptibility alleles for osteoarthritis. *Autoimmunity Reviews* 5, 258-63.

Allan, M. F., L. A. Kuehn, R. A. Cushamn, W. M. Snelling, S. E. Echternkamp, and R. M. Thallman. 2008. Confirmation of QTL using a low density SNP map for twinning and ovulation rate on bovine chromosome 5. *J. Animal Science* (in press).

Allan M. F., Thallman R. M., Cushman R. A., Echternkamp S. E., Kuehn L. A. & Snelling W. M. (2007) Fine mapping of QTL for twinning and ovulation rate using low density SNP map in conjunction with microsatellites marker information in the USMARC twinning population. *Plant and Animal Genome XV*, San Diego, Calif.

Andersson L. & Georges M. (2004) Domestic-Animal Genomics: Deciphering the genetics of complex traits. *Nature Review Genetics* 5, 202-12.

Arias J A. Kirkpatrick B W (2004) Mapping of bovine ovulation rate QTL using three generation pedigrees. *Animal Genetics* 35, 7-13.

Barrett J C, Fry B, Maller J, Daly M J (2004) Haploview: analysis and visualization of LD and haplotype maps. *Bioinformatics* 21, 263-265.

Barrett J C, Cardon L R (2006) Evaluating coverage of genome-wide association studies. *Nature Genetics* 38, 659-662.

Beerepoot G. M., Dykhuizen A. A., Nielen M. & Schukken Y. H. (1992) The economics of naturally occurring twinning in dairy cattle. *Journal of Dairy Science* 75, 1044-51.

Blattman A N, Kirkpatrick B W, Gregory K E (1996) A search for quantitative trait loci for ovulation rate in cattle. *Animal Genetics* 27, 157-162.

Calus M. P. L., Meuwissen T. H. E., de Roos A. P. W. & Veerkamp R. F. (2008) Accuracy of genomic selection using different methods to define haplotypes. *Genetics* 178, 553-61.

Chiu Y E, Liu S Y, Tsai Y Y (2005) A comparison in association and linkage genome-wide scans for alcoholism susceptibility genes using single-nucleotide polymorphisms. *BMC Genetics* 6, Supplement 1:S89.

Cobanoglu O, Berger P J, Kirkpatrick B W (2005) Genome screen for twinning rate QTL in four North American Holstein families. *Animal Genetics* 36, 303-308.

Cruickshank J., Dentine M., Berger P. J. & Kirkpatrick B. W. (2004) Evidence for quantitative trait loci affecting twinning rate in North American Holstein cattle. *Animal Genetics* 35, 206-12.

Draper N. R. & Smith H. (1981) Applied regression analysis. Second edition. New York: John Wiley and Sons, Inc.

Echternkamp S. E., Spicer L. J., Gregory K. E., Canning S. F. & Hammond J. M. (1990) Concentrations of insulin-like growth factor-I in blood and ovarian follicular fluid of cattle select for twins. *Biology of Reproduction* 43, 8-14.

Eddy R. G., Davies O. & David C. (1991) An economic assessment of twin births in British dairy herds. *Veterinary Record* 129, 526-9.

Ehrenreich I M, Stafford P A, Purugganna M D (2007) The genetic architecture of shoot branching in *Arabidopsis thaliana*: a comparative assessment of candidate gene associations vs. quantitative trait locus mapping. *Genetics* 176, 1223-1236.

Fricke P. M. & Wiltbank M. C. (1999) Effect of milk production on the incidence of double ovulation in dairy cows. *Theriogenology* 52, 1133-43.

Gilmour A R, Gogel B J, Cullis B R, Welham S J, Thompson R (2002) *ASReml User Guide Release* 1.0.

Goddard M. E., Hayes B. J., McPartlan A. & Chamberlain J. (2006) Can the same genetic markers be used in multiple breeds? *Proc. 8th World. Congr. Genet. Appl. Livest. Prod.* Belo Horizonte, Brazil.

Gonda M G, Arias J A, Shook G W, Kirkpatrick B W (2004) Identification of an ovulation rate QTL in cattle on BTA14 using selective DNA pooling and interval mapping. *Animal Genetics* 35, 298-304.

Grapes L, Dekkers C M, Rothschild M F, Fernando R L (2004) Comparing linkage disequilibrium-based methods for fine mapping quantitative trait loci. *Genetics* 166, 1561-1570.

Green P, Falls K, Crook S (1990) Documentation for CRI-MAP. version 2.4.

Gregory K E, Bennett G L, Van Vleck L D, Echternkamp S E, Cundiff L V (1997) Genetic and environmental parameters for ovulation rate, twinning rate, and environmental parameters for ovulation rate, twinning rate and weight traits in a cattle population selected for twinning *Journal of Animal Science* 75, 1213-1222.

Grisart B, Coppieters W, Famir F, Karim L, Ford C et al. (2002) Positional candidate cloning of a QTL in dairy cattle: Identification of a missense mutation in the bovine DGAT1 gene with major effect on milk yield and composition. *Genome Research* 12. 222-231.

Hampe J, Franke A, Rosentiel P, Till A, Teuber M et al. (2007) A genome-wide association scan of nonsynonymous SNPs identifies a susceptibility variant for Crohn's disease in ATG16L1. *Nature Genetics* 39, 207-211.

Hardenbol P., Yu F. L., Belmont J., MacKenzie J., Bruckner C., Brundage T., Boudreau A., Chow S., Eberle J. & Erbilgin A. (2005) Highly multiplexed molecular inversion probe genotyping: over 10,000 targeted SNPs genotyped in a single tube assay. *Genome Research* 15, 269-75.

Hayes B J, Chamberlain A, Goddard M E (2006) Use of linkage markers in linkage disequilibrium with QTL in breeding programs. *Proceedings of the 8th World Congress of Genetics Applied to Livestock Production.*

Hayes B. J., Visscher P., McPartlan H. & Goddard M. E. (2003) Novel Multilocus Measure of linkage disequilibrium to estimate past effective population size. *Genome Research* 13, 635-43.

Hayes B J, Goddard M E (2001) The distribution of the effects of genes affecting quantitative traits in livestock. *Genetics Selection Evolution* 33, 209-229.

Hirschhorn J. N. & Daly M. J. (2005) Genome-wide association studies for common diseases and complex traits. *Nature Review Genetics* 6, 95-108.

Johanson J M, Berger P J, Kirkpatrick B W, Dentine M R (2001) Twinning rates for North American Holstein. *Journal Dairy Science* 84, 2081-2088.

Kappes S M, Benne G L, Keele J W, Echtemkamp S E, Gregory K E, Thallman R M (2000) Initial results of genomic scans for ovulation rate in a cattle population selected for increased twinning rate. *Journal of Animal Science* 78, 3053-3059.

Karlsen A., Ruane J., Klemetsdal G. & Heringstad B. (2000) Twinning rate in Norwegian cattle: frequency, (co)variance components, and genetic trends. *Journal of Animal Science* 78, 15-20.

Kirkpatrick B W, Byla B M, Gregory K E (2000) Mapping quantitative trait loci for bovine ovulation rate. *Mammalian Genome* 11, 136-139.

Lander E. S. & Kruglyak L. (1995) Genetic dissection of complex traits: guidelines for interpreting and reporting linkage results. *Nature Genetics* 11, 241-7.

Lien S., Karlsen A., Klemetsdal G. et al. (2000) A primary screen of the bovine genome for quantitative trait loci affecting twinning rate. *Mammalian Genome* 11, 877-82.

Lynch M. & Walsh B. (1998) *Genetics and Analysis of Quantitative Traits.* Sinauer Associates, Sunderland, Mass.

Markusfeld O. (1987) Periparturient traits in seven high dairy herds. Incidence rates, association with parity, and interrelationships among traits. *Journal of Dairy Science* 60, 158-66.

Maestrini E., Pagnamenta A. T., Lamb J. A., Bacchelli E., Sykes N. H., Sousa I., Toma C., Barnby G., Butler H., Winchester L., Scerri T. S., Minopoli F., Reichert J., Cai G., Buxbaum J. D., Korvatska O., Schellenberg G. D., Dawson G., de Bildt A., Minderaa R. B., Mulder E. J., Morris A. P., Bailey A. J. & Monaco A. P. (2009) High-density SNP association study and copy number variation analysis of the AUTS1 and AUTS5 loci implicate the IMMP2L-DOCK4 gene region in autism susceptibility. *Molecular Psychiatry* 1-15.

Meuwissen T. H. E. & Goddard M. E. (2001) Prediction of identity by descent probabilities from marker-haplotypes. *Genetics Selection Evolution* 33, 605-34.

Meuwissen T. H. E., Karlsen A., Lien S., Olsaker I. & Goddard M. E. (2002) Fine mapping of a quantitative trait locus twinning rate using combined linkage and linkage disequilibrium mapping. *Genetics* 161, 373-9.

Meuwissen T H E, Goddard M E (2001) Prediction of identity by descent probabilities from marker-haplotypes. *Genetics Selection Evolution* 33, 605-634.

Meuwissen T H E, Hayes B J, Goddard M E (2001) Prediction of total genetic value using genome-wide dense marker maps. *Genetics* 157, 1819-1829.

Monget, P., S. Fabre, P. Mulsant, F. Lecerf, J.-M. Elsen, S. Mazerbourg, C. Pisselet and D Monniaux. (2002) Regulation of ovarian folliculogenesis by IGF and BMP system in domestic animals. *Domestic Animal Endocrinology* 23:139-54.

Nezer C, Collette C, Moreau L, Brouwers B, Kim J J et al. (2003) Haplotype sharing refines the location of an imprinted quantitative trait locus with major effect on muscle mass to a 250-kb chromosome segment containing the porcine IGF2 gene. *Genetics* 165, 277-285.

Nielen M., Schukken Y. H., Scholl D. T., Wilbrink H. J. & Brand A. (1989) Twinning in dairy cattle: A study of risk factors and effects. *Theriogenology* 32, 845-62.

Rioux J D, Xavier R J, Taylor K D, Silverberg M S, Goyette A et al. (2007) Genome-wide association study identifies new susceptibility loci for Crohn disease and implicates autophagy in disease pathogenesis. *Nature Genetics* 39, 596-604.

Risch N, Merikangas K (1996) The future of genetic studies of complex human diseases. *Science* 273, 1516-1517.

Ron, M., E. Ezra & Weller J. I. (1990) Genetic analysis of twinning rate in Israeli Holstein cattle. *Genetics Selection Evolution* 22, 349-59.

Sobel E., Papp J. C. & Lange K. (2002) Detection and integration of genotyping errors in statistical genetics. *American Journal of Human Genetics* 70, 496-508.

Sobel E. & Lange K. (1996) Descent graphs in pedigree analysis: applications to haplotyping, location scores, and marker sharing statistics. *American Journal of Human Genetics* 58, 1323-37.

Sved J A (1971) Linkage disequilibrium and homozygosity of chromosome segment in finite populations. *Theoretical Population Biology* 2, 125-141.

Thomas D C (2006) Are we ready for genome-wide association studies? *Cancer Epidemiology Biomarkers & Prevention* 15, 595-598.

VanRaden P. M., Van Tassell C. P., Wiggans G. R., Sonstegard T. S., Schnabel R. D., Taylor J. F. & Schenkel F. S. (2009) Invited Review: Reliability of genomic predictions for North American Holstein bulls. *Journal of Dairy Science* 92, 16-24.

Wang, N., J. M. Akey, K. Zhung, R. Chakraborty and L. Jin. 2002. Distribution of recombination crossovers and the origin of haplotype blocks: the interplay of population history, recombination, and mutation.

Wang W Y, Barratt B J, Clayton D G, Todd J A (2005) Genome-wide association studies: Theoretical and practical concerns. *Nature Review Genetics* 6, 109-118.

Weller J I, Song J Z, Heyen D W, Lewin H A, Ron M (1998) A new approach to the problem of multiple comparisons in the genetic dissection of complex trait. *Genetics* 150, 1699-1706.

Windig J J, Meuwissen T H E (2004) Rapid haplotype reconstruction in pedigrees with dense marker maps. *Journal of Animal Breeding and Genetics* 121, 26-39.

Zimin A. V., Delcher A. L., Florea L., Kelley D. R., Schatz M. C., Puiu D., Hanrahan F., Pertea G., Van Tassell C. P., Sonstegard T. S., Marçais G., Roberts M., Subramanian P., Yorke J. A. & Salzberg S. L. (2009) A whole-genome assembly of the domestic cow, *Bos taurus. Genome Biology* 10, 42.1-10.

In the specification, there have been disclosed typical preferred embodiments of the invention. Although specific terms are employed, they are used in a generic and descriptive sense only and not for purposes of limitation. The scope of the invention is set forth in the appended claims. Modifications and variations of the invention are possible in light of the above teachings. It is therefore to be understood that within the scope of the appended claims the invention may be practiced otherwise than as specifically described.

What is claimed is:

1. A method for identifying and breeding a member of a bovine population with a decreased likelihood of twinning, comprising the steps of:
   a) extracting a deoxyribonucleic acid (DNA) sample from a member of the bovine population;
   b) detecting, in the DNA sample, the presence of an A allele at nucleotide position 64270644 on bovine chromosome 5 (BTA5), wherein the detecting comprises a laboratory analysis or a field test which utilizes allele-specific polymerase chain reaction (PCR), a nucleic acid probe that specifically binds to the allele, or single-base primer extension;
   c) identifying said member of the bovine population as a member of the bovine population with decreased likelihood of twinning; and
   d) breeding said member of the bovine population with another bovine animal.

2. The method of claim 1, wherein step b) further comprises a statistical calculation to estimate likelihood of twinning.

3. The method of claim 1, wherein the laboratory analysis comprises a competitive allele-specific polymerase chain reaction.

4. The method of claim 1, wherein the laboratory analysis comprises single-base primer extension followed by mass spectrometry detection.

5. The method of claim 1, wherein step b) further comprises detecting, in the DNA sample, the presence of one or more additional alleles, wherein the additional alleles are:
   i) allele A located at nucleotide position 64241296 of BTA5; or
   ii) allele C located at nucleotide position 64237899 of BTA5; or
   iii) allele A located at nucleotide position 64236951 of BTA5; or
   iv) allele T located at nucleotide position 64220270 of BTA5; or
   v) allele A located at nucleotide position 64202520 of BTA5; or
   vi) allele C located at nucleotide position 64226917 of BTA5; or
   vii) allele C located at nucleotide position 64223363 of BTA5; or
   viii) any combination of (i)-(vii).

6. The method of claim 5, further comprising detecting, in the DNA sample, the presence of at least two of the additional alleles.

7. The method of claim 6, further comprising detecting, in the DNA sample the presence of at least three of the additional alleles.

8. The method of claim 1, wherein step b) further comprises detecting, in the DNA sample, the presence of allele A located at nucleotide position 64241296 of BTA5 and allele C located at nucleotide position 64237899 of BTA5.

* * * * *

```
                             SEQUENCE LISTING

<160> NUMBER OF SEQ ID NOS: 377

<210> SEQ ID NO 1
<211> LENGTH: 22
<212> TYPE: DNA
<213> ORGANISM: Bos taurus

<400> SEQUENCE: 1
ttcaactact ccggcctaac tc                                              22

<210> SEQ ID NO 2
<211> LENGTH: 22
<212> TYPE: DNA
<213> ORGANISM: Bos taurus

<400> SEQUENCE: 2
agcaagtgac tgagtccaag ag                                              22

<210> SEQ ID NO 3
<211> LENGTH: 22
<212> TYPE: DNA
<213> ORGANISM: Bos taurus

<400> SEQUENCE: 3
tcagtcctag agaagtccct ta                                              22

<210> SEQ ID NO 4
<211> LENGTH: 22
<212> TYPE: DNA
<213> ORGANISM: Bos taurus

<400> SEQUENCE: 4
ctaatgaaga actctgacac cc                                              22

<210> SEQ ID NO 5
<211> LENGTH: 22
<212> TYPE: DNA
<213> ORGANISM: Bos taurus

<400> SEQUENCE: 5
ccattcccat ctgattttga gt                                              22

<210> SEQ ID NO 6
<211> LENGTH: 23
<212> TYPE: DNA
<213> ORGANISM: Bos taurus

<400> SEQUENCE: 6 gggattttc aaaggacact aca                                              23

<210> SEQ ID NO 7
<211> LENGTH: 23
<212> TYPE: DNA
<213> ORGANISM: Bos taurus

<400> SEQUENCE: 7
acctgtctct gcaattcaaa gtc                                             23
```

<210> SEQ ID NO 8
<211> LENGTH: 23
<212> TYPE: DNA
<213> ORGANISM: Bos taurus

<400> SEQUENCE: 8
gtattctccc tacaccgaaa tca                                            23

<210> SEQ ID NO 9
<211> LENGTH: 22
<212> TYPE: DNA
<213> ORGANISM: Bos taurus

<400> SEQUENCE: 9
aatggaaaca agattgggac ag                                             22

<210> SEQ ID NO 10
<211> LENGTH: 22
<212> TYPE: DNA
<213> ORGANISM: Bos taurus

<400> SEQUENCE: 10
tccttatctg tcctcccaca gt                                             22

<210> SEQ ID NO 11
<211> LENGTH: 22
<212> TYPE: DNA
<213> ORGANISM: Bos taurus

<400> SEQUENCE: 11
aatgttcctt ccagtggagt tc                                             22

<210> SEQ ID NO 12
<211> LENGTH: 22
<212> TYPE: DNA
<213> ORGANISM: Bos taurus

<400> SEQUENCE: 12
aaactgtcca agaagatggg ag                                             22

<210> SEQ ID NO 13
<211> LENGTH: 22
<212> TYPE: DNA
<213> ORGANISM: Bos taurus

<400> SEQUENCE: 13
gtgatttttc tctgccctct cc                                             22

<210> SEQ ID NO 14
<211> LENGTH: 22
<212> TYPE: DNA
<213> ORGANISM: Bos taurus

<400> SEQUENCE: 14
tcttgaaact ccgactggac tg                                             22

<210> SEQ ID NO 15
<211> LENGTH: 22
<212> TYPE: DNA
<213> ORGANISM: Bos taurus

<400> SEQUENCE: 15
atttgggccg ggtcttaagt tc                                             22

<210> SEQ ID NO 16
<211> LENGTH: 22
<212> TYPE: DNA
<213> ORGANISM: Bos taurus

<400> SEQUENCE: 16
aagcagcaaa tccttgaggg ac                                              22

<210> SEQ ID NO 17
<211> LENGTH: 21
<212> TYPE: DNA
<213> ORGANISM: Bos taurus

<400> SEQUENCE: 17
ccacctgtga ggacagcaaa g                                               21

<210> SEQ ID NO 18
<211> LENGTH: 21
<212> TYPE: DNA
<213> ORGANISM: Bos taurus

<400> SEQUENCE: 18
tacctcaagc tccgtgacca g                                               21

<210> SEQ ID NO 19
<211> LENGTH: 22
<212> TYPE: DNA
<213> ORGANISM: Bos taurus

<400> SEQUENCE: 19
gacacgtatg atgcaagaag ga                                              22

<210> SEQ ID NO 20
<211> LENGTH: 22
<212> TYPE: DNA
<213> ORGANISM: Bos taurus

<400> SEQUENCE: 20
ccatttaaag gcagtgagga gt                                              22

<210> SEQ ID NO 21
<211> LENGTH: 22
<212> TYPE: DNA
<213> ORGANISM: Bos taurus

<400> SEQUENCE: 21
gactcagtac caccagtgtc ca                                              22

<210> SEQ ID NO 22
<211> LENGTH: 22
<212> TYPE: DNA
<213> ORGANISM: Bos taurus

<400> SEQUENCE: 22
tggctggggt atttataacc tg                                              22

<210> SEQ ID NO 23
<211> LENGTH: 21
<212> TYPE: DNA
<213> ORGANISM: Bos taurus

<400> SEQUENCE: 23
aaaagcctga ggagcctagt g                                          21

<210> SEQ ID NO 24
<211> LENGTH: 21
<212> TYPE: DNA
<213> ORGANISM: Bos taurus

<400> SEQUENCE: 24
gaggcatttg ctctgagatt g                                          21

<210> SEQ ID NO 25
<211> LENGTH: 21
<212> TYPE: DNA
<213> ORGANISM: Bos taurus

<400> SEQUENCE: 25
tcttctctcc ccagactttc c                                          21

<210> SEQ ID NO 26
<211> LENGTH: 21
<212> TYPE: DNA
<213> ORGANISM: Bos taurus

<400> SEQUENCE: 26
tggcctagca aactagcaag a                                          21

<210> SEQ ID NO 27
<211> LENGTH: 22
<212> TYPE: DNA
<213> ORGANISM: Bos taurus

<400> SEQUENCE: 27
agggtacaga gccagatgga ta                                         22

<210> SEQ ID NO 28
<211> LENGTH: 22
<212> TYPE: DNA
<213> ORGANISM: Bos taurus

<400> SEQUENCE: 28
tgctcaatct tctcaaggtc aa                                         22

<210> SEQ ID NO 29
<211> LENGTH: 22
<212> TYPE: DNA
<213> ORGANISM: Bos taurus

<400> SEQUENCE: 29
ccttcaactt taccctcatc tc                                         22

<210> SEQ ID NO 30
<211> LENGTH: 22
<212> TYPE: DNA
<213> ORGANISM: Bos taurus

<400> SEQUENCE: 30
cgtaggaaga ctgagatgac tg                                         22

<210> SEQ ID NO 31
<211> LENGTH: 22
<212> TYPE: DNA
<213> ORGANISM: Bos taurus

<400> SEQUENCE: 31
tgtaaagcct ggaatatggt tg                                              22

<210> SEQ ID NO 32
<211> LENGTH: 23
<212> TYPE: DNA
<213> ORGANISM: Bos taurus

<400> SEQUENCE: 32
gatcttacga agtctctctc cac                                             23

<210> SEQ ID NO 33
<211> LENGTH: 22
<212> TYPE: DNA
<213> ORGANISM: Bos taurus

<400> SEQUENCE: 33
ctgcccacta aattctctac cc                                              22

<210> SEQ ID NO 34
<211> LENGTH: 21
<212> TYPE: DNA
<213> ORGANISM: Bos taurus

<400> SEQUENCE: 34
agcatcttgg acaagctgca c                                               21

<210> SEQ ID NO 35
<211> LENGTH: 24
<212> TYPE: DNA
<213> ORGANISM: Bos taurus

<400> SEQUENCE: 35
gatgatctca tactcctgtc cctc                                            24

<210> SEQ ID NO 36
<211> LENGTH: 24
<212> TYPE: DNA
<213> ORGANISM: Bos taurus

<400> SEQUENCE: 36
acatgacaat gacctacagt gtcc                                            24

<210> SEQ ID NO 37
<211> LENGTH: 23
<212> TYPE: DNA
<213> ORGANISM: Bos taurus

<400> SEQUENCE: 37
gagcatggtc tgttcaggtg gta                                             23

<210> SEQ ID NO 38
<211> LENGTH: 23
<212> TYPE: DNA
<213> ORGANISM: Bos taurus

<400> SEQUENCE: 38
acttgtccat gcagttcaaa cct                                             23

<210> SEQ ID NO 39
<211> LENGTH: 22
<212> TYPE: DNA
<213> ORGANISM: Bos taurus

```
<400> SEQUENCE: 39
tgagcactgt tgagatttcc ta                                              22

<210> SEQ ID NO 40
<211> LENGTH: 21
<212> TYPE: DNA
<213> ORGANISM: Bos taurus

<400> SEQUENCE: 40
ggtgggggta atcttgaat a                                                21

<210> SEQ ID NO 41
<211> LENGTH: 23
<212> TYPE: DNA
<213> ORGANISM: Bos taurus

<400> SEQUENCE: 41
gtgcatgaga ggattttgag ggt                                             23

<210> SEQ ID NO 42
<211> LENGTH: 24
<212> TYPE: DNA
<213> ORGANISM: Bos taurus

<400> SEQUENCE: 42
ggaaatctca acagtgctca aaac                                            24

<210> SEQ ID NO 43
<211> LENGTH: 22
<212> TYPE: DNA
<213> ORGANISM: Bos taurus

<400> SEQUENCE: 43
aattcttgaa ccagctttat cc                                              22

<210> SEQ ID NO 44
<211> LENGTH: 22
<212> TYPE: DNA
<213> ORGANISM: Bos taurus

<400> SEQUENCE: 44
aagtccattt tatctccaag ca                                              22

<210> SEQ ID NO 45
<211> LENGTH: 22
<212> TYPE: DNA
<213> ORGANISM: Bos taurus

<400> SEQUENCE: 45
gaaaatacca tgagcagagg ag                                              22

<210> SEQ ID NO 46
<211> LENGTH: 23
<212> TYPE: DNA
<213> ORGANISM: Bos taurus

<400> SEQUENCE: 46
gcgactaaca ctttcacatt ttc                                             23

<210> SEQ ID NO 47
<211> LENGTH: 22
<212> TYPE: DNA
<213> ORGANISM: Bos taurus
```

<400> SEQUENCE: 47
atttctgttg ctggcagttt gg                                            22

<210> SEQ ID NO 48
<211> LENGTH: 22
<212> TYPE: DNA
<213> ORGANISM: Bos taurus

<400> SEQUENCE: 48
gaaagtgaag tcgctcagtc gt                                            22

<210> SEQ ID NO 49
<211> LENGTH: 23
<212> TYPE: DNA
<213> ORGANISM: Bos taurus

<400> SEQUENCE: 49
agtccatggg gtcgctaaga gtc                                           23

<210> SEQ ID NO 50
<211> LENGTH: 22
<212> TYPE: DNA
<213> ORGANISM: Bos taurus

<400> SEQUENCE: 50
aaaacacccc aatagccgag ga                                            22

<210> SEQ ID NO 51
<211> LENGTH: 23
<212> TYPE: DNA
<213> ORGANISM: Bos taurus

<400> SEQUENCE: 51
agaaatgatt cctaacttgc gtg                                           23

<210> SEQ ID NO 52
<211> LENGTH: 23
<212> TYPE: DNA
<213> ORGANISM: Bos taurus

<400> SEQUENCE: 52
tttttcacca tcttccagag ctt                                           23

<210> SEQ ID NO 53
<211> LENGTH: 23
<212> TYPE: DNA
<213> ORGANISM: Bos taurus

<400> SEQUENCE: 53
cacagatatg agtcccgacc cta                                           23

<210> SEQ ID NO 54
<211> LENGTH: 22
<212> TYPE: DNA
<213> ORGANISM: Bos taurus

<400> SEQUENCE: 54
tgggtgaagg tttcagagtg gt                                            22

<210> SEQ ID NO 55
<211> LENGTH: 23
<212> TYPE: DNA

```
<213> ORGANISM: Bos taurus

<400> SEQUENCE: 55
acagggttga acgtgaaatg gag                                     23

<210> SEQ ID NO 56
<211> LENGTH: 24
<212> TYPE: DNA
<213> ORGANISM: Bos taurus

<400> SEQUENCE: 56
cccataactc cactcaccaa aaca                                    24

<210> SEQ ID NO 57
<211> LENGTH: 22
<212> TYPE: DNA
<213> ORGANISM: Bos taurus

<400> SEQUENCE: 57
tggttttgaa ctgtcgtgct gg                                      22

<210> SEQ ID NO 58
<211> LENGTH: 23
<212> TYPE: DNA
<213> ORGANISM: Bos taurus

<400> SEQUENCE: 58
cagactgaaa cccccaaaac tcc                                     23

<210> SEQ ID NO 59
<211> LENGTH: 25
<212> TYPE: DNA
<213> ORGANISM: Bos taurus

<400> SEQUENCE: 59
gggcatagac aagatccttg actac                                   25

<210> SEQ ID NO 60
<211> LENGTH: 25
<212> TYPE: DNA
<213> ORGANISM: Bos taurus

<400> SEQUENCE: 60
tggtgattgg caaagctagg atgtc                                   25

<210> SEQ ID NO 61
<211> LENGTH: 25
<212> TYPE: DNA
<213> ORGANISM: Bos taurus

<400> SEQUENCE: 61
gaaatttgat tcatggtgtt ccctc                                   25

<210> SEQ ID NO 62
<211> LENGTH: 25
<212> TYPE: DNA
<213> ORGANISM: Bos taurus

<400> SEQUENCE: 62
aattgtcctc aaattcttag ccacc                                   25

<210> SEQ ID NO 63
<211> LENGTH: 25
```

<212> TYPE: DNA
<213> ORGANISM: Bos taurus

<400> SEQUENCE: 63
gctgccctaa gaatgacaat aaacc                                    25

<210> SEQ ID NO 64
<211> LENGTH: 25
<212> TYPE: DNA
<213> ORGANISM: Bos taurus

<400> SEQUENCE: 64
cacctttcat ttgattctga ttgcc                                    25

<210> SEQ ID NO 65
<211> LENGTH: 25
<212> TYPE: DNA
<213> ORGANISM: Bos taurus

<400> SEQUENCE: 65
ctgaaaccac ttctgccact ttacc                                    25

<210> SEQ ID NO 66
<211> LENGTH: 25
<212> TYPE: DNA
<213> ORGANISM: Bos taurus

<400> SEQUENCE: 66
tgatgcttgg cactgtaaag tgagg                                    25

<210> SEQ ID NO 67
<211> LENGTH: 22
<212> TYPE: DNA
<213> ORGANISM: Bos taurus

<400> SEQUENCE: 67
aagatgccca tcacatcctc ct                                       22

<210> SEQ ID NO 68
<211> LENGTH: 22
<212> TYPE: DNA
<213> ORGANISM: Bos taurus

<400> SEQUENCE: 68
tgtgcctttc agcgactttc ac                                       22

<210> SEQ ID NO 69
<211> LENGTH: 18
<212> TYPE: DNA
<213> ORGANISM: Bos taurus

<400> SEQUENCE: 69
gggaatgacg ttctggtt                                            18

<210> SEQ ID NO 70
<211> LENGTH: 20
<212> TYPE: DNA
<213> ORGANISM: Bos taurus

<400> SEQUENCE: 70
aactggagag catccaccaa                                          20

<210> SEQ ID NO 71

<211> LENGTH: 22
<212> TYPE: DNA
<213> ORGANISM: Bos taurus

<400> SEQUENCE: 71
gtgccacaag tagcaatgtg ga                                              22

<210> SEQ ID NO 72
<211> LENGTH: 23
<212> TYPE: DNA
<213> ORGANISM: Bos taurus

<400> SEQUENCE: 72
ggcatgtgca tccattactg acc                                             23

<210> SEQ ID NO 73
<211> LENGTH: 22
<212> TYPE: DNA
<213> ORGANISM: Bos taurus

<400> SEQUENCE: 73
tggagggttt ccatgaacag gt                                              22

<210> SEQ ID NO 74
<211> LENGTH: 22
<212> TYPE: DNA
<213> ORGANISM: Bos taurus

<400> SEQUENCE: 74
tgtggctcaa gtctccatcc tt                                              22

<210> SEQ ID NO 75
<211> LENGTH: 23
<212> TYPE: DNA
<213> ORGANISM: Bos taurus

<400> SEQUENCE: 75
atctgagaac ataactcagc aaa                                             23

<210> SEQ ID NO 76
<211> LENGTH: 22
<212> TYPE: DNA
<213> ORGANISM: Bos taurus

<400> SEQUENCE: 76
agaggaggtg aaagcttgat gg                                              22

<210> SEQ ID NO 77
<211> LENGTH: 22
<212> TYPE: DNA
<213> ORGANISM: Bos taurus

<400> SEQUENCE: 77
ataataccca ccctgacctg ct                                              22

<210> SEQ ID NO 78
<211> LENGTH: 26
<212> TYPE: DNA
<213> ORGANISM: Bos taurus

<400> SEQUENCE: 78
ctcagcaata cctatcagtc tctagc                                          26

```
<210> SEQ ID NO 79
<211> LENGTH: 22
<212> TYPE: DNA
<213> ORGANISM: Bos taurus

<400> SEQUENCE: 79
ctagtactgg gaggcagcaa ga                                        22

<210> SEQ ID NO 80
<211> LENGTH: 22
<212> TYPE: DNA
<213> ORGANISM: Bos taurus

<400> SEQUENCE: 80
gcacatggaa agagaaccaa ca                                        22

<210> SEQ ID NO 81
<211> LENGTH: 21
<212> TYPE: DNA
<213> ORGANISM: Bos taurus

<400> SEQUENCE: 81
ctagtgccca gcacagagaa a                                         21

<210> SEQ ID NO 82
<211> LENGTH: 21
<212> TYPE: DNA
<213> ORGANISM: Bos taurus

<400> SEQUENCE: 82
tttgagctgc caaaagagat g                                         21

<210> SEQ ID NO 83
<211> LENGTH: 22
<212> TYPE: DNA
<213> ORGANISM: Bos taurus

<400> SEQUENCE: 83
cagatggcta aattgaatca ac                                        22

<210> SEQ ID NO 84
<211> LENGTH: 20
<212> TYPE: DNA
<213> ORGANISM: Bos taurus

<400> SEQUENCE: 84
ctagccccac tcttcacttc                                           20

<210> SEQ ID NO 85
<211> LENGTH: 22
<212> TYPE: DNA
<213> ORGANISM: Bos taurus

<400> SEQUENCE: 85
tgtaatcagt ttgcaagtct gg                                        22

<210> SEQ ID NO 86
<211> LENGTH: 22
<212> TYPE: DNA
<213> ORGANISM: Bos taurus

<400> SEQUENCE: 86
gagttgctta aaccaatggg ac                                        22
```

```
<210> SEQ ID NO 87
<211> LENGTH: 22
<212> TYPE: DNA
<213> ORGANISM: Bos taurus

<400> SEQUENCE: 87
caactgcctc tcctcagcta at                                              22

<210> SEQ ID NO 88
<211> LENGTH: 22
<212> TYPE: DNA
<213> ORGANISM: Bos taurus

<400> SEQUENCE: 88
agacgtgtga ccttgggtaa gt                                              22

<210> SEQ ID NO 89
<211> LENGTH: 22
<212> TYPE: DNA
<213> ORGANISM: Bos taurus

<400> SEQUENCE: 89
gtaacagtgc gtgtgagagg ag                                              22

<210> SEQ ID NO 90
<211> LENGTH: 22
<212> TYPE: DNA
<213> ORGANISM: Bos taurus

<400> SEQUENCE: 90
gcaacctatg gacttgattt ga                                              22

<210> SEQ ID NO 91
<211> LENGTH: 22
<212> TYPE: DNA
<213> ORGANISM: Bos taurus

<400> SEQUENCE: 91
tgtgcttatg gaaggaaggt tt                                              22

<210> SEQ ID NO 92
<211> LENGTH: 22
<212> TYPE: DNA
<213> ORGANISM: Bos taurus

<400> SEQUENCE: 92
ttctgtgcct ttgcttgact aa                                              22

<210> SEQ ID NO 93
<211> LENGTH: 22
<212> TYPE: DNA
<213> ORGANISM: Bos taurus

<400> SEQUENCE: 93
tgaaatgtgc atcagggtta ag                                              22

<210> SEQ ID NO 94
<211> LENGTH: 22
<212> TYPE: DNA
<213> ORGANISM: Bos taurus

<400> SEQUENCE: 94
tgtgctttgg gcaagagtat tc                                              22
```

```
<210> SEQ ID NO 95
<211> LENGTH: 22
<212> TYPE: DNA
<213> ORGANISM: Bos taurus

<400> SEQUENCE: 95
acaccttact tgacctggaa ac                                              22

<210> SEQ ID NO 96
<211> LENGTH: 23
<212> TYPE: DNA
<213> ORGANISM: Bos taurus

<400> SEQUENCE: 96
caagccaacc ttacattaag aac                                             23

<210> SEQ ID NO 97
<211> LENGTH: 22
<212> TYPE: DNA
<213> ORGANISM: Bos taurus

<400> SEQUENCE: 97
ccgagaagga agctctgtaa tc                                              22

<210> SEQ ID NO 98
<211> LENGTH: 21
<212> TYPE: DNA
<213> ORGANISM: Bos taurus

<400> SEQUENCE: 98
gccattcctg cttttttcaat c                                              21

<210> SEQ ID NO 99
<211> LENGTH: 24
<212> TYPE: DNA
<213> ORGANISM: Bos taurus

<400> SEQUENCE: 99
gcctccaaat cttaattttc ttct                                            24

<210> SEQ ID NO 100
<211> LENGTH: 24
<212> TYPE: DNA
<213> ORGANISM: Bos taurus

<400> SEQUENCE: 100
tcccttaact ctgtagtagg aatg                                            24

<210> SEQ ID NO 101
<211> LENGTH: 22
<212> TYPE: DNA
<213> ORGANISM: Bos taurus

<400> SEQUENCE: 101
tcagcactga tctctccagt gt                                              22

<210> SEQ ID NO 102
<211> LENGTH: 22
<212> TYPE: DNA
<213> ORGANISM: Bos taurus

<400> SEQUENCE: 102
```
ccacacattt ccaagctaat ga                                              22

<210> SEQ ID NO 103
<211> LENGTH: 22
<212> TYPE: DNA
<213> ORGANISM: Bos taurus

<400> SEQUENCE: 103
aatggctaca gaaaatgcac ac                                              22

<210> SEQ ID NO 104
<211> LENGTH: 22
<212> TYPE: DNA
<213> ORGANISM: Bos taurus

<400> SEQUENCE: 104
caagggttgt gcaaaagtct tc                                              22

<210> SEQ ID NO 105
<211> LENGTH: 22
<212> TYPE: DNA
<213> ORGANISM: Bos taurus

<400> SEQUENCE: 105
gcaaatgcag actgaattga ac                                              22

<210> SEQ ID NO 106
<211> LENGTH: 22
<212> TYPE: DNA
<213> ORGANISM: Bos taurus

<400> SEQUENCE: 106
tgtgtgtaca tgtgggcata ag                                              22

<210> SEQ ID NO 107
<211> LENGTH: 21
<212> TYPE: DNA
<213> ORGANISM: Bos taurus

<400> SEQUENCE: 107
tcaggaagat cccttggaga g                                               21

<210> SEQ ID NO 108
<211> LENGTH: 22
<212> TYPE: DNA
<213> ORGANISM: Bos taurus

<400> SEQUENCE: 108
tgagagagga gtggacactg ag                                              22

<210> SEQ ID NO 109
<211> LENGTH: 20
<212> TYPE: DNA
<213> ORGANISM: Bos taurus

<400> SEQUENCE: 109
cttgtccatc ctccatcctc                                                 20

<210> SEQ ID NO 110
<211> LENGTH: 20
<212> TYPE: DNA
<213> ORGANISM: Bos taurus

<400> SEQUENCE: 110
caaaatcctc agcaaggcac                                                    20

<210> SEQ ID NO 111
<211> LENGTH: 22
<212> TYPE: DNA
<213> ORGANISM: Bos taurus

<400> SEQUENCE: 111
ttgggagtga gtggaagatg ag                                                 22

<210> SEQ ID NO 112
<211> LENGTH: 23
<212> TYPE: DNA
<213> ORGANISM: Bos taurus

<400> SEQUENCE: 112
aaccatccca gggtatttat gag                                                23

<210> SEQ ID NO 113
<211> LENGTH: 22
<212> TYPE: DNA
<213> ORGANISM: Bos taurus

<400> SEQUENCE: 113
tggttaactc atgttgctgg tc                                                 22

<210> SEQ ID NO 114
<211> LENGTH: 20
<212> TYPE: DNA
<213> ORGANISM: Bos taurus

<400> SEQUENCE: 114
aacaaaaccc acatgccacc                                                    20

<210> SEQ ID NO 115
<211> LENGTH: 23
<212> TYPE: DNA
<213> ORGANISM: Bos taurus

<400> SEQUENCE: 115
cgtcagccca tcaagtatgt aac                                                23

<210> SEQ ID NO 116
<211> LENGTH: 23
<212> TYPE: DNA
<213> ORGANISM: Bos taurus

<400> SEQUENCE: 116
ttcaataaat cctgagtgcc agt                                                23

<210> SEQ ID NO 117
<211> LENGTH: 22
<212> TYPE: DNA
<213> ORGANISM: Bos taurus

<400> SEQUENCE: 117
ggtgaatttg tccccagaga ac                                                 22

<210> SEQ ID NO 118
<211> LENGTH: 22
<212> TYPE: DNA
<213> ORGANISM: Bos taurus

<400> SEQUENCE: 118
catgacaaga ctggagggaa ga                    22

<210> SEQ ID NO 119
<211> LENGTH: 23
<212> TYPE: DNA
<213> ORGANISM: Bos taurus

<400> SEQUENCE: 119
tcgagtcatt ggcatcccta gta                   23

<210> SEQ ID NO 120
<211> LENGTH: 22
<212> TYPE: DNA
<213> ORGANISM: Bos taurus

<400> SEQUENCE: 120
ctttcttgac attcctgggc tt                    22

<210> SEQ ID NO 121
<211> LENGTH: 23
<212> TYPE: DNA
<213> ORGANISM: Bos taurus

<400> SEQUENCE: 121
tatagaggat aaagcggaga cac                   23

<210> SEQ ID NO 122
<211> LENGTH: 22
<212> TYPE: DNA
<213> ORGANISM: Bos taurus

<400> SEQUENCE: 122
aaagactcac ttgcccaata cc                    22

<210> SEQ ID NO 123
<211> LENGTH: 24
<212> TYPE: DNA
<213> ORGANISM: Bos taurus

<400> SEQUENCE: 123
tctgtaactc ggattgcttt cttg                  24

<210> SEQ ID NO 124
<211> LENGTH: 23
<212> TYPE: DNA
<213> ORGANISM: Bos taurus

<400> SEQUENCE: 124
gattgctgct taccagtctg tgt                   23

<210> SEQ ID NO 125
<211> LENGTH: 22
<212> TYPE: DNA
<213> ORGANISM: Bos taurus

<400> SEQUENCE: 125
gtcgaattgc atgattgaaa cc                    22

<210> SEQ ID NO 126
<211> LENGTH: 22
<212> TYPE: DNA
<213> ORGANISM: Bos taurus

```
<400> SEQUENCE: 126
gcggaacctt ttgtggctat ta                                          22

<210> SEQ ID NO 127
<211> LENGTH: 21
<212> TYPE: DNA
<213> ORGANISM: Bos taurus

<400> SEQUENCE: 127
tggatcactg gctgggacac t                                           21

<210> SEQ ID NO 128
<211> LENGTH: 23
<212> TYPE: DNA
<213> ORGANISM: Bos taurus

<400> SEQUENCE: 128
gttcagtagg cgtgtagtcc cag                                         23

<210> SEQ ID NO 129
<211> LENGTH: 23
<212> TYPE: DNA
<213> ORGANISM: Bos taurus

<400> SEQUENCE: 129
gctggctttg tcctgtgaag atg                                         23

<210> SEQ ID NO 130
<211> LENGTH: 23
<212> TYPE: DNA
<213> ORGANISM: Bos taurus

<400> SEQUENCE: 130
cgggaaggca ggtagattga ctc                                         23

<210> SEQ ID NO 131
<211> LENGTH: 23
<212> TYPE: DNA
<213> ORGANISM: Bos taurus

<400> SEQUENCE: 131
gctctccctt tgcgactttc tct                                         23

<210> SEQ ID NO 132
<211> LENGTH: 23
<212> TYPE: DNA
<213> ORGANISM: Bos taurus

<400> SEQUENCE: 132
tccagccttc acaacctacc act                                         23

<210> SEQ ID NO 133
<211> LENGTH: 23
<212> TYPE: DNA
<213> ORGANISM: Bos taurus

<400> SEQUENCE: 133
tcctggaatc gtgtgtgtgt gtg                                         23

<210> SEQ ID NO 134
<211> LENGTH: 23
<212> TYPE: DNA
```

```
<213> ORGANISM: Bos taurus

<400> SEQUENCE: 134
agggctagaa ccagtggaga gga                                            23

<210> SEQ ID NO 135
<211> LENGTH: 22
<212> TYPE: DNA
<213> ORGANISM: Bos taurus

<400> SEQUENCE: 135
atagctcatg cgtgccagga ct                                             22

<210> SEQ ID NO 136
<211> LENGTH: 23
<212> TYPE: DNA
<213> ORGANISM: Bos taurus

<400> SEQUENCE: 136
tctggctaca tcttctgggc tct                                            23

<210> SEQ ID NO 137
<211> LENGTH: 23
<212> TYPE: DNA
<213> ORGANISM: Bos taurus

<400> SEQUENCE: 137
ctgtggatga cctgatggga gtg                                            23

<210> SEQ ID NO 138
<211> LENGTH: 24
<212> TYPE: DNA
<213> ORGANISM: Bos taurus

<400> SEQUENCE: 138
acacagccac tttcccaact acct                                           24

<210> SEQ ID NO 139
<211> LENGTH: 22
<212> TYPE: DNA
<213> ORGANISM: Bos taurus

<400> SEQUENCE: 139
ccaaaccact gggacagtga gt                                             22

<210> SEQ ID NO 140
<211> LENGTH: 22
<212> TYPE: DNA
<213> ORGANISM: Bos taurus

<400> SEQUENCE: 140
ggaggtggaa gggatcacat aa                                             22

<210> SEQ ID NO 141
<211> LENGTH: 21
<212> TYPE: DNA
<213> ORGANISM: Bos taurus

<400> SEQUENCE: 141
gcgtccagtt cccagttcct t                                              21

<210> SEQ ID NO 142
<211> LENGTH: 22
```

```
<212> TYPE: DNA
<213> ORGANISM: Bos taurus

<400> SEQUENCE: 142
ggcttggctg ggtgttactg tc                                          22

<210> SEQ ID NO 143
<211> LENGTH: 22
<212> TYPE: DNA
<213> ORGANISM: Bos taurus

<400> SEQUENCE: 143
tttgaggaag agatcgtgtg tg                                          22

<210> SEQ ID NO 144
<211> LENGTH: 23
<212> TYPE: DNA
<213> ORGANISM: Bos taurus

<400> SEQUENCE: 144
agaagtgaat gtggcaaaag agt                                         23

<210> SEQ ID NO 145
<211> LENGTH: 22
<212> TYPE: DNA
<213> ORGANISM: Bos taurus

<400> SEQUENCE: 145
cctatgtcgt ttgaatcacc ac                                          22

<210> SEQ ID NO 146
<211> LENGTH: 22
<212> TYPE: DNA
<213> ORGANISM: Bos taurus

<400> SEQUENCE: 146
ccccctccat tataaagttt tc                                          22

<210> SEQ ID NO 147
<211> LENGTH: 22
<212> TYPE: DNA
<213> ORGANISM: Bos taurus

<400> SEQUENCE: 147
gagaatggat ggatggatga at                                          22

<210> SEQ ID NO 148
<211> LENGTH: 22
<212> TYPE: DNA
<213> ORGANISM: Bos taurus

<400> SEQUENCE: 148
gcattgcaga cagatgcttt ac                                          22

<210> SEQ ID NO 149
<211> LENGTH: 24
<212> TYPE: DNA
<213> ORGANISM: Bos taurus

<400> SEQUENCE: 149
caggctggtt atcattctgc tgtc                                        24

<210> SEQ ID NO 150
```

```
<211> LENGTH: 23
<212> TYPE: DNA
<213> ORGANISM: Bos taurus

<400> SEQUENCE: 150
atctgtaccc cacttccagc ctc                                              23

<210> SEQ ID NO 151
<211> LENGTH: 23
<212> TYPE: DNA
<213> ORGANISM: Bos taurus

<400> SEQUENCE: 151
gttatcattc tgctgtcccc tct                                              23

<210> SEQ ID NO 152
<211> LENGTH: 24
<212> TYPE: DNA
<213> ORGANISM: Bos taurus

<400> SEQUENCE: 152
taacaagatc tgtaccccac ttcc                                             24

<210> SEQ ID NO 153
<211> LENGTH: 22
<212> TYPE: DNA
<213> ORGANISM: Bos taurus

<400> SEQUENCE: 153
ccaccctctt cccttctaga tt                                               22

<210> SEQ ID NO 154
<211> LENGTH: 22
<212> TYPE: DNA
<213> ORGANISM: Bos taurus

<400> SEQUENCE: 154
ttagcttaag tgccagcttt cc                                               22

<210> SEQ ID NO 155
<211> LENGTH: 22
<212> TYPE: DNA
<213> ORGANISM: Bos taurus

<400> SEQUENCE: 155
aatgttggaa tcagcccttt ga                                               22

<210> SEQ ID NO 156
<211> LENGTH: 22
<212> TYPE: DNA
<213> ORGANISM: Bos taurus

<400> SEQUENCE: 156
gggaagaggg tgggatatag ac                                               22

<210> SEQ ID NO 157
<211> LENGTH: 22
<212> TYPE: DNA
<213> ORGANISM: Bos taurus

<400> SEQUENCE: 157
aaggtaacaa cgcctccttg ta                                               22
```

```
<210> SEQ ID NO 158
<211> LENGTH: 22
<212> TYPE: DNA
<213> ORGANISM: Bos taurus

<400> SEQUENCE: 158
catcatttgg aaaagggaga ag                                              22

<210> SEQ ID NO 159
<211> LENGTH: 22
<212> TYPE: DNA
<213> ORGANISM: Bos taurus

<400> SEQUENCE: 159
cacgtagatg accagggagt tg                                              22

<210> SEQ ID NO 160
<211> LENGTH: 23
<212> TYPE: DNA
<213> ORGANISM: Bos taurus

<400> SEQUENCE: 160
gggaaggaca cagtctatct cag                                             23

<210> SEQ ID NO 161
<211> LENGTH: 22
<212> TYPE: DNA
<213> ORGANISM: Bos taurus

<400> SEQUENCE: 161
caccaggaaa tagaggccga ag                                              22

<210> SEQ ID NO 162
<211> LENGTH: 23
<212> TYPE: DNA
<213> ORGANISM: Bos taurus

<400> SEQUENCE: 162
gcattctgat cccactggtc tac                                             23

<210> SEQ ID NO 163
<211> LENGTH: 21
<212> TYPE: DNA
<213> ORGANISM: Bos taurus

<400> SEQUENCE: 163
atcgaaccct catctcctgt g                                               21

<210> SEQ ID NO 164
<211> LENGTH: 22
<212> TYPE: DNA
<213> ORGANISM: Bos taurus

<400> SEQUENCE: 164
gtgctcaaca tcatcaatgt gg                                              22

<210> SEQ ID NO 165
<211> LENGTH: 22
<212> TYPE: DNA
<213> ORGANISM: Bos taurus

<400> SEQUENCE: 165
ttgtggttcc cacattttct ct                                              22
```

<210> SEQ ID NO 166
<211> LENGTH: 22
<212> TYPE: DNA
<213> ORGANISM: Bos taurus

<400> SEQUENCE: 166
cttgctttgt gtcctatggt tg                                              22

<210> SEQ ID NO 167
<211> LENGTH: 22
<212> TYPE: DNA
<213> ORGANISM: Bos taurus

<400> SEQUENCE: 167
aggactctgg aaggcaatac ac                                              22

<210> SEQ ID NO 168
<211> LENGTH: 22
<212> TYPE: DNA
<213> ORGANISM: Bos taurus

<400> SEQUENCE: 168
tcctcagaga aaatgtggga ac                                              22

<210> SEQ ID NO 169
<211> LENGTH: 22
<212> TYPE: DNA
<213> ORGANISM: Bos taurus

<400> SEQUENCE: 169
caacaaccac attgtaccaa cc                                              22

<210> SEQ ID NO 170
<211> LENGTH: 22
<212> TYPE: DNA
<213> ORGANISM: Bos taurus

<400> SEQUENCE: 170
gagagcttga tccaaaagca gt                                              22

<210> SEQ ID NO 171
<211> LENGTH: 22
<212> TYPE: DNA
<213> ORGANISM: Bos taurus

<400> SEQUENCE: 171
tattcccacc attccagaaa ac                                              22

<210> SEQ ID NO 172
<211> LENGTH: 22
<212> TYPE: DNA
<213> ORGANISM: Bos taurus

<400> SEQUENCE: 172
ggcgagcaat tttatattcc ag                                              22

<210> SEQ ID NO 173
<211> LENGTH: 23
<212> TYPE: DNA
<213> ORGANISM: Bos taurus

<400> SEQUENCE: 173
gagtaggctt gagatggtct ttt                                             23

<210> SEQ ID NO 174
<211> LENGTH: 22
<212> TYPE: DNA
<213> ORGANISM: Bos taurus

<400> SEQUENCE: 174
tcagatccca cagaattgca ta                                          22

<210> SEQ ID NO 175
<211> LENGTH: 22
<212> TYPE: DNA
<213> ORGANISM: Bos taurus

<400> SEQUENCE: 175
ttcggcactg ggagttattt at                                          22

<210> SEQ ID NO 176
<211> LENGTH: 22
<212> TYPE: DNA
<213> ORGANISM: Bos taurus

<400> SEQUENCE: 176
tttgctgaga atggaaactt ga                                          22

<210> SEQ ID NO 177
<211> LENGTH: 22
<212> TYPE: DNA
<213> ORGANISM: Bos taurus

<400> SEQUENCE: 177
actgacttcg cctttccaat aa                                          22

<210> SEQ ID NO 178
<211> LENGTH: 22
<212> TYPE: DNA
<213> ORGANISM: Bos taurus

<400> SEQUENCE: 178
ccagatcttt tacagcaggt ca                                          22

<210> SEQ ID NO 179
<211> LENGTH: 23
<212> TYPE: DNA
<213> ORGANISM: Bos taurus

<400> SEQUENCE: 179
aaagacacag gctcttgctc aat                                         23

<210> SEQ ID NO 180
<211> LENGTH: 22
<212> TYPE: DNA
<213> ORGANISM: Bos taurus

<400> SEQUENCE: 180
tctgcacaga aacagagaat gg                                          22

<210> SEQ ID NO 181
<211> LENGTH: 23
<212> TYPE: DNA
<213> ORGANISM: Bos taurus

<400> SEQUENCE: 181

```
ctggcaataa agcaattcta tcc                                              23

<210> SEQ ID NO 182
<211> LENGTH: 25
<212> TYPE: DNA
<213> ORGANISM: Bos taurus

<400> SEQUENCE: 182
acattgtcac agagtgctat aaacc                                            25

<210> SEQ ID NO 183
<211> LENGTH: 23
<212> TYPE: DNA
<213> ORGANISM: Bos taurus

<400> SEQUENCE: 183
aaggttctac atggcaactc tta                                              23

<210> SEQ ID NO 184
<211> LENGTH: 22
<212> TYPE: DNA
<213> ORGANISM: Bos taurus

<400> SEQUENCE: 184
attggctcag acatgaaaca ga                                               22

<210> SEQ ID NO 185
<211> LENGTH: 24
<212> TYPE: DNA
<213> ORGANISM: Bos taurus

<400> SEQUENCE: 185
gacgagacat ttagatcctc ccta                                             24

<210> SEQ ID NO 186
<211> LENGTH: 22
<212> TYPE: DNA
<213> ORGANISM: Bos taurus

<400> SEQUENCE: 186
caagactggt tgacatgctc tc                                               22

<210> SEQ ID NO 187
<211> LENGTH: 23
<212> TYPE: DNA
<213> ORGANISM: Bos taurus

<400> SEQUENCE: 187
cacagcttca ccagacatta cat                                              23

<210> SEQ ID NO 188
<211> LENGTH: 22
<212> TYPE: DNA
<213> ORGANISM: Bos taurus

<400> SEQUENCE: 188
gaagtttaaa tgcctgccaa ag                                               22

<210> SEQ ID NO 189
<211> LENGTH: 21
<212> TYPE: DNA
<213> ORGANISM: Bos taurus

<400> SEQUENCE: 189
```

-continued ctcagaaaac tgctcccaga c        21

<210> SEQ ID NO 190
<211> LENGTH: 22
<212> TYPE: DNA
<213> ORGANISM: Bos taurus

<400> SEQUENCE: 190
cagctgtcac acaagtgcat ag        22

<210> SEQ ID NO 191
<211> LENGTH: 22
<212> TYPE: DNA
<213> ORGANISM: Bos taurus

<400> SEQUENCE: 191
tggatttgag ctacaccatt tg        22

<210> SEQ ID NO 192
<211> LENGTH: 23
<212> TYPE: DNA
<213> ORGANISM: Bos taurus

<400> SEQUENCE: 192
gtagtccttg ttttggagat gag        23

<210> SEQ ID NO 193
<211> LENGTH: 21
<212> TYPE: DNA
<213> ORGANISM: Bos taurus

<400> SEQUENCE: 193
acttacttgg tgggtggcat t        21

<210> SEQ ID NO 194
<211> LENGTH: 22
<212> TYPE: DNA
<213> ORGANISM: Bos taurus

<400> SEQUENCE: 194
tacactgcaa cactttggac ct        22

<210> SEQ ID NO 195
<211> LENGTH: 22
<212> TYPE: DNA
<213> ORGANISM: Bos taurus

<400> SEQUENCE: 195
gatccagaac caaagcaagg tc        22

<210> SEQ ID NO 196
<211> LENGTH: 22
<212> TYPE: DNA
<213> ORGANISM: Bos taurus

<400> SEQUENCE: 196
ggatccaaaa tggagctatg ag        22

<210> SEQ ID NO 197
<211> LENGTH: 20
<212> TYPE: DNA
<213> ORGANISM: Bos taurus

<400> SEQUENCE: 197
cagtgcaggt gcctctcaac    20

<210> SEQ ID NO 198
<211> LENGTH: 22
<212> TYPE: DNA
<213> ORGANISM: Bos taurus

<400> SEQUENCE: 198
ttacctttgg acaaatgcag ag    22

<210> SEQ ID NO 199
<211> LENGTH: 25
<212> TYPE: DNA
<213> ORGANISM: Bos taurus

<400> SEQUENCE: 199
attactttat gcaattggca agaac    25

<210> SEQ ID NO 200
<211> LENGTH: 22
<212> TYPE: DNA
<213> ORGANISM: Bos taurus

<400> SEQUENCE: 200
gacctgaagt ggatttggaa tg    22

<210> SEQ ID NO 201
<211> LENGTH: 22
<212> TYPE: DNA
<213> ORGANISM: Bos taurus

<400> SEQUENCE: 201
accatacact tggcctttca at    22

<210> SEQ ID NO 202
<211> LENGTH: 22
<212> TYPE: DNA
<213> ORGANISM: Bos taurus

<400> SEQUENCE: 202
gaagtcaatc aaacatggtg ct    22

<210> SEQ ID NO 203
<211> LENGTH: 22
<212> TYPE: DNA
<213> ORGANISM: Bos taurus

<400> SEQUENCE: 203
tcagcctcag cactattgac at    22

<210> SEQ ID NO 204
<211> LENGTH: 22
<212> TYPE: DNA
<213> ORGANISM: Bos taurus

<400> SEQUENCE: 204
agtggcttct ccaagagcat ac    22

<210> SEQ ID NO 205
<211> LENGTH: 22
<212> TYPE: DNA
<213> ORGANISM: Bos taurus

```
<400> SEQUENCE: 205
ccaccagaaa gcagaaacag at                                              22

<210> SEQ ID NO 206
<211> LENGTH: 22
<212> TYPE: DNA
<213> ORGANISM: Bos taurus

<400> SEQUENCE: 206
tgtgataagg aagcagttga gg                                              22

<210> SEQ ID NO 207
<211> LENGTH: 21
<212> TYPE: DNA
<213> ORGANISM: Bos taurus

<400> SEQUENCE: 207
gagcatggct ttggtgaaat a                                               21

<210> SEQ ID NO 208
<211> LENGTH: 23
<212> TYPE: DNA
<213> ORGANISM: Bos taurus

<400> SEQUENCE: 208
agtgagaaca ctgaaccaga ttg                                             23

<210> SEQ ID NO 209
<211> LENGTH: 22
<212> TYPE: DNA
<213> ORGANISM: Bos taurus

<400> SEQUENCE: 209
cacaagtgct ttctccttac ca                                              22

<210> SEQ ID NO 210
<211> LENGTH: 22
<212> TYPE: DNA
<213> ORGANISM: Bos taurus

<400> SEQUENCE: 210
tcttcattcc atgagtcacc ac                                              22

<210> SEQ ID NO 211
<211> LENGTH: 22
<212> TYPE: DNA
<213> ORGANISM: Bos taurus

<400> SEQUENCE: 211
aaagtttcca gccgttcata ga                                              22

<210> SEQ ID NO 212
<211> LENGTH: 22
<212> TYPE: DNA
<213> ORGANISM: Bos taurus

<400> SEQUENCE: 212
tggtggttga gagcaacatt ac                                              22

<210> SEQ ID NO 213
<211> LENGTH: 20
<212> TYPE: DNA
```

<213> ORGANISM: Bos taurus

<400> SEQUENCE: 213
aaatctggct ggcatttctg                                              20

<210> SEQ ID NO 214
<211> LENGTH: 22
<212> TYPE: DNA
<213> ORGANISM: Bos taurus

<400> SEQUENCE: 214
aggagttcca atttccagtt ca                                           22

<210> SEQ ID NO 215
<211> LENGTH: 22
<212> TYPE: DNA
<213> ORGANISM: Bos taurus

<400> SEQUENCE: 215
atagaactgc tccacgcata ac                                           22

<210> SEQ ID NO 216
<211> LENGTH: 22
<212> TYPE: DNA
<213> ORGANISM: Bos taurus

<400> SEQUENCE: 216
ccaataatcc catttcagaa gc                                           22

<210> SEQ ID NO 217
<211> LENGTH: 22
<212> TYPE: DNA
<213> ORGANISM: Bos taurus

<400> SEQUENCE: 217
acgagtcttc aaacctgtct cc                                           22

<210> SEQ ID NO 218
<211> LENGTH: 22
<212> TYPE: DNA
<213> ORGANISM: Bos taurus

<400> SEQUENCE: 218
atgcataaag gtccaagtcc ag                                           22

<210> SEQ ID NO 219
<211> LENGTH: 22
<212> TYPE: DNA
<213> ORGANISM: Bos taurus

<400> SEQUENCE: 219
atcacatccc tcaatgtggt tc                                           22

<210> SEQ ID NO 220
<211> LENGTH: 22
<212> TYPE: DNA
<213> ORGANISM: Bos taurus

<400> SEQUENCE: 220
tggtttcgag atgattcaag tg                                           22

<210> SEQ ID NO 221
<211> LENGTH: 21

```
<212> TYPE: DNA
<213> ORGANISM: Bos taurus

<400> SEQUENCE: 221
agggtggagc cgatgtaata a                                           21

<210> SEQ ID NO 222
<211> LENGTH: 22
<212> TYPE: DNA
<213> ORGANISM: Bos taurus

<400> SEQUENCE: 222
cactattgga cacaaagcca tc                                          22

<210> SEQ ID NO 223
<211> LENGTH: 22
<212> TYPE: DNA
<213> ORGANISM: Bos taurus

<400> SEQUENCE: 223
ccctcatcac tcaccaaaac ta                                          22

<210> SEQ ID NO 224
<211> LENGTH: 22
<212> TYPE: DNA
<213> ORGANISM: Bos taurus

<400> SEQUENCE: 224
actagacggc ataaagcatg aa                                          22

<210> SEQ ID NO 225
<211> LENGTH: 25
<212> TYPE: DNA
<213> ORGANISM: Bos taurus

<400> SEQUENCE: 225
tcctctaaca acacataatc tagcc                                       25

<210> SEQ ID NO 226
<211> LENGTH: 23
<212> TYPE: DNA
<213> ORGANISM: Bos taurus

<400> SEQUENCE: 226
gggtacacag ttgtccagaa gac                                         23

<210> SEQ ID NO 227
<211> LENGTH: 22
<212> TYPE: DNA
<213> ORGANISM: Bos taurus

<400> SEQUENCE: 227
actcagtgac ttcagcaatg ga                                          22

<210> SEQ ID NO 228
<211> LENGTH: 22
<212> TYPE: DNA
<213> ORGANISM: Bos taurus

<400> SEQUENCE: 228
ctggactagg ggatacagag ga                                          22

<210> SEQ ID NO 229
```

```
<211> LENGTH: 22
<212> TYPE: DNA
<213> ORGANISM: Bos taurus

<400> SEQUENCE: 229
tccattacaa gttccacgca aa                                              22

<210> SEQ ID NO 230
<211> LENGTH: 22
<212> TYPE: DNA
<213> ORGANISM: Bos taurus

<400> SEQUENCE: 230
agaggaagct ctcaaggagg at                                              22

<210> SEQ ID NO 231
<211> LENGTH: 22
<212> TYPE: DNA
<213> ORGANISM: Bos taurus

<400> SEQUENCE: 231
tactgaggtt gcaagtgggt ta                                              22

<210> SEQ ID NO 232
<211> LENGTH: 22
<212> TYPE: DNA
<213> ORGANISM: Bos taurus

<400> SEQUENCE: 232
ggtaatagag cgtggtgacc tt                                              22

<210> SEQ ID NO 233
<211> LENGTH: 22
<212> TYPE: DNA
<213> ORGANISM: Bos taurus

<400> SEQUENCE: 233
cctccctgtg gtattttctc tg                                              22

<210> SEQ ID NO 234
<211> LENGTH: 21
<212> TYPE: DNA
<213> ORGANISM: Bos taurus

<400> SEQUENCE: 234
ctggatagct ggcatcaaga c                                               21

<210> SEQ ID NO 235
<211> LENGTH: 20
<212> TYPE: DNA
<213> ORGANISM: Bos taurus

<400> SEQUENCE: 235
ctagggtgag gcgatggaaa                                                 20

<210> SEQ ID NO 236
<211> LENGTH: 22
<212> TYPE: DNA
<213> ORGANISM: Bos taurus

<400> SEQUENCE: 236
ttgagttgca agatccaaat gt                                              22
```

```
<210> SEQ ID NO 237
<211> LENGTH: 22
<212> TYPE: DNA
<213> ORGANISM: Bos taurus

<400> SEQUENCE: 237
agtgggatca ttcctgtgaa ac                                              22

<210> SEQ ID NO 238
<211> LENGTH: 21
<212> TYPE: DNA
<213> ORGANISM: Bos taurus

<400> SEQUENCE: 238
gaggtctggg aaatgtcaag g                                               21

<210> SEQ ID NO 239
<211> LENGTH: 22
<212> TYPE: DNA
<213> ORGANISM: Bos taurus

<400> SEQUENCE: 239
ccctttcagg gaaatctagg ac                                              22

<210> SEQ ID NO 240
<211> LENGTH: 23
<212> TYPE: DNA
<213> ORGANISM: Bos taurus

<400> SEQUENCE: 240
tggtaaggga ttaggatctc aca                                             23

<210> SEQ ID NO 241
<211> LENGTH: 20
<212> TYPE: DNA
<213> ORGANISM: Bos taurus

<400> SEQUENCE: 241
ttggctgcaa ggtatgtgag                                                 20

<210> SEQ ID NO 242
<211> LENGTH: 22
<212> TYPE: DNA
<213> ORGANISM: Bos taurus

<400> SEQUENCE: 242
tgaacctgga attgtgttct tg                                              22

<210> SEQ ID NO 243
<211> LENGTH: 22
<212> TYPE: DNA
<213> ORGANISM: Bos taurus

<400> SEQUENCE: 243
aaaacatttg gaaaagcacg at                                              22

<210> SEQ ID NO 244
<211> LENGTH: 22
<212> TYPE: DNA
<213> ORGANISM: Bos taurus

<400> SEQUENCE: 244
gaactatctc tgcattgagc ac                                              22
```

<210> SEQ ID NO 245
<211> LENGTH: 22
<212> TYPE: DNA
<213> ORGANISM: Bos taurus

<400> SEQUENCE: 245
aaggatgtca aacaaacaag ca                                    22

<210> SEQ ID NO 246
<211> LENGTH: 22
<212> TYPE: DNA
<213> ORGANISM: Bos taurus

<400> SEQUENCE: 246
tccttaatac cttcccagga ca                                    22

<210> SEQ ID NO 247
<211> LENGTH: 22
<212> TYPE: DNA
<213> ORGANISM: Bos taurus

<400> SEQUENCE: 247
tgatcatgta gaagggaaag ca                                    22

<210> SEQ ID NO 248
<211> LENGTH: 22
<212> TYPE: DNA
<213> ORGANISM: Bos taurus

<400> SEQUENCE: 248
tttcaccata agcggaaaca ta                                    22

<210> SEQ ID NO 249
<211> LENGTH: 22
<212> TYPE: DNA
<213> ORGANISM: Bos taurus

<400> SEQUENCE: 249
atcagagcaa gagggacttc ac                                    22

<210> SEQ ID NO 250
<211> LENGTH: 22
<212> TYPE: DNA
<213> ORGANISM: Bos taurus

<400> SEQUENCE: 250
cttgcagaat agaggaggca gt                                    22

<210> SEQ ID NO 251
<211> LENGTH: 22
<212> TYPE: DNA
<213> ORGANISM: Bos taurus

<400> SEQUENCE: 251
ggagatagaa gaaccacgga at                                    22

<210> SEQ ID NO 252
<211> LENGTH: 20
<212> TYPE: DNA
<213> ORGANISM: Bos taurus

<400> SEQUENCE: 252
cagcagcagc agactgaaac                                       20

<210> SEQ ID NO 253
<211> LENGTH: 22
<212> TYPE: DNA
<213> ORGANISM: Bos taurus

<400> SEQUENCE: 253
ccctcttatc cctgtgaaac tg                                              22

<210> SEQ ID NO 254
<211> LENGTH: 22
<212> TYPE: DNA
<213> ORGANISM: Bos taurus

<400> SEQUENCE: 254
tccttcctta aaagaccacc aa                                              22

<210> SEQ ID NO 255
<211> LENGTH: 22
<212> TYPE: DNA
<213> ORGANISM: Bos taurus

<400> SEQUENCE: 255
agcattccag tcagcaagat tt                                              22

<210> SEQ ID NO 256
<211> LENGTH: 22
<212> TYPE: DNA
<213> ORGANISM: Bos taurus

<400> SEQUENCE: 256
tgaaattgct caagaaacat gg                                              22

<210> SEQ ID NO 257
<211> LENGTH: 21
<212> TYPE: DNA
<213> ORGANISM: Bos taurus

<400> SEQUENCE: 257
ctggcttcgc tccagatttt a                                               21

<210> SEQ ID NO 258
<211> LENGTH: 22
<212> TYPE: DNA
<213> ORGANISM: Bos taurus

<400> SEQUENCE: 258
ttagcagcag caagaccatt ta                                              22

<210> SEQ ID NO 259
<211> LENGTH: 22
<212> TYPE: DNA
<213> ORGANISM: Bos taurus

<400> SEQUENCE: 259
tttagtgctt ggacagacct ga                                              22

<210> SEQ ID NO 260
<211> LENGTH: 22
<212> TYPE: DNA
<213> ORGANISM: Bos taurus

<400> SEQUENCE: 260

```
agctgacaga tttcccaatt tc                                          22

<210> SEQ ID NO 261
<211> LENGTH: 22
<212> TYPE: DNA
<213> ORGANISM: Bos taurus

<400> SEQUENCE: 261
aaagctggag acagaacagt ca                                          22

<210> SEQ ID NO 262
<211> LENGTH: 22
<212> TYPE: DNA
<213> ORGANISM: Bos taurus

<400> SEQUENCE: 262
aactcctctg gcaggttatg aa                                          22

<210> SEQ ID NO 263
<211> LENGTH: 25
<212> TYPE: DNA
<213> ORGANISM: Bos taurus

<400> SEQUENCE: 263
cctactagag agtaagggtg acttg                                       25

<210> SEQ ID NO 264
<211> LENGTH: 23
<212> TYPE: DNA
<213> ORGANISM: Bos taurus

<400> SEQUENCE: 264
aatgtaggat gacaaccatc tgc                                         23

<210> SEQ ID NO 265
<211> LENGTH: 22
<212> TYPE: DNA
<213> ORGANISM: Bos taurus

<400> SEQUENCE: 265
gaatcaaaga tggaaggaaa gc                                          22

<210> SEQ ID NO 266
<211> LENGTH: 22
<212> TYPE: DNA
<213> ORGANISM: Bos taurus

<400> SEQUENCE: 266
gggtattggg agaagtgagt ga                                          22

<210> SEQ ID NO 267
<211> LENGTH: 21
<212> TYPE: DNA
<213> ORGANISM: Bos taurus

<400> SEQUENCE: 267
atgcttgaga atctttccct g                                           21

<210> SEQ ID NO 268
<211> LENGTH: 21
<212> TYPE: DNA
<213> ORGANISM: Bos taurus

<400> SEQUENCE: 268
```

```
agaccctgc taaattgtaa c                                              21

<210> SEQ ID NO 269
<211> LENGTH: 22
<212> TYPE: DNA
<213> ORGANISM: Bos taurus

<400> SEQUENCE: 269
ggtagattcc ccaaggagaa ag                                            22

<210> SEQ ID NO 270
<211> LENGTH: 22
<212> TYPE: DNA
<213> ORGANISM: Bos taurus

<400> SEQUENCE: 270
ccttggactc ctattttcca ga                                            22

<210> SEQ ID NO 271
<211> LENGTH: 23
<212> TYPE: DNA
<213> ORGANISM: Bos taurus

<400> SEQUENCE: 271
caggatacag ttgccttagt tcc                                           23

<210> SEQ ID NO 272
<211> LENGTH: 22
<212> TYPE: DNA
<213> ORGANISM: Bos taurus

<400> SEQUENCE: 272
aaaacatcag agggaaaatg ac                                            22

<210> SEQ ID NO 273
<211> LENGTH: 22
<212> TYPE: DNA
<213> ORGANISM: Bos taurus

<400> SEQUENCE: 273 gaccctcaa cacagaagta cc                                             22

<210> SEQ ID NO 274
<211> LENGTH: 22
<212> TYPE: DNA
<213> ORGANISM: Bos taurus

<400> SEQUENCE: 274
attgtcaggt gggtattcaa gc                                            22

<210> SEQ ID NO 275
<211> LENGTH: 22
<212> TYPE: DNA
<213> ORGANISM: Bos taurus

<400> SEQUENCE: 275
gatccttggg aagtctgttg tc                                            22

<210> SEQ ID NO 276
<211> LENGTH: 21
<212> TYPE: DNA
<213> ORGANISM: Bos taurus
```

```
<400> SEQUENCE: 276
accaacttca ggttcacatg c                                          21

<210> SEQ ID NO 277
<211> LENGTH: 22
<212> TYPE: DNA
<213> ORGANISM: Bos taurus

<400> SEQUENCE: 277
cacagcctga gaagcactga ta                                         22

<210> SEQ ID NO 278
<211> LENGTH: 22
<212> TYPE: DNA
<213> ORGANISM: Bos taurus

<400> SEQUENCE: 278
cccataagga gaggaggagt tt                                         22

<210> SEQ ID NO 279
<211> LENGTH: 22
<212> TYPE: DNA
<213> ORGANISM: Bos taurus

<400> SEQUENCE: 279
tcagaaggat catgagagca ga                                         22

<210> SEQ ID NO 280
<211> LENGTH: 22
<212> TYPE: DNA
<213> ORGANISM: Bos taurus

<400> SEQUENCE: 280
accagactct tgctatccca ac                                         22

<210> SEQ ID NO 281
<211> LENGTH: 22
<212> TYPE: DNA
<213> ORGANISM: Bos taurus

<400> SEQUENCE: 281
catgcatctg ggtgagaact aa                                         22

<210> SEQ ID NO 282
<211> LENGTH: 22
<212> TYPE: DNA
<213> ORGANISM: Bos taurus

<400> SEQUENCE: 282
tgcaagtttc tctggagatt ga                                         22

<210> SEQ ID NO 283
<211> LENGTH: 22
<212> TYPE: DNA
<213> ORGANISM: Bos taurus

<400> SEQUENCE: 283
caaaggcatc catctgttct aa                                         22

<210> SEQ ID NO 284
<211> LENGTH: 22
<212> TYPE: DNA
<213> ORGANISM: Bos taurus
```

```
<400> SEQUENCE: 284
gtcttcctct tcctcctcct tt                                              22

<210> SEQ ID NO 285
<211> LENGTH: 23
<212> TYPE: DNA
<213> ORGANISM: Bos taurus

<400> SEQUENCE: 285
tggttcattg agaagataca gga                                             23

<210> SEQ ID NO 286
<211> LENGTH: 20
<212> TYPE: DNA
<213> ORGANISM: Bos taurus

<400> SEQUENCE: 286
gggacctccc aagaaagaat                                                 20

<210> SEQ ID NO 287
<211> LENGTH: 22
<212> TYPE: DNA
<213> ORGANISM: Bos taurus

<400> SEQUENCE: 287
gagctaatca tggtggctca gt                                              22

<210> SEQ ID NO 288
<211> LENGTH: 22
<212> TYPE: DNA
<213> ORGANISM: Bos taurus

<400> SEQUENCE: 288
cggctcatct ccaagctaaa ag                                              22

<210> SEQ ID NO 289
<211> LENGTH: 24
<212> TYPE: DNA
<213> ORGANISM: Bos taurus

<400> SEQUENCE: 289
gaggtttgga gataacagac atga                                            24

<210> SEQ ID NO 290
<211> LENGTH: 22
<212> TYPE: DNA
<213> ORGANISM: Bos taurus

<400> SEQUENCE: 290
gctgaatgtt tcctttggag ag                                              22

<210> SEQ ID NO 291
<211> LENGTH: 22
<212> TYPE: DNA
<213> ORGANISM: Bos taurus

<400> SEQUENCE: 291
catcaaggaa gcccaagaat ac                                              22

<210> SEQ ID NO 292
<211> LENGTH: 22
<212> TYPE: DNA
```

```
<213> ORGANISM: Bos taurus

<400> SEQUENCE: 292
aattaggagg ctgagaaagg tc                                    22

<210> SEQ ID NO 293
<211> LENGTH: 22
<212> TYPE: DNA
<213> ORGANISM: Bos taurus

<400> SEQUENCE: 293
tcctcatgcc tcaaaacctt ta                                    22

<210> SEQ ID NO 294
<211> LENGTH: 22
<212> TYPE: DNA
<213> ORGANISM: Bos taurus

<400> SEQUENCE: 294
tgccatatgc agagaggaaa ta                                    22

<210> SEQ ID NO 295
<211> LENGTH: 21
<212> TYPE: DNA
<213> ORGANISM: Bos taurus

<400> SEQUENCE: 295
ggaagccaat gttgttttca g                                     21

<210> SEQ ID NO 296
<211> LENGTH: 22
<212> TYPE: DNA
<213> ORGANISM: Bos taurus

<400> SEQUENCE: 296
accaccacgt tatctcccat ac                                    22

<210> SEQ ID NO 297
<211> LENGTH: 22
<212> TYPE: DNA
<213> ORGANISM: Bos taurus

<400> SEQUENCE: 297
ctctcttccc acatctgaaa gg                                    22

<210> SEQ ID NO 298
<211> LENGTH: 23
<212> TYPE: DNA
<213> ORGANISM: Bos taurus

<400> SEQUENCE: 298
tttctcccaa ataatccact cac                                   23

<210> SEQ ID NO 299
<211> LENGTH: 22
<212> TYPE: DNA
<213> ORGANISM: Bos taurus

<400> SEQUENCE: 299
ctacacctat cccatgcctt gc                                    22

<210> SEQ ID NO 300
<211> LENGTH: 22
```

```
<212> TYPE: DNA
<213> ORGANISM: Bos taurus

<400> SEQUENCE: 300
ataccagtga aggaggcaac at                                              22

<210> SEQ ID NO 301
<211> LENGTH: 22
<212> TYPE: DNA
<213> ORGANISM: Bos taurus

<400> SEQUENCE: 301
aagtggcaga ttccagattt gt                                              22

<210> SEQ ID NO 302
<211> LENGTH: 22
<212> TYPE: DNA
<213> ORGANISM: Bos taurus

<400> SEQUENCE: 302
gtttgctggt cccactactt ct                                              22

<210> SEQ ID NO 303
<211> LENGTH: 21
<212> TYPE: DNA
<213> ORGANISM: Bos taurus

<400> SEQUENCE: 303
aacagggcca caattcctag a                                               21

<210> SEQ ID NO 304
<211> LENGTH: 22
<212> TYPE: DNA
<213> ORGANISM: Bos taurus

<400> SEQUENCE: 304
gaaagatgcc ttcagtgctg tt                                              22

<210> SEQ ID NO 305
<211> LENGTH: 22
<212> TYPE: DNA
<213> ORGANISM: Bos taurus

<400> SEQUENCE: 305
caatgcatga aagttgtgtg tg                                              22

<210> SEQ ID NO 306
<211> LENGTH: 24
<212> TYPE: DNA
<213> ORGANISM: Bos taurus

<400> SEQUENCE: 306
gggctattcc tagaaaattc acct                                            24

<210> SEQ ID NO 307
<211> LENGTH: 22
<212> TYPE: DNA
<213> ORGANISM: Bos taurus

<400> SEQUENCE: 307
gttggtgtag gaaacctgtc tg                                              22

<210> SEQ ID NO 308
```

-continued

<210> SEQ ID NO 308
<211> LENGTH: 24
<212> TYPE: DNA
<213> ORGANISM: Bos taurus

<400> SEQUENCE: 308
aagagacaga catagaggac aaac                                              24

<210> SEQ ID NO 309
<211> LENGTH: 23
<212> TYPE: DNA
<213> ORGANISM: Bos taurus

<400> SEQUENCE: 309
cgactttctc ccttggtata cat                                               23

<210> SEQ ID NO 310
<211> LENGTH: 22
<212> TYPE: DNA
<213> ORGANISM: Bos taurus

<400> SEQUENCE: 310
ctctggtcat tcatcattgg tt                                                22

<210> SEQ ID NO 311
<211> LENGTH: 22
<212> TYPE: DNA
<213> ORGANISM: Bos taurus

<400> SEQUENCE: 311
atgtagcacc aataaaggca gt                                                22

<210> SEQ ID NO 312
<211> LENGTH: 22
<212> TYPE: DNA
<213> ORGANISM: Bos taurus

<400> SEQUENCE: 312
aaactcatcg aggccaacta aa                                                22

<210> SEQ ID NO 313
<211> LENGTH: 22
<212> TYPE: DNA
<213> ORGANISM: Bos taurus

<400> SEQUENCE: 313
ggtttgagca tcttcaggaa ct                                                22

<210> SEQ ID NO 314
<211> LENGTH: 22
<212> TYPE: DNA
<213> ORGANISM: Bos taurus

<400> SEQUENCE: 314
aggcttgatt tctggttcta ca                                                22

<210> SEQ ID NO 315
<211> LENGTH: 21
<212> TYPE: DNA
<213> ORGANISM: Bos taurus

<400> SEQUENCE: 315
ggcctctcaa ttggtgagaa a                                                 21

-continued

<210> SEQ ID NO 316
<211> LENGTH: 22
<212> TYPE: DNA
<213> ORGANISM: Bos taurus

<400> SEQUENCE: 316
catcatccac cacaggtaac aa					22

<210> SEQ ID NO 317
<211> LENGTH: 22
<212> TYPE: DNA
<213> ORGANISM: Bos taurus

<400> SEQUENCE: 317
cctgagaggt ccatcttttc tg					22

<210> SEQ ID NO 318
<211> LENGTH: 22
<212> TYPE: DNA
<213> ORGANISM: Bos taurus

<400> SEQUENCE: 318
gcaaaggtgt cattaggagc tt					22

<210> SEQ ID NO 319
<211> LENGTH: 22
<212> TYPE: DNA
<213> ORGANISM: Bos taurus

<400> SEQUENCE: 319
caaaactagc attgtgcaga gg					22

<210> SEQ ID NO 320
<211> LENGTH: 22
<212> TYPE: DNA
<213> ORGANISM: Bos taurus

<400> SEQUENCE: 320
agctggccta cttttcttcc tt					22

<210> SEQ ID NO 321
<211> LENGTH: 22
<212> TYPE: DNA
<213> ORGANISM: Bos taurus

<400> SEQUENCE: 321
cgagagagaa gcagacagaa ag					22

<210> SEQ ID NO 322
<211> LENGTH: 22
<212> TYPE: DNA
<213> ORGANISM: Bos taurus

<400> SEQUENCE: 322
caattccaag tggaggaaag ag					22

<210> SEQ ID NO 323
<211> LENGTH: 21
<212> TYPE: DNA
<213> ORGANISM: Bos taurus

<400> SEQUENCE: 323
aagtcggagt attggcagga t						21

```
<210> SEQ ID NO 324
<211> LENGTH: 22
<212> TYPE: DNA
<213> ORGANISM: Bos taurus

<400> SEQUENCE: 324
agtccatgtt gattttgtgc tg                                                  22

<210> SEQ ID NO 325
<211> LENGTH: 21
<212> TYPE: DNA
<213> ORGANISM: Bos taurus

<400> SEQUENCE: 325
aagtcggagt attggcagga t                                                   21

<210> SEQ ID NO 326
<211> LENGTH: 22
<212> TYPE: DNA
<213> ORGANISM: Bos taurus

<400> SEQUENCE: 326
tgcaggttac tctcaggtgg ta                                                  22

<210> SEQ ID NO 327
<211> LENGTH: 22
<212> TYPE: DNA
<213> ORGANISM: Bos taurus

<400> SEQUENCE: 327
tggaaccagc ctcaggtata ag                                                  22

<210> SEQ ID NO 328
<211> LENGTH: 22
<212> TYPE: DNA
<213> ORGANISM: Bos taurus

<400> SEQUENCE: 328
cggagattcc atgtagccta gt                                                  22

<210> SEQ ID NO 329
<211> LENGTH: 24
<212> TYPE: DNA
<213> ORGANISM: Bos taurus

<400> SEQUENCE: 329
agtagcactg tgtgtgtgtt agat                                                24

<210> SEQ ID NO 330
<211> LENGTH: 22
<212> TYPE: DNA
<213> ORGANISM: Bos taurus

<400> SEQUENCE: 330
attgcattat tttcccaagg ac                                                  22

<210> SEQ ID NO 331
<211> LENGTH: 20
<212> TYPE: DNA
<213> ORGANISM: Bos taurus

<400> SEQUENCE: 331
ctggtttcag accctggcta                                                     20
```

<210> SEQ ID NO 332
<211> LENGTH: 22
<212> TYPE: DNA
<213> ORGANISM: Bos taurus

<400> SEQUENCE: 332 tccacccttf catcctaaca gc                                            22

<210> SEQ ID NO 333
<211> LENGTH: 22
<212> TYPE: DNA
<213> ORGANISM: Bos taurus

<400> SEQUENCE: 333
gcctctcaca agcatttgat ct                                            22

<210> SEQ ID NO 334
<211> LENGTH: 22
<212> TYPE: DNA
<213> ORGANISM: Bos taurus

<400> SEQUENCE: 334
atgagtatca gggaatggtg ct                                            22

<210> SEQ ID NO 335
<211> LENGTH: 21
<212> TYPE: DNA
<213> ORGANISM: Bos taurus

<400> SEQUENCE: 335
agatctgcaa ggtcaaaatc a                                             21

<210> SEQ ID NO 336
<211> LENGTH: 22
<212> TYPE: DNA
<213> ORGANISM: Bos taurus

<400> SEQUENCE: 336
tttctcccaa aactatttgc tg                                            22

<210> SEQ ID NO 337
<211> LENGTH: 22
<212> TYPE: DNA
<213> ORGANISM: Bos taurus

<400> SEQUENCE: 337
aattccaaat atccttggtg gt                                            22

<210> SEQ ID NO 338
<211> LENGTH: 22
<212> TYPE: DNA
<213> ORGANISM: Bos taurus

<400> SEQUENCE: 338
tggaaggctt ttctgaactt tt                                            22

<210> SEQ ID NO 339
<211> LENGTH: 22
<212> TYPE: DNA
<213> ORGANISM: Bos taurus

<400> SEQUENCE: 339
cacgtcaatc tcaaacagat gc                                              22

<210> SEQ ID NO 340
<211> LENGTH: 22
<212> TYPE: DNA
<213> ORGANISM: Bos taurus

<400> SEQUENCE: 340
tatcctgtct tggcaattcc tt                                              22

<210> SEQ ID NO 341
<211> LENGTH: 23
<212> TYPE: DNA
<213> ORGANISM: Bos taurus

<400> SEQUENCE: 341
ttcaaacaga gtcaggtggt atc                                             23

<210> SEQ ID NO 342
<211> LENGTH: 21
<212> TYPE: DNA
<213> ORGANISM: Bos taurus

<400> SEQUENCE: 342
gcaggtagca tagtcccttc a                                               21

<210> SEQ ID NO 343
<211> LENGTH: 22
<212> TYPE: DNA
<213> ORGANISM: Bos taurus

<400> SEQUENCE: 343
tttaacaagc ttttcctggt tc                                              22

<210> SEQ ID NO 344
<211> LENGTH: 22
<212> TYPE: DNA
<213> ORGANISM: Bos taurus

<400> SEQUENCE: 344
atgtggttag agtgggaaag ga                                              22

<210> SEQ ID NO 345
<211> LENGTH: 23
<212> TYPE: DNA
<213> ORGANISM: Bos taurus

<400> SEQUENCE: 345
caaagatggc caataaagaa gtc                                             23

<210> SEQ ID NO 346
<211> LENGTH: 22
<212> TYPE: DNA
<213> ORGANISM: Bos taurus

<400> SEQUENCE: 346
tttagggagg aagcattgat gt                                              22

<210> SEQ ID NO 347
<211> LENGTH: 22
<212> TYPE: DNA
<213> ORGANISM: Bos taurus

<400> SEQUENCE: 347

```
gtttgtagtg ggtggagatg ga                                              22

<210> SEQ ID NO 348
<211> LENGTH: 22
<212> TYPE: DNA
<213> ORGANISM: Bos taurus

<400> SEQUENCE: 348
aacctcagga gatgacgttg tt                                              22

<210> SEQ ID NO 349
<211> LENGTH: 22
<212> TYPE: DNA
<213> ORGANISM: Bos taurus

<400> SEQUENCE: 349
ttgttcctat gtgacctcaa gc                                              22

<210> SEQ ID NO 350
<211> LENGTH: 22
<212> TYPE: DNA
<213> ORGANISM: Bos taurus

<400> SEQUENCE: 350
catctgttgc tttgctcatt gt                                              22

<210> SEQ ID NO 351
<211> LENGTH: 21
<212> TYPE: DNA
<213> ORGANISM: Bos taurus

<400> SEQUENCE: 351
cttctagcag gcctccactt g                                               21

<210> SEQ ID NO 352
<211> LENGTH: 22
<212> TYPE: DNA
<213> ORGANISM: Bos taurus

<400> SEQUENCE: 352
tagaccctgc tgatggtata tg                                              22

<210> SEQ ID NO 353
<211> LENGTH: 22
<212> TYPE: DNA
<213> ORGANISM: Bos taurus

<400> SEQUENCE: 353
catgtgcttt cttgttgctt gt                                              22

<210> SEQ ID NO 354
<211> LENGTH: 22
<212> TYPE: DNA
<213> ORGANISM: Bos taurus

<400> SEQUENCE: 354
ttgactcaga cccataggga tt                                              22

<210> SEQ ID NO 355
<211> LENGTH: 23
<212> TYPE: DNA
<213> ORGANISM: Bos taurus
```

<400> SEQUENCE: 355
ttgatcactc taatgttcca ggt          23

<210> SEQ ID NO 356
<211> LENGTH: 22
<212> TYPE: DNA
<213> ORGANISM: Bos taurus

<400> SEQUENCE: 356
ttggattaaa cattctgggt tc           22

<210> SEQ ID NO 357
<211> LENGTH: 22
<212> TYPE: DNA
<213> ORGANISM: Bos taurus

<400> SEQUENCE: 357
ccttggataa cagaactggt tg           22

<210> SEQ ID NO 358
<211> LENGTH: 23
<212> TYPE: DNA
<213> ORGANISM: Bos taurus

<400> SEQUENCE: 358
cccatctctt tctaacattg gat          23

<210> SEQ ID NO 359
<211> LENGTH: 21
<212> TYPE: DNA
<213> ORGANISM: Bos taurus

<400> SEQUENCE: 359
accctggccc aagttgtcta t            21

<210> SEQ ID NO 360
<211> LENGTH: 23
<212> TYPE: DNA
<213> ORGANISM: Bos taurus

<400> SEQUENCE: 360
ctggtgtgct acttaactgc ttg          23

<210> SEQ ID NO 361
<211> LENGTH: 22
<212> TYPE: DNA
<213> ORGANISM: Bos taurus

<400> SEQUENCE: 361
gttcctctat cccactccct tc           22

<210> SEQ ID NO 362
<211> LENGTH: 22
<212> TYPE: DNA
<213> ORGANISM: Bos taurus

<400> SEQUENCE: 362
ttaatcctca taccaccct gt            22

<210> SEQ ID NO 363
<211> LENGTH: 23
<212> TYPE: DNA
<213> ORGANISM: Bos taurus

```
<400> SEQUENCE: 363
gaaacaaaca tctgacgact ctg                                           23

<210> SEQ ID NO 364
<211> LENGTH: 22
<212> TYPE: DNA
<213> ORGANISM: Bos taurus

<400> SEQUENCE: 364
tcttgggctt aaagagagga aa                                            22

<210> SEQ ID NO 365
<211> LENGTH: 22
<212> TYPE: DNA
<213> ORGANISM: Bos taurus

<400> SEQUENCE: 365
cacctgggaa accaaatcta at                                            22

<210> SEQ ID NO 366
<211> LENGTH: 23
<212> TYPE: DNA
<213> ORGANISM: Bos taurus

<400> SEQUENCE: 366
ttatctcaac ccacagaacc cat                                           23

<210> SEQ ID NO 367
<211> LENGTH: 20
<212> TYPE: DNA
<213> ORGANISM: Bos taurus

<400> SEQUENCE: 367
gaattcagca cctccagcat                                               20

<210> SEQ ID NO 368
<211> LENGTH: 22
<212> TYPE: DNA
<213> ORGANISM: Bos taurus

<400> SEQUENCE: 368
tgagtggatt ctgatggaaa ga                                            22

<210> SEQ ID NO 369
<211> LENGTH: 22
<212> TYPE: DNA
<213> ORGANISM: Bos taurus

<400> SEQUENCE: 369
ccactcccaa ttcctcaaat ag                                            22

<210> SEQ ID NO 370
<211> LENGTH: 22
<212> TYPE: DNA
<213> ORGANISM: Bos taurus

<400> SEQUENCE: 370
ttctgccatt tgcctataag gt                                            22

<210> SEQ ID NO 371
<211> LENGTH: 10
<212> TYPE: DNA
```

```
<213> ORGANISM: Bos taurus

<400> SEQUENCE: 371
gctctactcg                                                            10

<210> SEQ ID NO 372
<211> LENGTH: 10
<212> TYPE: DNA
<213> ORGANISM: Bos taurus

<400> SEQUENCE: 372
accccgttaa                                                            10

<210> SEQ ID NO 373
<211> LENGTH: 10
<212> TYPE: DNA
<213> ORGANISM: Bos taurus

<400> SEQUENCE: 373
gccctgttag                                                            10

<210> SEQ ID NO 374
<211> LENGTH: 10
<212> TYPE: DNA
<213> ORGANISM: Bos taurus

<400> SEQUENCE: 374
atcccgtaaa                                                            10

<210> SEQ ID NO 375
<211> LENGTH: 10
<212> TYPE: DNA
<213> ORGANISM: Bos taurus

<400> SEQUENCE: 375
gccctgttaa                                                            10

<210> SEQ ID NO 376
<211> LENGTH: 10
<212> TYPE: DNA
<213> ORGANISM: Bos taurus

<400> SEQUENCE: 376
accctgttaa                                                            10

<210> SEQ ID NO 377
<211> LENGTH: 10
<212> TYPE: DNA
<213> ORGANISM: Bos taurus

<400> SEQUENCE: 377
atctcgtaaa                                                            10
```